US012559707B2

(12) United States Patent
White et al.

(10) Patent No.: US 12,559,707 B2
(45) Date of Patent: Feb. 24, 2026

(54) MODULAR, CONFIGURABLE BIOREACTOR SYSTEM FOR A MANUFACTURING LINE

(71) Applicant: DEKA Products Limited Partnership, Manchester, NH (US)

(72) Inventors: Matthew White, Henniker, NH (US); Stephanie M. Miskell, Weare, NH (US); Justin M. Ferrentino, Mont Vernon, NH (US); Richard E. Andrews, Manchester, NH (US); Stuart A. Jacobson, Lexington, MA (US); Zachary Kops, Andover, MA (US)

(73) Assignee: DEKA Limited Partnership, Manchester, NH (US)

( * ) Notice: Subject to any disclaimer, the term of this patent is extended or adjusted under 35 U.S.C. 154(b) by 921 days.

(21) Appl. No.: 17/648,466

(22) Filed: Jan. 20, 2022

(65) Prior Publication Data

US 2022/0228097 A1 Jul. 21, 2022

Related U.S. Application Data

(60) Provisional application No. 63/139,408, filed on Jan. 20, 2021.

(51) Int. Cl.
C12M 1/06 (2006.01)
C12M 1/00 (2006.01)
(Continued)

(52) U.S. Cl.
CPC ............ C12M 27/08 (2013.01); C12M 23/06 (2013.01); C12M 23/28 (2013.01); C12M 25/14 (2013.01);
(Continued)

(58) Field of Classification Search
None
See application file for complete search history.

(56) References Cited

U.S. PATENT DOCUMENTS 5,998,217 A 12/1999 Rao et al.
6,786,054 B2 9/2004 Voute et al.
(Continued)

FOREIGN PATENT DOCUMENTS

CN 201045139 Y 9/2016
WO 2003087292 10/2003
(Continued)

OTHER PUBLICATIONS

International preliminary report on patentability mailed Aug. 3, 2023, issued in PCT international app PCT/US2022/070265, 1 page.
(Continued)

*Primary Examiner* — William H. Beisner
(74) *Attorney, Agent, or Firm* — Mark E. Tetreault

(57) ABSTRACT

A configurable system for repeatably performing processes related to tissue growth in a controlled environment, possibly part of an industrial production line. The system can accommodate various sizes and shapes of culture vessels, and can maintain the cells at a desired temperature in the culture vessels, thus enabling a plug and play system that can produce consistent and repeatable results. The system includes gas management, fluid management, and control of multiple processes simultaneously, and can be automatically operably coupled with a variety of supporting technologies that can enable tissue-related processes. The system can communicate with supporting technologies upstream and downstream on a manufacturing line, enabling fully automated process control, centralized data historization, and centralized control.

38 Claims, 44 Drawing Sheets

(51) Int. Cl.

| | |
|---|---|
| *C12M 1/02* | (2006.01) |
| *C12M 1/12* | (2006.01) |
| *C12M 1/36* | (2006.01) |
| *C12N 5/071* | (2010.01) |

(52) U.S. Cl.
CPC ............ *C12M 29/10* (2013.01); *C12M 29/26* (2013.01); *C12M 39/00* (2013.01); *C12M 41/22* (2013.01); *C12M 41/48* (2013.01); *C12N 5/069* (2013.01)

(56) References Cited

U.S. PATENT DOCUMENTS

| | | | |
|---|---|---|---|
| 6,945,056 B2 | 9/2005 | Brown et al. | |
| 6,996,995 B2 | 2/2006 | Voute et al. | |
| 7,353,658 B2 | 4/2008 | Voute et al. | |
| 2011/0136225 A1* | 6/2011 | Vunjak-Novakovic | ...................... C12M 25/14 435/325 |
| 2013/0102071 A1 | 4/2013 | Pan et al. | |
| 2013/0210130 A1 | 8/2013 | Larcher et al. | |
| 2015/0093829 A1* | 4/2015 | Swanda | .................. C12M 23/58 435/293.1 |
| 2015/0289501 A1* | 10/2015 | Raredon | ................ A61K 35/42 435/284.1 |
| 2016/0145563 A1* | 5/2016 | Berteau | .................. C12M 41/48 137/15.01 |
| 2016/0252537 A1 | 9/2016 | Murali et al. | |
| 2017/0096628 A1* | 4/2017 | Bachellier | .............. C12M 37/04 |
| 2017/0175063 A1 | 6/2017 | Smith et al. | |
| 2018/0066218 A1 | 3/2018 | Koike et al. | |
| 2018/0179484 A1* | 6/2018 | Luo | ........................ C12M 41/12 |
| 2019/0219992 A1* | 7/2019 | Grimm | ............ G05B 19/41875 |
| 2021/0340486 A1* | 11/2021 | Andrews | ................ C12M 27/18 |
| 2022/0154852 A1 | 5/2022 | White et al. | |

FOREIGN PATENT DOCUMENTS

| | | |
|---|---|---|
| WO | 2005116186 | 12/2005 |
| WO | 2015071829 | 5/2015 |
| WO | 2017032829 | 3/2017 |
| WO | 2020257335 | 12/2020 |
| WO | 2021003188 | 1/2021 |
| WO | 2022159959 | 7/2022 |

OTHER PUBLICATIONS

Akhyari et al., The Quest for an Optimized Protocol for Whole-Heart Decellularization: A comparison of Three Popular and a Novel Decellularization Technique and Their Diverse Effects on Crucial Extracellular Matrix Qualities, Tissue Engineering: Part C, vol. 17, No. 9, 2011, 12 pages.

Astero, ThawSTAR® Automated Cell Thawing System, White Paper, downloaded from Internet Apr. 12, 2019, 6 pages.

Brooks, EtherNet/IP: Industrial Protocol White Paper, Institute of Electrical and Electronic Engineers, EFTA 2001, Logix/NetLinx Technology Adoption Rockwell Automation Oct. 2001, 12 pages.

Chen et al., Development of a scalable suspension culture for cardiac differentiation from human pluripotent stem cells, Elsevier—Stem Cell Research 15, 2015 pp. 365-375.

Elseberg et al., The Challenge of Human Mesenchymal Stomal Cell Expansion: Current and Prospective Answers, New Insights into Cell Culture Technology, May 10, 2017, 16 pages.

Eppendorf Dasgip® Parallel Bioreactor System by Eppendorf, SelectScience®, downloaded from the Internet Dec. 2, 2021, https://www.selectscience.net/products/eppendorf-dasgip-parallel-bioreactorsystem/?prodID=195298#tab-3, 5 pages.

Ferng et al., Acellular porcine heart matrices: whole organ decellularization with 3D-bioscaffold & vascular preservation, Journal of Clinical and Translation Research, 2017; 3(2) pp. 260-270.

Gilpin et al., Decellularization Strategies for Regenerative Medicine: From Processing Techniques to Applications, Hindawi, BioMed Research International, vol. 2017, Article ID 9831534, 13 pages.

Kitahara et al., Heterotopic transplantation of a decellularized and recellularized whole porcine heart, Interactive Cardio Vascular and Thoracic Surgery 22, 2016, pp. 571-579.

Lee et al., Inverted orientation improves decellularization of whole porcine hearts, Elsevier—Act Biomaterialia, 49, 2017, pp. 181-191.

Lelovas, A Comparative Anatomic and Physiologic Overview of the Porcine Heart, Journal of the American Association for Laboratory Animal Science, vol. 53, No. 5, Sep. 2014, pp. 432-438.

Lu et al., Repopulation of decellularized mouse heart with human induced pluripopent stem cell-derived cardiovascular pregenitor cells, Nature Communications DOI: 10.1038/ncomms337, Aug. 13, 2013, 11 pages.

Michl, et al., Evidence-based guidelines for controlling pH in mammalian live-cell culture systems, Communications Biology, 2019 2:144, 12 pages.

Momtahan et al., Automation of Pressure Control Improves Whole Porcine Heart Decellularization, Termis, Tissue Engineering: Part C, vol. 00, No. 00 Methods, Jun. 2015, 15 pages.

Ott et al., Perfusion-decellularized matrix: using nature's platform to engineer a bioartificial heart, Nature medicine, Jan. 13, 2008, 9 pages.

Place et al., Limitations of oxygen delivery to cells in culture: An underappreciated problem in basic and translational research, Elsevier, Free Radical Biology and Medicine 112, 2017, pp. 311-322.

Remlinger et al., Procedure for Decellularization of Porcine Heart by Retrograde Coronary Perfusion, Journal of Visualized Experiments, Dec. 2012, 70, e50059, 8 pages.

SARTORIUS Integrated Cell Culture Analyzer, Aug. 2021, 5 pages.

Sartorius, Ambr® 15 Cell Culture Generation 2, Advanced Microbioreactor System, Mar. 2020, 16 pages.

Science Direct, Barragán, Fermentative Production Methods, Biotransformation of Agricultural Waste and By-Products, 2016, 2 pages.

Science Direct, Clapp, et al., Upstream Processing Equipment, Biopharmaceutical Processing, 2018, 4 pages.

Science Direct, Duan et al., Bioreactor design for algae growth as a sustainable energy source, Reactor and Process Design in Sustainable Energy Technology, 2014, 2 pages.

Science Direct, Ellis, Two-and three-dimensional tissue culture bioprocessing methods for soft tissue engineering, Standardisation in Cell and Tissue Engineering, 2013, 1 page.

Science Direct, Fundamentals, The MBR Book (Second Edition), 2011, 1 page.

Science Direct, Kirkpatrick, Standardisation in Cell and Tissue Engineering, 2013, 1 page.

Science Direct, Show et al., Production of Biohydrogen from Microalgae, Biofuels from Algae, 2014, 5 pages.

Science Direct, Tandon et al., Bioreactors for Tissue Engineering, Biomaterials Science (Third) Edition, 2013, 1 page.

Science Direct, Wang et al., Handbook of Membrane Reactors: Fundamental Materials Science, Design and Optimisation, 2013, 5 pages.

Science Direct, Zhong et al., New Developments and Application in Chemical Reaction Engineering, Studies in Surface Science and Catalysis, 2006, 1 page.

Taylor et al., Decellularization of Whole Human Heart Inside a Pressurized Pouch in an Inverted Orientation, Journal of Visualized Experiments, DOI 10.3791/58123, Nov. 26, 2018, 1 page.

Taylor et al., Decellularization of Whole Human Heart Inside a Pressurized Pouch in an Inverted Orientation, Materials List, Journal of Visualized Experiments, DOI:10.3791/58123, Nov. 26, 2018, 1 page.

Taylor et al., Decellularization of Whole Human Heart Inside a Pressurized Pouch in an Inverted Orientation, Supplement, Journal of Visualized Experiments, DOI:10.3791/58123, Nov. 26, 2018, 5 pages.

Wang et al., Development of Novel Bioreactor Control Systems Based on Smart Sensors and Actuators, Frontiers in Bioengineering and Biotechnology, Feb. 4, 2020, 15 pages.

(56) References Cited

OTHER PUBLICATIONS

International Search Report and Written Opinion mailed Sep. 16, 2020 issued in PCT Patent Application No. PCT/US2020/038214, 11 pages.
International Preliminary Report on Patentability mailed Dec. 30, 2021, issued in PCT Patent Application No. PCT/US2020/038214, 7 pages.
Communication mailed Jan. 26, 2022, issued in European Patent Application No. 20736864.8, 3 pages.
International Search Report and Written Opinion mailed May 23, 2022, issued in PCT Patent Application No. PCT/US2022/070265, 12 pages.
Office Action mailed Jun. 6, 2022, issued in Chinese Patent Application No. 202220160610.8, 5 pages.
U.S. Appl. No. 29/758,774, filed Nov. 18, 2020.

* cited by examiner

Note 3: Gas mixer vent valve

SECTION C-C
SCALE 3:1

856

854

852

SECTION B-B
SCALE 3:1

854

125

123

118

102

121

116  112

139

117

143

131

152

157    155    147    151

115A

933

931

915

937

935

| Phase # | Description | Fluid | P-01 Status | P-01 Strategy | P-01 Expected Rate | P-02 Status |
|---|---|---|---|---|---|---|
| 1 | Clear blood (1) | Heparinized PBS | Pump 3L @100 mmHg | Volume/Pressure | | Control to 12-14 mmHg |
| 2 | Clear blood (2) | Heparinized PBS | Pump 15 min @100 mmHg | Time/Pressure | | Control to 12-14 mmHg |
| 3 | Clear blood (1) | Heparinized PBS | Pump 3L @100 mmHg | Volume/Pressure | | Control to 12-14 mmHg |
| 4 | Clear blood (2) | Heparinized PBS | Pump 15 min @100 mmHg | Time/Pressure | | Control to 12-14 mmHg |
| 5 | Clear blood (3) | DI Water | Pump 3L @100 mmHg | Volume/Pressure | | Control to 12-14 mmHg |
| 6 | Lyse Cells (1) | 500 mM NaCl | Pump 4 hrs @100 mmHg | Time/Pressure | | Control to 12-14 mmHg |
| 7 | Lyse Cells (2) | DI Water | Pump 3L @100 mmHg | Volume/Pressure | | Control to 12-14 mmHg |
| 8 | Remove Debris (1) | 1% SDS | Pump 3L @100 mmHg | Volume/Pressure | | Control to 12-14 mmHg |
| 9 | Remove Debris (2) | 1% SDS | Pump 3 hrs @100 mmHg | Time/Pressure | | Control to 12-14 mmHg |
| 10 | Remove Debris (3) | DI Water | Pump 3L @100 mmHg | Volume/Pressure | | Control to 12-14 mmHg |
| 11 | Remove Debris (1) | 1% SDS | Pump 3L @100 mmHg | Volume/Pressure | | Control to 12-14 mmHg |
| 12 | Remove Debris (2) | 1% SDS | Pump 3 hrs @100 mmHg | Time/Pressure | | Control to 12-14 mmHg |
| 13 | Remove Debris (3) | DI Water | Pump 3L @100 mmHg | Volume/Pressure | | Control to 12-14 mmHg |
| 14 | Remove Debris (1) | 1% SDS | Pump 3L @100 mmHg | Volume/Pressure | | Control to 12-14 mmHg |
| 15 | Remove Debris (2) | 1% SDS | Pump 3 hrs @100 mmHg | Time/Pressure | | Control to 12-14 mmHg |
| 16 | Remove Debris (3) | DI Water | Pump 3L @100 mmHg | Volume/Pressure | | Control to 12-14 mmHg |
| 17 | Remove SDS (1) | 1% Triton X-100 | Pump 3L @100 mmHg | Volume/Pressure | | Control to 12-14 mmHg |
| 18 | Remove SDS (2) | 1% Triton X-100 | Pump 3 hrs @100 mmHg | Time/Pressure | | Control to 12-14 mmHg |
| 19 | Wash | DI water | Pump 15L @100 mmHg | Volume/Pressure | | Control to 12-14 mmHg |
| 20 | Wash | 1X PBS | Pump 3L @100 mmHg | Volume/Pressure | | Control to 12-14 mmHg |

TABLE III

FIG. 18B

TABLE IV

| Valve Location: | Lower | Lower | Lower | Lower | Mid | Mid | Upper | Upper | Upper | Mid | Mid | Upper |
|---|---|---|---|---|---|---|---|---|---|---|---|---|
| Valve Function: | Inlet | Inlet | Inlet | Inlet | Inlet | Inlet | Outlet | Outlet | Outlet | Inlet | Inlet | Outlet |
| Media: | DI | PBS | Triton | SDS | Peracetic | Hypotonic | Not used | Not used | Waste | Heparin | Hypertonic | Recirc |
| Phase # | V-001 | V-002 | V-003 | V-004 | V-005 | V-006 | V-007 | V-008 | V-009 | V-010 | V-011 | V-012 |
| 1 | | | | | | | | | X | X | | |
| 2 | | | | | | | | | | X | | X |
| 3 | | | | | | | | | X | X | | |
| 4 | | | | | | | | | X | X | | X |
| 5 | X | | | | | | | | X | | | |
| 6 | | | | | | | | | X | | X | |
| 7 | X | | | | | | | | X | | | |
| 8 | | | | X | | | | | X | | | |
| 9 | | | | X | | | | | | | | X |
| 10 | X | | | | | | | | X | | | |
| 11 | | | | X | | | | | X | | | |
| 12 | | | | X | | | | | | | | X |
| 13 | X | | | | | | | | X | | | |
| 14 | | | | X | | | | | X | | | |
| 15 | | | | X | | | | | | | | X |
| 16 | X | | | | | | | | X | | | |
| 17 | | | X | | | | | | X | | | |
| 18 | | | X | | | | | | | | | X |
| 19 | X | | | | | | | | X | | | |
| 20 | | X | | | | | | | X | | | |

FIG. 18C

MODULAR, CONFIGURABLE BIOREACTOR SYSTEM FOR A MANUFACTURING LINE

CROSS REFERENCE TO RELATED APPLICATIONS

This utility patent application claims the benefit of U.S. Provisional Patent Application Ser. No. 63/139,408 filed Jan. 20, 2021, entitled System and Method for Thermal Maintenance of a Bioreactor, which is incorporated herein by reference in its entirety.

BACKGROUND

The present disclosure pertains to configurable systems, and specifically to configurable manufacturing systems. In configurable manufacturing systems, the idea is to enable plug and play components to be added to and removed from a system with little to no retooling of the system, as well as to enable robust communications to upstream and downstream equipment and technologies. Plug and play is a special concern with respect to industrial systems that accommodate operable coupling of the swappable components whose footprints, characteristics, and thermal requirements differ from component type to component type. Current systems can be improved by enabling upstream and downstream communication with other components of a manufacturing line. Examples of components of a manufacturing line for tissue processing can include, but are not limited to including, a cell thaw system, a bioreactor system, and a tissue maintenance system. Standard processes and communications among the components along the manufacturing line enable addition and removal of components, depending upon the desired output. Thus, the manufacturing line of the present teachings contemplates a variety of components, including those listed herein and others, operating simultaneously, sequentially, or in an order determined by a recipe, dynamically, and/or user-selected.

When considering the bioreactor system of the manufacturing line, results could be improved by providing automatic media changeovers, sterilization, a decellularization perfusion process, integrated electrical and mechanical stimulation, and multi-use bioreactor parts, for example. Other possibilities for improvement exist. Examples of uses for a manufacturing line for tissue processing that include the system of the present teachings, include, but are not limited to, cell expansion, decellularization, perfusion of endothelial cells, recellularization, and maturation of recellularized tissue. This list in no way limits this disclosure or the uses of the system of the present teachings.

Cell expansion is the purposeful growth of cells to create tissue or therapies for disease. Cells that can be used effectively in the cell expansion process of human mesenchymal stromal cells (hMSCs) (adult stem cells) and human-induced pluripotent stem cells (hiPCSs) (obtained by reprogramming somatic cells of human pluripotent stem cells (hPCSs)). These cell types can self-renew and differentiate into specific cell types, depending upon their potency. Bioreactors (culture vessels) can be used to enable cell expansion, especially because they can provide a 3D, agitated, scalable, homogenized environment. Types of bioreactors that could be found in a manufacturing line can include stirred-tank, fixed-bed, hollow-fiber, rotary cell, rotating bed, and rocking motion bioreactors, having disposable or durable components, or a combination. Sensors can be associated with the bioreactor and a controller to establish an operating range of temperature, acid/base level, aeration, agitation speed, and culture media flow rate. What is needed to enable repeatability in cell expansion on a manufacturing line is consistent internal control of the bioreactor system, and communication of the status and other characteristics of the bioreactor system with other manufacturing line components.

Decellularization results in the removal of living tissue from an extracellular matrix (ECM) scaffold, while retaining cell preservation and homeostasis cues in the structure of the ECM. A scaffold can be physically or chemically decellularized. Chemicals used in decellularization include surfactants like sodium dodecyl sulfate (SDS) that lyse cells by disarranging the phospholipid cell membrane, acids like peracetic acid and bases like sodium hydroxide that solubilize the cell membrane. Physical decellularization can include methods such as freezing/thawing, high hydrostatic pressure, and supercritical carbon dioxide. All decellularization processes involve a wash process. To determine if decellularization is successful, aspects of the ECM remaining after decellularization can be examined to determine if, for example, the cells were removed, genetic material has been eliminated, the protein in the matrix has been preserved, and any mechanical properties have been retained. More specifically, in some systems, the ECM after decellularization must not reach a pre-selected threshold of double-stranded DNA of a pre-selected fragment length, and have no visible nuclear material. Mechanical properties including elastic modulus and tensile strength can be required to meet certain pre-selected criteria. Success of the decellularization method can be determined by the reduction of the tissue's immunogenicity, specifically genetic materials and antigens. Insufficient reduction in immunogenicity can lead to in vivo rejection of the tissue. What is needed is a bioreactor system that includes internal controls to reach a desired decellularization results, and that includes a robust communications system that provides status of the decellularization and other characteristics to other components of the manufacturing line.

In recellularization, the scaffold is seeded with cells to form an organ. Complete organ regeneration requires that the parenechyma, vasculature, and support components must be reestablished prior to seeding the cells. Many types of cells have been considered for organ generation. For example, mesenchymal stem cells from bone marrow or adipose tissue expanded to adequate numbers can differentiate into various cell types, and scaffolds have been found to promote mesenchymal stem cell differentiation. Induced pluripotent stem cells can facilitate the use of patient-derived cells to provide a cell source for recellularization. Support cells such as fibroblasts can enhance certain types of cell function and therefore enhance recellularization. Successful seeding routes can be organ-dependent. For example, a kidney scaffold can be reseeded through the ureter or the renal artery, with the renal artery route having been shown in some studies to result in a higher cell distribution and retention than the ureter route. Recellularization requires a bioreactor control system that manages characteristics like temperature, gas, pH, and pressure. Successful recellularization results in a required number of cells of particular types to form a whole tissue or organ. What is needed is a bioreactor system that includes internal controls to reach a desired recellularization results, and that includes a robust communications system that provides status of the recellularization and other characteristics to other components of the manufacturing line.

In systems that are designed to repeatably control the growth of mammalian cells by supplying nutrients, removing waste, controlling temperature and headspace gas mixture within culture vessels, modular design can be a benefit in order to take advantage of asynchronous technological progress of systems that are required to enable cell growth. Further, such systems can provide further efficiencies by operating multiple cell culture vessel stations simultaneously. A major technological gap concerns issues related to the relative size of vessels needed for autologous and allogeneic processes with small tissues. There is a need for vessels capable of producing various quantities of cells without sacrificing the ability to monitor and control the expansion process. Efficiently using certain commercial bioreactor systems requires a large minimum volume to cover the current sensors. Harvesting various volumes of cells also becomes difficult due to the dead volumes present at the bottom of the expansion vessel, which can range from tens to hundreds of milliliters in various types of culture vessels. New disposable vessels and sensors designed for smaller working volumes are necessary to realize the goal of efficiently automating the production of autologous and allogeneic tissue engineering constructs. Likewise, scaling up to larger vessels, as large as, for example, 100 liters or larger, is needed. What is further needed is a system that can include both disposable and durable components. Disposable components such as tubing for supplying media, recirculating media, disposing of waste, seeding cells, and moving fluid and cells from one manufacturing line component to the next, as well as media reservoirs, and single use sensors could be needed. Durable components can include a system chassis, a user interface, a media refrigerator, a waste containment system, a gas management system, a pneumatic control block, and other components or sub-components on the manufacturing line, for example. Components that could be durable or disposable include, but are not limited to, expansion and maturation bioreactors.

Another technological gap concerns issues around the use of pumps and valves. In current systems, pumps and valves are installed in fixed numbers, limiting the flexibility of the system and requiring the purchase of a different system if more or fewer pumps and valves are required for a particular application. Still another technological gap involves controls of a flexibly-configured system. For example, in a system with multiple bioreactors operating simultaneously, current systems assume that each bioreactor is performing the same operation, for example, growing cells. Monitoring in these systems indicates that the cells might be growing at different rates, but the same basic control functions are required for such a parallel operation. What is needed is a system in which each bioreactor can be controlled separately while operating simultaneously. Such a system can enable simultaneous preparation of cells and scaffolding for engineering a complicated organ, and providing the results to other components on the manufacturing line. For example, a system with multiple bioreactors can simultaneously decellularize a scaffold and prepare multiple types of cells to recellularize the scaffold. Each bioreactor and its associated pumps and valves, can be subject to a custom control flow and custom gas flow, guided by monitoring of the situations with the contents of the bioreactors. For each bioreactor, various and different pumps, valves, and sensors can be activated to achieve, in this example, tissue growth and scaffold preparation simultaneously.

Current systems such as Zoo Ning, Industrial scale optical bioreactor, CN201045139Y, utility model assigned to Yantai Haishangchuanqi Biotechnology Co., LTD, granted Apr. 9, 2009, expired Sep. 19, 2014 (Ning) describe a bioreactor constructed of simple glass to accommodate large-scale industrial production. Wang et al., Development of Novel Bioreactor Control Systems Based on Smart Sensors and Actuators, Frontiers in Bioengineering and Biotechnology, 8:7, doi: 10.3389/fbioe.2020.00007, Feb. 4, 2020 (Wang), describe the latest trends in bioreactor control technology, including hierarchical structure control systems, a form of networked control system in which a set of devices and governing software are arranged in a hierarchical tree, and the links in the tree are implemented by a computer network. Wang describes an improvement of the flat organizational control system for bioreactors based on parallel distributed smart sensors and actuators as a concise solution for process control in bioreactors. Laboratory configurations such as Sartorius AMBR® 15 Cell Culture Generation 2 can be changed by the operator at both the start of and during the process. The system includes single-use vessels and an automated workstation, all installed in a biological safety cabinet. Multiple bioreactor cultures are monitored in parallel. The system includes an automated liquid handler that can provide media, feed, and reagents to the vessels, and facilitates in-line or off-line sampling. Other devices such as Eppendorf's DASGIP® Parallel Bioreactor Systems allow for advanced bioprocess control and automation. The system provides precise control of parameters, user-defined profiles, automated features, and configurable solutions to accommodate requirements of microbial, phototrophic, mammalian, and human cells, and stem cell applications. The system can control multiple durable or disposable bioreactors in parallel, maintain a desired temperature profile, control agitation, pH, and DO, and TMFC gas mixing of air, $N_2$, $O_2$, and $CO_2$.

What is needed, however, and is not currently provided, is an industrial control system with at least one integrated programmable logic controller (PLC) in a closed system bioreactor. Such a system could enable communications between the bioreactor PLC and other controllers along a manufacturing line. What is needed is a system that has integrated sensors, a system that accommodates a change in vessel size and shape, and that allows for a smaller number of MFCs than number of bioreactors. What is needed is a system that can accommodate growing one type of cell on one side of a bioreactor scaffold, another type on another side, and the ability to combine the two types of cells.

SUMMARY

The system of the present teachings overcomes the technological gaps outlined herein. The system of the present teachings efficiently automates the production of autologous and allogeneic tissue by accommodating cell culture vessels of various sizes and processes with small tissues. The vessels of the present teachings can produce various quantities of cells without sacrificing the ability to monitor and control the expansion process. The vessels include a head plate that can accommodate the tubing needs of various organ types. The vessels of the present teachings are configured to accommodate sensor placement so that the volume of cells covers the sensors. The vessels can be disposable to enable harvesting various volumes of cells, thus reducing the volume of dead cells at the bottom of the vessel. The vessels can also be durable. The vessels can be scaled down to accommodate small quantities of cells, for example, but not limited to, 0.1-31, or scaled up to larger vessels, for example, up to 10001. The system can also accommodate variable numbers of pumps and valves that can be allocated based on the particular application. The system includes at least one controller that is configured to control a variable number of valves and pumps, variable numbers and sizes of vessels, and fluids and gases associated with the desired process. As the vessels can be configured with different types of cells, tissue, and/or scaffolding, the controller is configured to control various processes executing in the vessels in parallel. The system is configured to control each culture vessel station separately while they operate simultaneously. For example, a system with multiple culture vessel stations can simultaneously decellularize a scaffold and also prepare multiple types of cells to recellularize the scaffold. Each culture vessel and its associated pumps, valves, and gas system can be subject to a custom control flow, guided by monitoring of the contents of the culture vessels. For each culture vessel, various pumps, valves, and sensors can be activated to achieve, for example, tissue growth and scaffold preparation simultaneously. The system of the present teachings includes pressure-controlled circulation flow, along with flow feedback and monitoring. Flowpaths can be changed as the system operates. Another feature of the system of the present teachings is a gas control system configured to allow for a smaller number of mass flow controllers (MFCs) than the number of culture vessels because each culture vessel is given a window of time in which to receive gas. This feature enables a reduction in gas consumption, less gas being vented, and less wasted gas than a system having a one-to-one correspondence between MFCs and culture vessels. Yet another feature is that the system can accommodate growing one type of cell on one side of a culture vessel scaffold, another type on another side, and can combine the two types of cells. Uses for the system of the present teachings can include, but are not limited to including, cell culturing, media conditioning (i.e. adjusting the temperature of the media to a desired value, and setting the pH and DO levels of the media), decellularizing and recellularizing scaffolds, generating blood, blood components, viruses for gene therapy, recombinant proteins, pharmaceuticals, vaccines, allergens, genes, antibodies, fermenting, medical compounds, cosmetics, and food, and converting raw materials into useful byproducts. Other applications are contemplated by the present teachings.

BRIEF DESCRIPTION OF THE DRAWINGS

The foregoing features of the disclosure will be more readily understood by reference to the following description, taken with reference to the accompanying drawings, in which:

FIGS. 18A-18C are schematic diagrams illustrating a way that the system of the present teachings can be used to decellularize a heart.

DETAILED DESCRIPTION

The system of the present teachings can follow a process specific to the contents of at least one culture vessel to produce a desired result in a controlled environment. The system can accommodate various sizes and shapes of culture vessels, various configurations and numbers of valves, pumps, and sensors, and various types and numbers of fluids and gasses, thus enabling a plug and play system that can produce consistent and recreatable results.

Figure 1A:
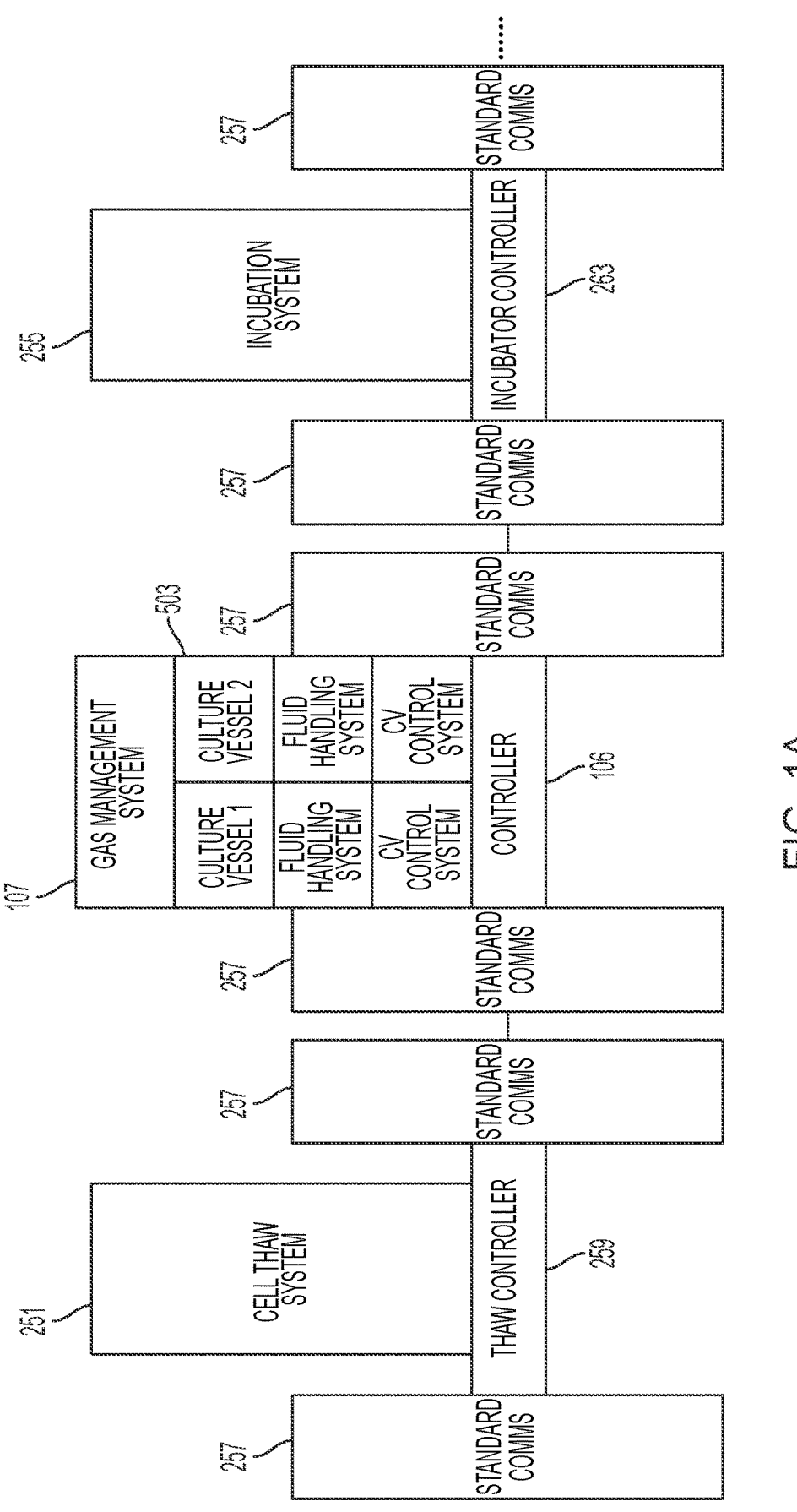
FIG. 1A is a schematic block diagram of an configurable industrial manufacturing system including the system of the present teachings.

Referring now to FIG. 1A, the system of the present teachings can be a component of an industrial control system, an example of which is shown in FIG. 1A, in which information from each component is accessible by other components of the system. Components of industrial systems have benefitted from adhering to industry agreed-upon standards such as the Ethernet/IP protocol and ANSI/ISA-88.01-1995 (ISA-88). The Ethernet/IP protocol, or Ethernet Industrial Protocol, is an industrial network protocol that allows Ethernet to be used as a control protocol. The object library and device profiles associated with Ethernet/IP enable plug-and-play interoperability among complex devices, and support real-time I/O messaging, configuration, and diagnostics over the same network. Ethernet/IP provides information and control messaging services (see Brooks, EtherNet/IP: Industrial Protocol White Paper, IEEE, EFTA 2001, October 2001). ISA-88 consists of models and terminology for structuring the production process and for developing the control of equipment. ISA-88 is organized into three models—software (procedural), hardware (physical), and changes to materials accomplished when the software is executed on the hardware (process). Each model is organized into protocol levels. Across models, the protocol levels operate cooperatively to produce the batch. For example, the procedural model includes four protocol levels—procedures, unit procedures, operations, and phase. The physical model includes two protocol levels—process cell and unit, and optionally equipment and control levels. The procedural model levels, in combination with the physical model levels, produce the levels of the process model—process, process stage, process operation, and process action. Adhering to an industrially-developed standard such as ISA-88 can increase the ease of integration with other enterprise standards such as ANSI/ISA/95. Standards such as ANSI/ISA-88 are used by the system of the present teachings to provide a consistent set of processes and terminology for producing batches of materials by subjecting quantities of input materials to an ordered set of processing activities over a finite period of time using one or more pieces of equipment. See https:// www.plcacademy.com/isa-88-s88-batch-control-explained/) The standard provides the flexibility to use the system of the present teachings as a stand-alone system or integrated with a larger system. At least one integrated programmable logic controller (PLC) in the system can communicate with other controllers along a manufacturing line. An industrial system for producing finite quantities (batches) of cells, for example, can include, for example, but not limited to, cell thaw system 251, a culture vessel system receiving the thawed cells, and incubation system 255 receiving the result from whatever process has taken place in the culture vessel system. Other components of an industrial control system are contemplated by the present disclosure. Standard communications systems 257 enable data and control sharing among components of the illustrative industrial control system, as described herein with respect to Ethernet/IP. For example, thaw controller 259 can communicate, through standard communications system 257, the status of the thaw operation to bio controller 106 so that controller 106 can schedule the process it expects to execute with respect to the thawed cells. Likewise, controller 106 can exchange its status with thaw controller 259 so that the thawed cells can be exchanged at the time when the culture vessel system is ready for them. Controller 106 can provide its status and other information about the process it is executing to incubator controller 263, and can provide its own information to controller 106. The components can be cooperatively controlled by a system control means that can monitor and command the components by tracking standard communications among the components.

Figure 1B:
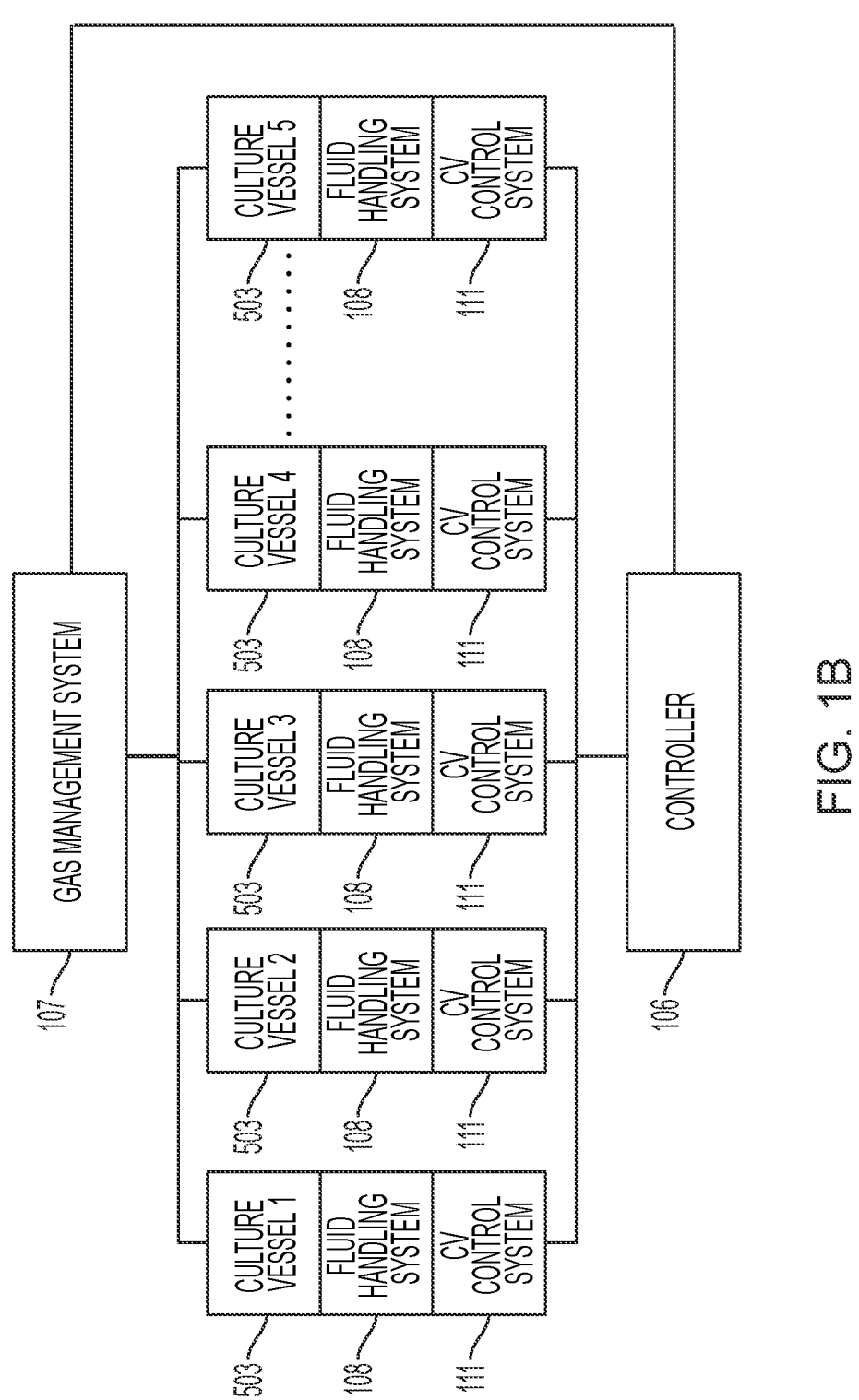
FIG. 1B is a schematic block diagram of the system of the present teachings.

Referring now to FIG. 1B, the system of the present teachings is an automated culture vessel system intended for batch production. At the physical level, the system of the present teachings can include, but is not limited to including, components such as sensors, valves, motors/encoders, pumps, culture vessels, gas management, and controllers. These components are grouped into subsystems such as, but not limited to, a fluid handling system, a culture vessel system, a gas management system, and a control system.

The control system, referred to herein interchangeably as the PLC, can be organized in protocol levels of the procedural model according to the ISA-88 standard. The protocol levels include, from lowest level in the protocol to highest, device modules, and a control module that uses device modules to create control logic, phase, and recipe (or operation). A device module establishes communication between the device and PLC 106. The equipment module is logic that accommodates faults, operating thresholds, start/stop control, any basic functions the device will carry out. The control module can interface with one or multiple devices that need to work together to carry out a function. Related to the control module, but also defined as a state that is part of a recipe, is a phase. A phase carries out a specific function. An exemplary phase involves adding a volume of liquid to the culture vessel. The phase instructions open valves, start a pump, totalize the flow until a pre-selected fluid volume is reached, stop a pump, and close valves. Exemplary phases of the present teachings include, but are not limited to, pumping media into the culture vessel, removing media, heating the contents of the culture vessel, agitating the contents of the culture vessel, harvesting cells, and recirculating media. A recipe is the combination of a multiple phases, forming a complete process.

Continuing to refer to FIG. 1B, ISA-88 states that a recipe contains five categories of information—header, equipment requirements, formula, procedure and other information. The procedure category combines the other categories, provides a multi-level hierarchy of recipe procedural elements, and contains logic. A control recipe defines the manufacture of a single batch of a specific product and reflects process control. In some configurations, the PLC can execute the recipe in conjunction with a batch server and a human-machine interface (HMI). The HMI can display the results of recipe execution to an operator, for example, and can receive modifications to the flow and configuration information from the operator. In some configurations, commercially-available applications can provide the implementation of the HMI and the batch server. For example, Rockwell's FAC-TORYTALK® batch server software can execute on a WINDOWS® server, and can drive the HMI and kick off execution of the recipe on the PLC. The PLC is able to periodically access sensor data to understand the current conditions in the culture vessel. In some configurations, the access period is, for example, around 100 ms, although other periods are contemplated by the present disclosure. Values of the sensor data can activate a manual or automatic reaction by the PLC. For example, in a configuration in which the pH/dissolved oxygen (DO) are maintained via proportional integral derivative (PID) loop and gas control, the PLC opens/closes valves, and sets a gas flow rate. Control is based on maintaining set points in the culture vessel. During a decellularization process, the pump rate changes based on the current pressure reading, with a goal of maintaining a constant pressure. The PLC takes action based on a recipe, which calls out specific phases. A phase is a sequential operation that cannot advance to the next step until the current step permissives, conditions that need to be satisfied before proceeding, are met. In some configurations, fluid handling operations are sequential operations or recipe-driven operations that involve the valves, pumps, flow sensors or level sensors. Incoming sensor data are validated and fault-checked by, for example, but not limited to, denoising, data outlier detection, missing data imputation, and data aggregation. Incoming sensor data are used in state flow or sequence to output commands to motors, pumps, and valves, to activate those devices in a certain order, for example, according to a recipe. The recipe can be dynamically changed, and the values upon which triggers in the recipe rely can also change dynamically—manually or automatically.

Continuing to refer to FIG. 1B, separate culture vessels do not share any of the same resources or equipment except the MFCs for gassing. There is separate, but identical, logic for each culture vessel, which is why they can run the same or a different process at the same time. Since constant gassing is not needed to maintain pH/DO set points in the culture vessels, each culture vessel gets a time window in which to receive gas. The process (cell maturation, expansion, decellularization, recellularization) determines the pH and DO set points. The PLC monitors the time and reads a first culture vessel's sensor data, and provides gas to the first culture vessel at a desired rate by opening a valve. At the end of the first culture vessel's time window, the first culture vessel's gas valve closes, the second culture vessel's gas valve opens and the PLC reads the sensor data from the second culture vessel and provides the desired gas mixture to the second culture vessel. Each culture vessel has its own valves, flow sensors, and pumps for fluid delivery. The PLC can execute a different recipe on each culture vessel simultaneously.

Figure 1C:
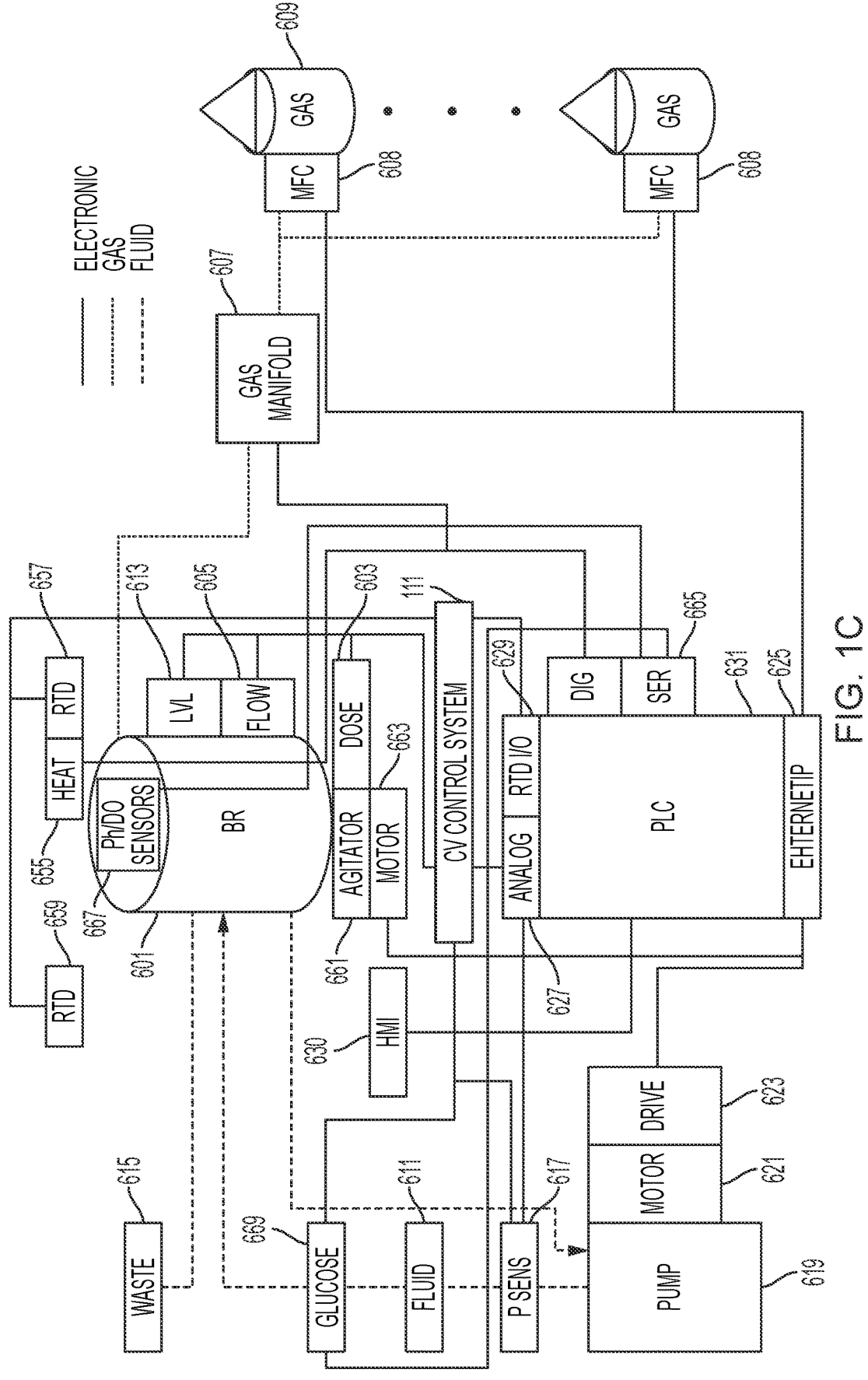
FIG. 1C is a schematic block diagram of an implementation of the system of FIG. 1.

Referring now to FIG. 1C, an exemplary implementation of the system of the present teachings includes culture vessel systems and gas management system 107, controlled by controller 106. In a configuration in which there are multiple culture vessel systems, each is equipped identically with the others, and can be used to perform a variety of tasks. Each culture vessel system includes culture vessel 503, fluid handling system 108, and culture vessel control system 111. Other configurations are contemplated by the present teachings. Culture vessel 503 includes a lidded container that is equipped with sensors, at least one fluid inlet, at least one fluid outlet, and at least one gas inlet. The lid can receive tubing appropriate to the task being performed by the culture vessel station. For example, if a heart is being recellularized, the lid can accommodate tubing that couples the descending aorta, the pulmonary artery, and the pulmonary vein with receptacles and/or nutrition sources outside of the culture vessel system. Likewise if a kidney is being recellularized, the lid can accommodate tubing that couples an artery, a vein, and the urethra with receptables and/or nutrition sources outside the culture vessel system. Fluid handling system 108 includes at least one pump, valves, and sensors that are used to move fluid through the contents of culture vessel 503. Culture vessel control system 111 maintains set points of various characteristics of the content of culture vessel 503 by monitoring sensors data associated with contents of culture vessel 503. Culture vessel control system 111 provides these set point and sensor data to controller 106 and receives commands from controller. Controller 106 accesses a recipe or other form of command structure whose execution implements the task that the culture vessel system is supposed to perform. Controller 106 can accommodate changes to the recipe, whether they be manually entered or dynamically determined. Gas management system 107 is shared by all the culture vessel systems, each receiving the gas mixture it needs to maintain homeostasis of the contents of the culture vessel. The system of the present teachings can control and monitor the reception and circulation of fluid and provision of gas to the fluid to enable a desired result with respect to the contents of the culture vessel. In an aspect, controller 106 can simultaneously control the processes executing in each of multiple culture vessel stations 503. In an aspect, controller 106 can include multiple processors that can control culture vessel station(s) 503. In an aspect, a single gas management system 107 can control the flow of a single gas. In an aspect, a single gas management system 107 can control the flow of multiple gasses. In an aspect, a single gas management system 107 can provide gas to a single culture vessel station 503. In an aspect, a single gas management system 107 can provide gas to multiple culture vessel stations 503. In an aspect, multiple gas management systems 107 can provide gas to a single culture vessel station 503. In an aspect, multiple gas management systems 107 can provide gas to multiple culture vessel stations 503. Culture vessel 503 can include, but is not limited to including, the configurable vessel assembly of the present teachings.

Continuing to refer to FIG. 1C, in an aspect, the system of the present teachings can decellularize a scaffold. In an aspect, the system of the present teachings can recellularize a scaffold. In an aspect, the system of the present teachings can provide an environment in which cells can mature and tissue can grow. In an aspect, the system of the present teachings can accommodate vessels in sizes such as, for example, but not limited to, 0.1-1000l. In an aspect, the system of the present teachings can be used to generate biopharmaceutical products such as, for example, but not limited to, vaccines, blood, blood components, allergens, genes, viruses for gene therapy, cosmetics, and proteins.

Referring again to FIG. 1B, fluid handling system 108 moves media and other fluids through the contents of culture vessel 503. The type of fluid, the pressure of the fluid, and the flow rate of the fluid are determined by a combination of factors, for example, but not limited to, a pre-selected process associated with a desired outcome, pre-selected set points for various characteristics required to produce the desired outcome, dynamic characteristics determination, and user input. In some configurations, the system accesses a recipe that dictates the operations that will produce the desired outcome. Each operation is characterized by a set of phases, or commands, that are executed to achieve a step in the process. In fluid handling system 108, one operation can include accessing the type of fluid required to achieve the step. Another can include configuring PLC 106 with set points for various characteristics such as the pH of the circulating fluid, the dissolved oxygen (DO) content of the circulating fluid, and the temperature of the circulating fluid. Yet another can include configuring at least one pump to move the fluid through culture vessel 503 and past sensors. Fluid control can be governed by flow rate or pressure. Components of fluid handling system 108 can include, but are not limited to including, in-line flow and pressure sensors, liquid level sensor(s), pumps, and pinch valves for directing flow.

Figure 1D:
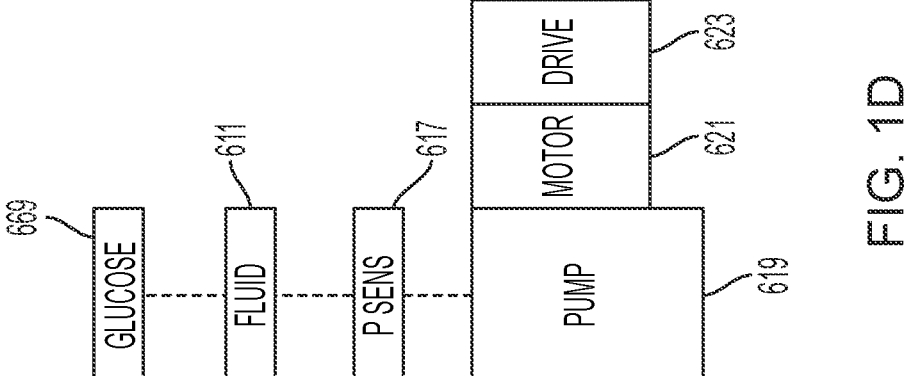
FIGS. 1D-1G are components of the implementation of FIG. 1C.

Referring now to FIG. 1D, an implementation of fluid handling system 108 (FIG. 1B) of the present teachings can include at least one fluid pump 619 per culture vessel 601 operably coupled with stepper motor 621 and motor drive 623. Motor drive 623 can communicate with PLC 631 by, for example, EthernetIP connection 625, and can support standard motor movements such as starting, stopping, direction, rate, alarming, and status of the motor. Pump 619 can circulate fluid 611 through culture vessel 601, and possibly to waste 615 through tubing that limits fluid contact to the inner bore of the tubing. Pump pressure sensor 617 can enable control of the flow rate of fluid 611 to culture vessel 601 based on an inline pressure reading upstream of the tissue within culture vessel 601. In the present configuration, if the pressure reading is outside of a pre-selected range surrounding a pre-selected set point, for example, 5 mmHg high or low, the pump speed is changed by a pre-selected percentage, either higher or lower depending upon the value of the pressure. For example the pump speed can be changed by 10%, either higher to increase pressure or lower to decrease pressure. The new pressure can be evaluated in a pre-selected amount of time, for example, 5 seconds, and the process can be repeated. If the pressure reading is within the pre-selected range, no pump speed changes are made. The pressure set point of the function is determined by the recipe. Pump pressure sensor 617 converts an outlet pressure from pump 619 to an electrical signal which variable speed pumps use to adjust the pump's speed. In some configurations, a high cut-out pressure switch can prevent pump 619 from outputting extreme pressure. Pump pressure sensor 617 can be mounted on the inlet of the pump to monitor efficiency and improve efficiency and reliability of pump 619.

Figure 1E:
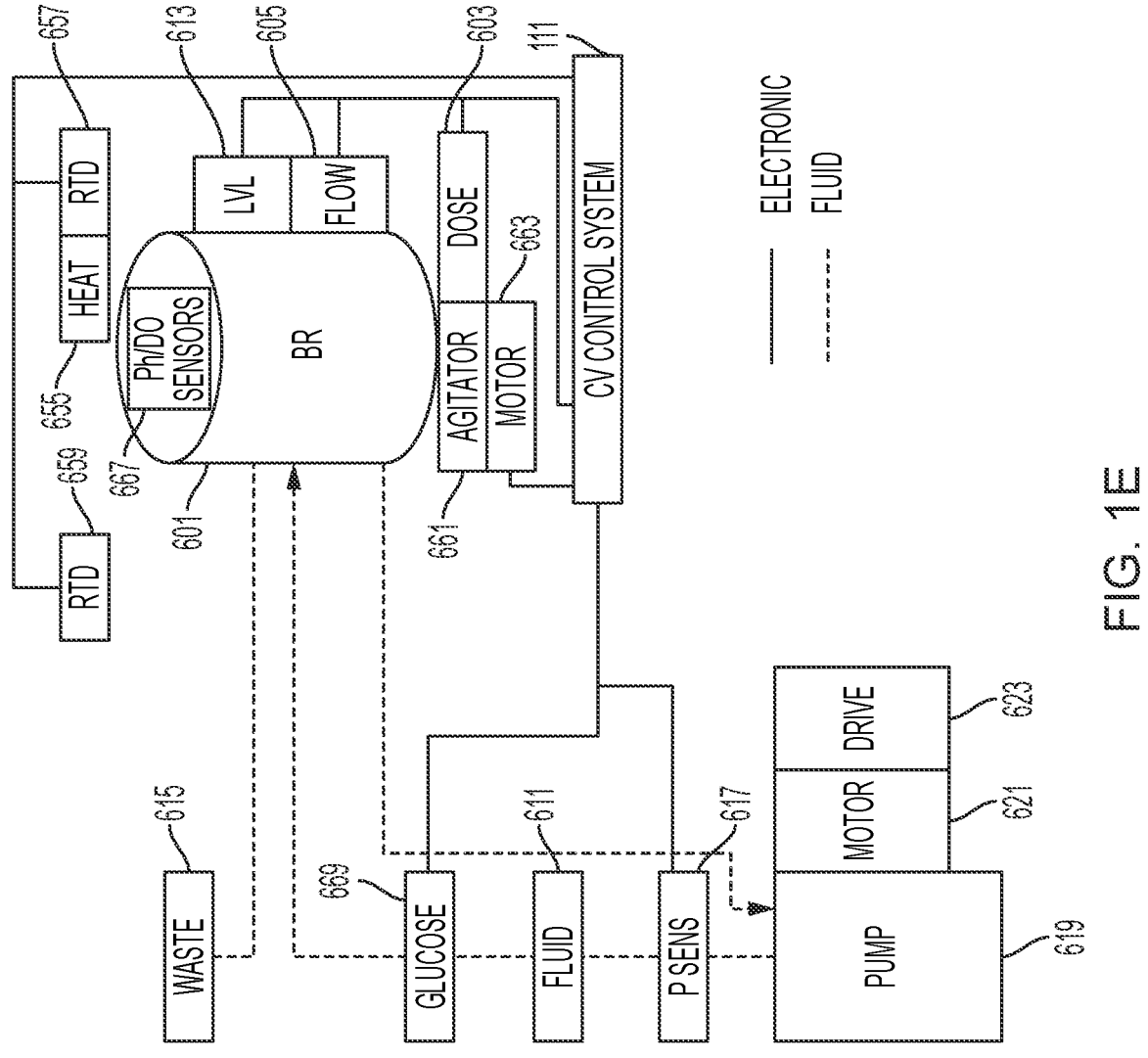

Referring now to FIG. 1E, the culture vessel, or closed culture vessel, system of the present teachings includes a configurable vessel assembly system that provides heating, location and structural support for culture vessels 601 and also provides a method for including a vessel that is sized appropriately for a given process, with minimal operations required by the user. The system of the present teachings can, for example, but not limited to, culture and produce of a variety of cell types, as well as fungal and bacterial cultures. The system can be used to produce virus and protein by way of cultured cells. The system can be configured for a variety of shapes, sizes and types of culture vessels including, but not limited to, glass and plastic vessels, durable and disposable. Exemplary types of culture vessels can include, but are not limited to including, a stirred vessel, a packed bed, a roller bottle, an oxygen-permeable culture plate, microfluidic slides, or hydrogel-based culture vessels. The culture vessel system of the present teachings includes integrated sensors that communicate with the PLC as described elsewhere herein.

Continuing to refer to FIG. 1E, the configurable vessel assembly system of the present teachings can be part of a flexible configuration to accommodate a variety of processes. A given cell expansion process may require a specific vessel volume to expand to the desired number of cells, while an alternate process may require a different vessel volume. The size of the vessel can be established to suit a desired process without altering anything but, possibly, a vessel sleeve in the flexible configuration, including heating elements, electrical connections/wiring, control logic, calibration, and positioning adjustment of the vessel. If the user wants to change the vessel size from, for example, 2 L to 0.5 L then only a simple swap of components is needed, nothing more. In some configurations, the user can simply remove a 2 L vessel sleeve and replace it with a 0.5 L vessel sleeve, each vessel sleeve having the same outside diameter. After tightening the clamps on the outside of a thermal sleeve that surrounds the vessel sleeve and ensuring the 0.5 L vessel sleeve is secure, the assembly reconfiguration is complete and ready for operation with a 0.5 L vessel. This can be done for a variety of sizes including, but not limited to, 0.5 L, 1 L, 2 L, 3 L, and up to 100 L, for example. A commercial culture vessel can be mounted to an adaptor ring of the assembly. The adapter ring mounts into a temperature control ring or thermal sleeve that has a tightening feature to ensure good thermal contact between the two components. The thermal sleeve can control an amount of thermal energy entering the vessel sleeve. The assembly can include a vessel clamp stabilizing the culture vessel within the thermal sleeve. If a different size vessel is desired, the different size vessel can be mounted into a properly sized vessel sleeve and installed into the same thermal sleeve as other sized vessels. Thus the base system remains the same regardless of the vessel size. The clamp-style heating ring can stabilize the vessel. The vessel clamp can optionally include a telescoping device. The telescoping device can accommodate various heights of various different culture vessels, and varying the height of a specific culture vessel. The assembly can optionally include a thermal break between the vessel sleeve and an environment surrounding the vessel sleeve, an electric cutoff sensing when the thermal sleeve reaches at least one pre-selected threshold temperature, the electric cutoff disabling transmission of the thermal energy to the vessel sleeve, and at least one band clamp securing the thermal sleeve to the vessel sleeve. The thermal sleeve can optionally include expansion/contraction gaps. The assembly can optionally include a stabilizing pin positionally securing the thermal sleeve to the vessel sleeve, at least one temperature control element, and a thermally-conductive material filling a space between an inner diameter of the vessel sleeve and an outer diameter of the culture vessel.

Continuing to refer to FIG. 1E, the configurable vessel assembly of the present teachings for processing cells in a controlled environment can include, but is not limited to including, a vessel sleeve surrounding at least a part of a culture vessel. The vessel sleeve can be configured to transfer thermal energy to the culture vessel. The assembly can include a thermal sleeve operably coupled with the vessel sleeve. The thermal sleeve can control an amount of thermal energy entering the vessel sleeve. The assembly can include a vessel clamp stabilizing the culture vessel within the thermal sleeve. Optionally, the assembly can include a fluid handling system moving fluid through the culture vessel, and a sensor control system operably coupled with the thermal sleeve. Culture vessel control system 111 can provide data enabling the controlling of the amount of thermal energy entering the vessel sleeve. The vessel clamp can optionally include a telescoping device. The telescoping device can accommodate various heights of various different culture vessels, and varying the height of a specific culture vessel. The assembly can optionally include a thermal break between the vessel sleeve and an environment surrounding the vessel sleeve, an electric cutoff sensing when the thermal sleeve reaches at least one pre-selected threshold temperature, the electric cutoff disabling transmission of the thermal energy to the vessel sleeve, and at least one band clamp securing the thermal sleeve to the vessel sleeve. The thermal sleeve can optionally include expansion/contraction gaps. The assembly can optionally include a stabilizing pin positionally securing the thermal sleeve to the vessel sleeve, at least one temperature control element, and a thermally-conductive material filling a space between an inner diameter of the vessel sleeve and an outer diameter of the culture vessel.

Continuing to refer to FIG. 1E, culture vessel 601 can include thermal control, agitation control, and sensors to control the characteristics of the contents of culture vessel 601 such as temperature, pH, $pO_2$, agitation, and pressure. In some processes, a temperature of 37° C. is optimal for cell maintenance. Temperatures just above or below 37° C. can affect cell viability and cell metabolism. Maintaining a desired temperature is enabled by temperature sensor 659 that reads the value of the temperature of the contents of culture vessel 601, then sends a signal to culture vessel controller system 111 to adjust the temperature is necessary through controlling heating/cooling devices if present.

Continuing to refer to FIG. 1E, level sensor 613 can monitor the liquid level in culture vessel 601. The liquid level can be used to control the amount of fluid added during a fluid transfer process, and to generate an alert if the level is too high or too low. Assuming the density of the vapor in the space not occupied by fluid 611 in culture vessel 601 is much smaller than the density of fluid 611, types of level sensors include, but are not limited to including, glass level gauge, float, displacer, bubbler, differential pressure transmitter, load cell, magnetic level gauge, capacitance transmitter, magnetostrictive level transmitter, optical, vibrating, ultrasonic, laser level transmitter, and radar level transmitter. In some configurations, the level sensor can provide a transducer output signal in the form of a 4-20 mA current loop to PLC 631 through, for example, analog input module 627.

Continuing to still further refer to FIG. 1E, as an alternative to level sensor 613, or in addition to level sensor 613, fluid flow meter 605 can measure flow, for example, in units mL/min, entering and leaving culture vessel 601. A totalizing function can be used during media transfers to calculate the total volume of transferred fluid by integrating the flow over the pump period. Categories of fluid flow meters include, but are not limited to, differential pressure, velocity, positive displacement, mass flow, and open channel. Differential pressure flow meters include orifice plates, venturi tubes, flow nozzles, and variable area rotameters. Velocity flow meters include pitot tubes, calorimetric flow meters, turbine flowmeters, vortex flow meters, electromagnetic flow meters, ultrasonic Doppler flowmeters, and time of flight flowmeter. Positive displacement flow meters can use reciprocating piston meters, nutating disk meters, and rotary vane meters. Mass flow meters include thermal flowmeters and Coriolis flowmeters. Either level sensor 613 or flow meter 605 can support dose control 603 by calculating the amount of fluid removed from or added to culture vessel 601. Dose control 603 can track the volume added and stop the addition of more fluid when a desired set point is reached. Dosing includes the ability to start/stop pumps, report under or over tolerances, alert and report the status of the delivery, possibly under pre-selected circumstances. Dosing devices fall into two main categories—gravimetric and volumetric. The choice of dosing device is based on the flow capacity of the fluid and the desired flow rate of the fluid. Dosing can be automatic, programmable, or continuous, and can be controlled by a dosing valve, for example. In some configurations, dose control 603 can be accomplished by adding instructions to level sensor 613 or flow meter 605 processing.

Continuing to refer to FIG. 1E, in some configurations, the system can include thermal control. In one arrangement, the system can include active heating and passive cooling. At least one temperature control mechanism can reside in the vessel system itself, at least one temperature sensor can reside external to the vessel to sense the temperature of the temperature control mechanism, and at least one temperature sensor can reside internal to the vessel to sense the temperature of the contents of the vessel. In some configurations, a desired temperature for the contents of the culture vessel is in the range of 34-39° C. In some configurations, a temperature threshold can include a temperature of 65° C. of the contents of the culture vessel. In some configurations, temperature control can be done with cascading PID loops, the inner loop controlling the temperature control mechanism and the outer loop controlling the temperature of the contents of the vessel. In some configurations, the temperature control mechanism can be powered by 110V. In such a configuration, a solid state relay can be used so that a 24V output card can pulse wave modulate the temperature control mechanism. Thermal control to a set point in the present teachings is achieved actively and passively. In some configurations, warming of the contents of the culture vessel is achieved actively, while cooling of the contents is achieved passively. Other configurations are contemplated by the present teachings, for example, cooling actively and warming passively, and active cooling and warming. In some configurations, the set point is a pre-selected value such as, for example, but not limited to, 37° C. In some configurations, warming can be limited to a pre-selected temperature, for example, 40° C. Sensors report the temperature of the contents of culture vessel 631 to culture vessel control system 111, and those sensor data trigger thermal control. In some configurations, temperature probe 659 is mounted to the head plate of culture vessel 601. Temperature probe 659 reads the temperature of the fluid in culture vessel 601. Heater RTD 657 is mounted to heater 655 which heats the fluid in culture vessel 601. Data from sensor RTD 659 and heater RTD 657 are received by PLC 631 through culture vessel control system 111 via RTD I/O card 629 designed to receive such data. In some configurations, the control of temperature is executed by cascading PID loops, the inner loop controlling the temperature (PWM) of heater 655 and the outer controlling the temperature of the contents of culture vessel 601. The output of the PID drives the power input to heater 655. Other methods of thermal control are contemplated by the present disclosure. For example, digital temperature sensors or silicon-based linear thermistors can be used to measure the temperature of the sensor and the contents of culture vessel 601.

Continuing to refer to FIG. 1E, culture vessel 601 can include tissue that requires movement for proper growth. For example, the contents of culture vessel 601 might need agitation to improve gas perfusion and possibly thermal control, depending upon the specific process and desired outcome. Other reasons for agitation of the contents of culture vessel 601 can include producing uniform dispersion of gas bubbles, producing small gas bubbles, maximizing retention time of gas in the fluid by driving gas bubbles to the bottom of the culture vessel, reincorporating nutrients from the top of the culture vessel back into the contents of culture vessel 601, and providing uniform nutrient and temperature profiles throughout the contents. Agitation devices include mechanical stirring devices driven by brushed or brushless DC motors 663, for example. Mechanical stirring devices are categorized by the flow direction in which the fluid is mixed—for example, axial, radial, mixed, and distributed flow—and can include propellers and impellers, for example. Propeller dimension and pitch are features that are selected based upon the application. Exemplary impellers include pitch-blade (for axial flow), Rushton (for radial flow), angled pitch-blade (mixed flow), and helical (distributed flow). In some configurations, agitator 661 can include a marine propeller attached to a shaft coupled to stepper motor 663, the combination being used to support an application such as a cell process. In some configurations, PLC 631 controls motor 663 and monitors its status by using commands transmitted and data received through a communications medium and protocol such as, but not limited to, EthernetIP 625. The speed and direction of the propeller are selected based on the application.

Continuing to still further refer to FIG. 1E, the success of applications using culture vessel 601 can rely on monitoring of various characteristics of the system and the contents of culture vessel 601. As described herein, sensors can be positioned advantageously to measure aspects of the ongoing process. For example, turbidity, pH, DO, glucose, and lactate levels can be measured by inline sensors 669 providing data to culture vessel control system 111. Such sensors can be invasive, minimally invasive, or non-invasive. Data from the sensors can be provided from culture vessel control system 111 to PLC 631 through, for example, but not limited to, a serial connection 665 (FIG. 1C), a USB connection (not shown), an EthernetIP connection 625 (FIG. 1C), or wirelessly. In some configurations, glucose and lactate levels can be gathered as the fluid circulates through the system's tubing and culture vessel 601.

Continuing to refer to FIG. 1E, the configurable vessel assembly system of the present teachings can be part of a flexible configuration to accommodate a specific cell culture process. A given expansion process may require a specific vessel volume to expand to the desired number of cells, while an alternate process may require a different vessel volume. The size of culture vessel 601 can be established to suit a desired process without altering anything but, possibly, a vessel sleeve in the flexible configuration. Heating elements, electrical connections/wiring, control logic, calibration, and positioning adjustment of culture vessel 601 can remain the same across changes in the physical size of culture vessel 601. If the user wants to change the vessel size from, for example, 2 L to 0.5 L then only a simple swap of components is needed, nothing more. In some configurations, the user can simply remove a 2 L vessel sleeve and replace it with a 0.5 L vessel sleeve and culture vessel 601, each vessel sleeve having the same outside diameter. After tightening the clamps on the outside of a thermal sleeve that surrounds the vessel sleeve and ensuring the 0.5 L vessel sleeve is secure, the assembly reconfiguration is complete and ready for operation with a 0.5 L vessel. This can be done for a variety of sizes including, but not limited to, 0.5 L, 1 L, 2 L, 3 L, and up to 100 L, for example. A commercial culture vessel can be mounted to an adaptor ring of the assembly. The adapter ring mounts into a temperature control ring that has a tightening feature to ensure good thermal contact between the two components. If a different size vessel is desired, the different size vessel can be mounted into a properly sized vessel sleeve and installed into the same thermal sleeve as other sized vessels. Thus the base system remains the same regardless of the vessel size. The clamp-style heating ring can stabilize the vessel.

Figure 1F:
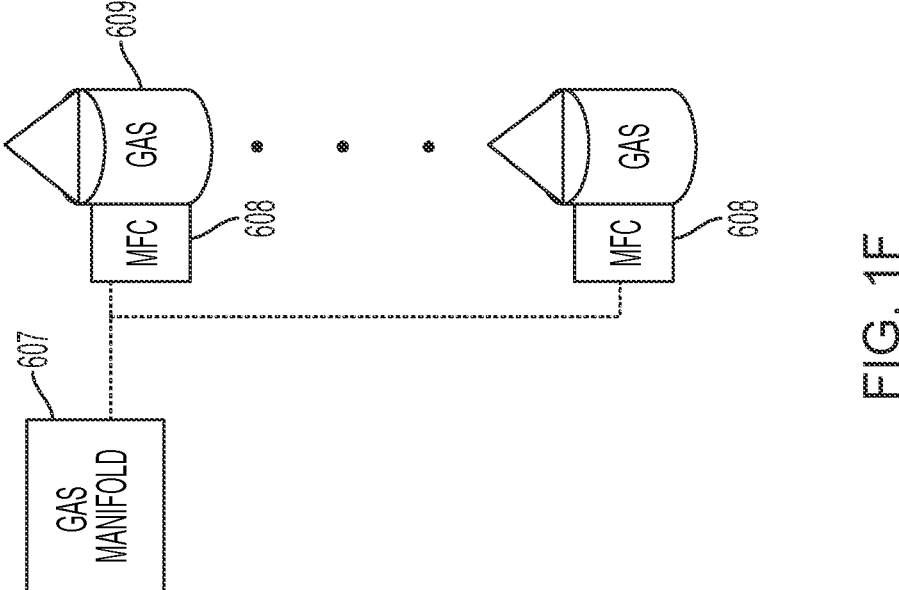

Referring now to FIG. 1F, gas management system 107 (FIG. 1B) can include gas supply 609 for each mass flow controller (MFC) 608 or functionally-equivalent device that combines a mass flow sensor and a control valve, and controls the flow rate of a gas to a desired amount without being affected by use conditions or changes in gas pressure. MFC 608 can be analog or digital, based on the numbers of types of gases being controlled. Gas supply 609 can include one or several types of gas, the selected type(s) being determined by the desired outcome from the process enabled by the system of the present teachings. Gas management system 107 (FIG. 1B) can include gas manifold 607 receiving gas from all the selected gas supplies and supplying a single gas stream to the culture vessel whose turn it is to receive selected gas(es). PLC 631 (FIG. 1C) selects the type(s) of gas to provide to culture vessels 101 (FIG. 1B) (also referred to herein as bioreactors) to achieve a gas balance that will enable the desired outcome. The system can include a plurality of MFCs 608 and associated gas supplies, but not necessarily the same number of MFCs 608 and gas supplies as the number of culture vessel stations 601 (FIG. 1C). Gas management system 107 (FIG. 1B), as described elsewhere herein, manages gas flow from the available MFCs 608/gas supply 609 to fulfill the needs of the complement of culture vessels 601 (FIG. 1C), regardless of the numbers of each component. In as aspect, MFC 608 is used to measure the total mass flow rate of the gas flowing through a closed conduit. In an aspect, gas management system 107 (FIG. 1B) can include pressure regulators and filters associated with various types of gas to prepare the gas flow for MFCs 608. In an aspect, compressed air can be subjected to a combination filter, possibly filtering particles and various types of gasses from the compressed air stream. The present teachings contemplate combination and other types of filters for all types of gas being supplied to the system. In an aspect, oxygen, nitrogen, and carbon dioxide are provided to the culture vessel in various quantities dictated by PLC 631 (FIG. 1C). In an aspect, gas management system 107 (FIG. 1B) can include gas manifolds with automatic switch-over, ensuring a continuous gas supply. The switch-over can be enabled mechanically or pneumatically and can alert the system when the switch-over has occurred so that a new gas supply can be connected. The system can include gas mixer blocks to provide a mixture of available gasses to culture vessel 601 (FIG. 1C). PLC 631 (FIG. 1C) accesses and processes directions to achieve the desired outcome from sources such as, but not limited to, recipes, user input, and sensor input.

Figure 1G:
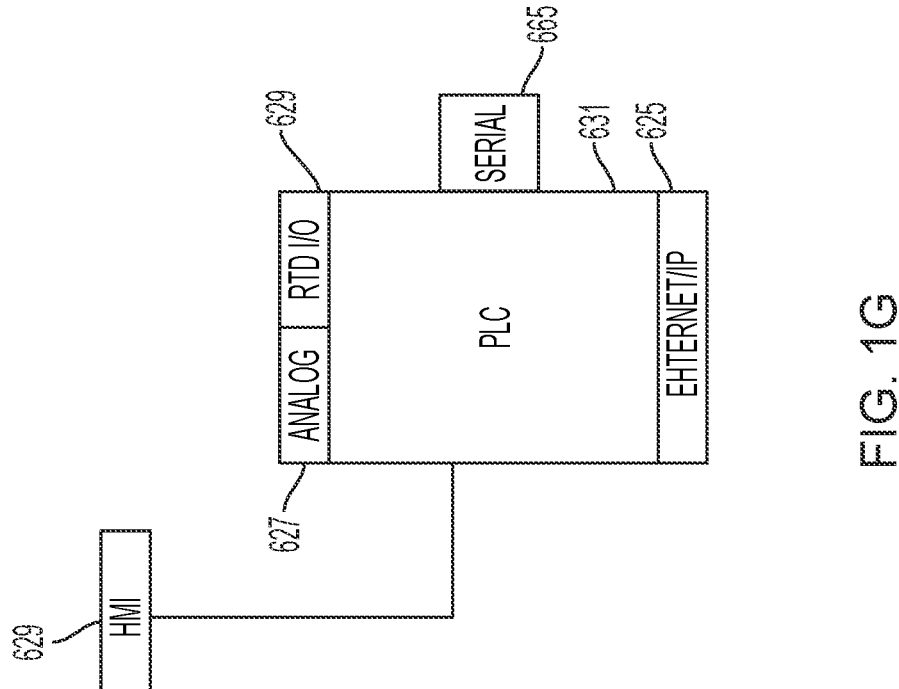

Referring now to FIG. 1G, sensors, positioned throughout the system of the present teachings, can provide analog and digital inputs/outputs that can arrive at PLC 631 through serial, parallel, or communications ports. Input/output (I/O) from the sensors can be enabled by commercially-available or custom I/O cards that provide an interface to PLC 631. The I/O cards can be connected to PLC 631 via a backplane, and can be configurable by PLC 631. I/O can also be enabled by communications cards such as EthernetIP card 625 enabling the use of communications protocols. Such device communications are routed through an Ethernet switch which is connected to a port of PLC 631. In some configurations, PLC 631 is directly wired to blocks of I/O cards and connectors. In some configurations, the electrical signals can include, but are not limited to including, 4-10 mA current loop (analog), RS-485 (serial) or 0-24V (digital). In some configurations, Ethernet connections use an RJ45 connector, and serial connections use a DB-9 connector. Depending upon the sensor, PLC 631 can enable configuration of, for example, scaling and data transmit/receive protocols. PLC 631 includes code to build a control loop around the sensor based on the desired use of the system. The sensor can be passive, or can control, for example, a pump based on pressure. Sensors can detect, for example, but not limited to, temperature of the tissue, pressure of the fluid, temperature of the fluid, and characteristics of the fluid. Sensors can be mounted throughout the system, for example, temperature sensors associated with bioreactor 601 (FIG. 1C) and fluid 611 (FIG. 1C), and fluid pressure sensors throughout the system. Sensors can provide data to PLC 631 (FIG. 1C) and possibly receive commands from PLC 631 (FIG. 1C) either wired or wirelessly, both secured from outside or man-in-the-middle interference. Some sensors can be disposable, configured to be in contact with fluid 611 (FIG. 1C), while others can be durable, configured to read data contact-free. Spot sensors can be mounted on the outside of bioreactor 601 (FIG. 1C), for example. In some configurations, non-contact fluid pressure sensor 617 (FIG. 1C) can be mounted in-line anywhere, for example, but not limited to, by luer lock ends, on tubing used for routing fluid 611 (FIG. 1C). In some configurations, sensors communicating with PLC 631 (FIG. 1C) can sense 0-60 psi along the fluid path. Signals from the sensors such as, for example, but not limited to, 4-20 mA current loop, analog voltage, or digital voltage, can be communicated from the sensors to PLC 631 (FIG. 1C) through, for example, analog input module 627.

Figure 2A:
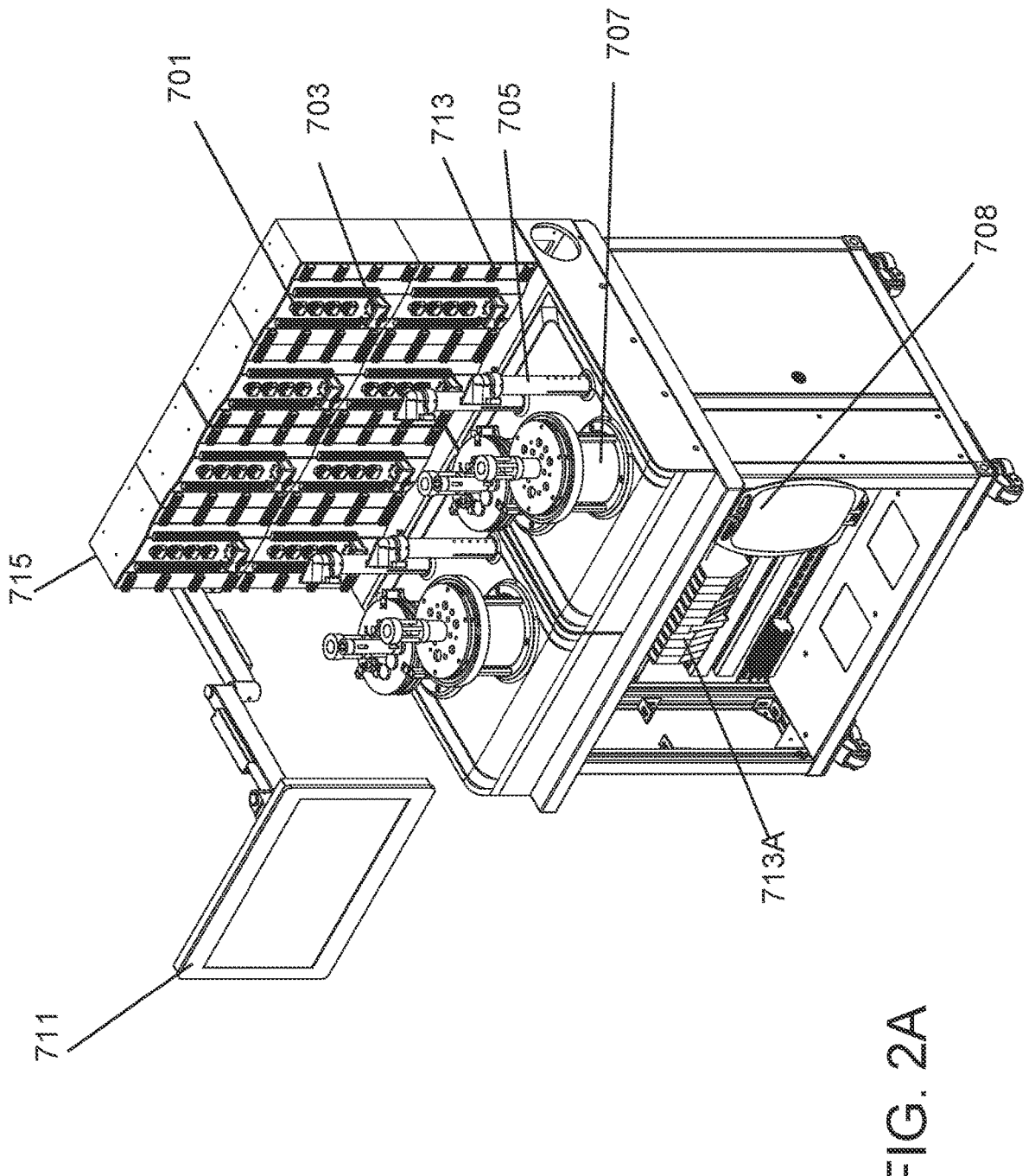
FIG. 2A is a perspective view of an implementation of the apparatus of the system of the present teachings.
Figure 2B:
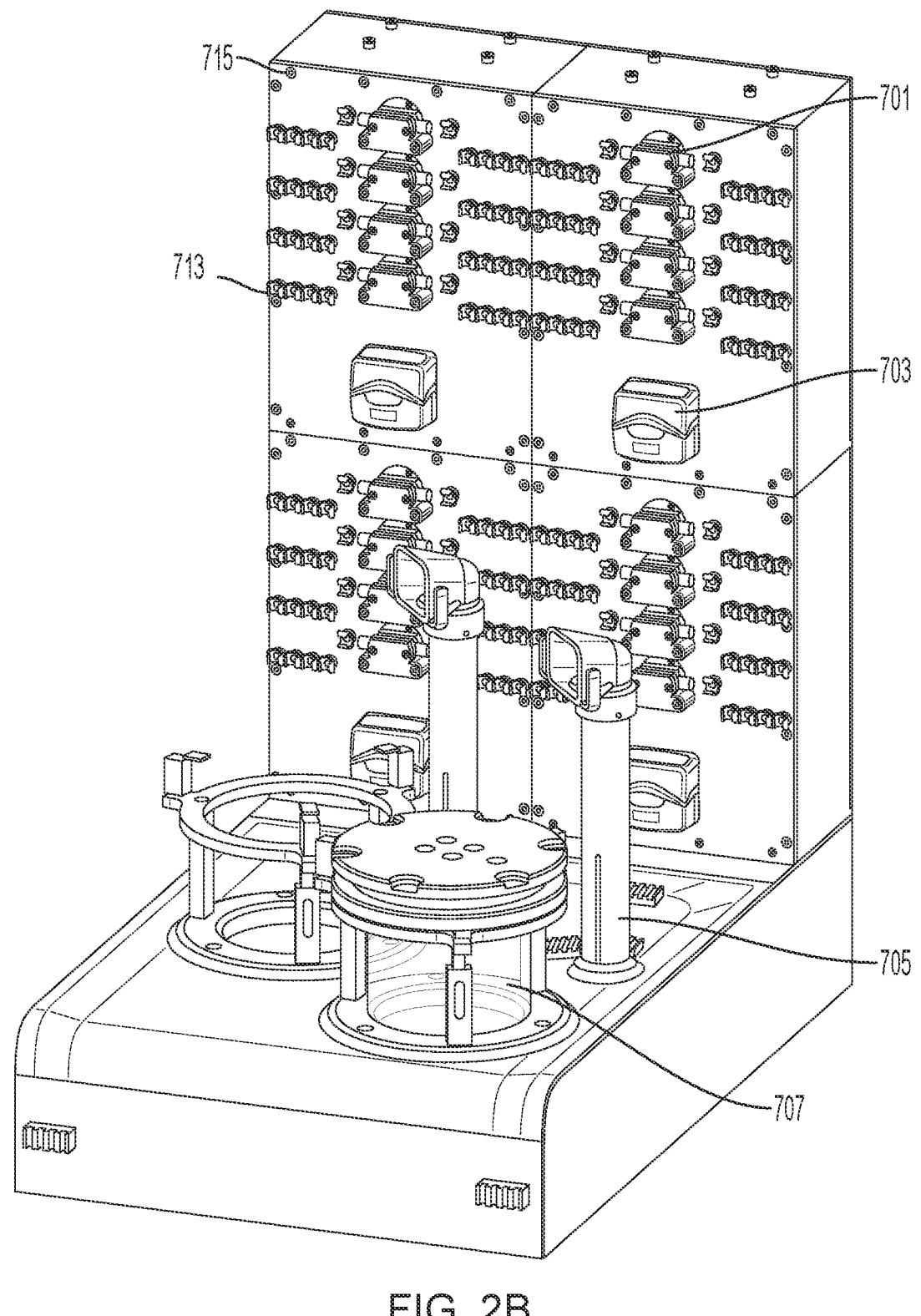
FIGS. 2B and 2C are perspective views of components of the implementation of FIG. 2A.
Figure 2C:
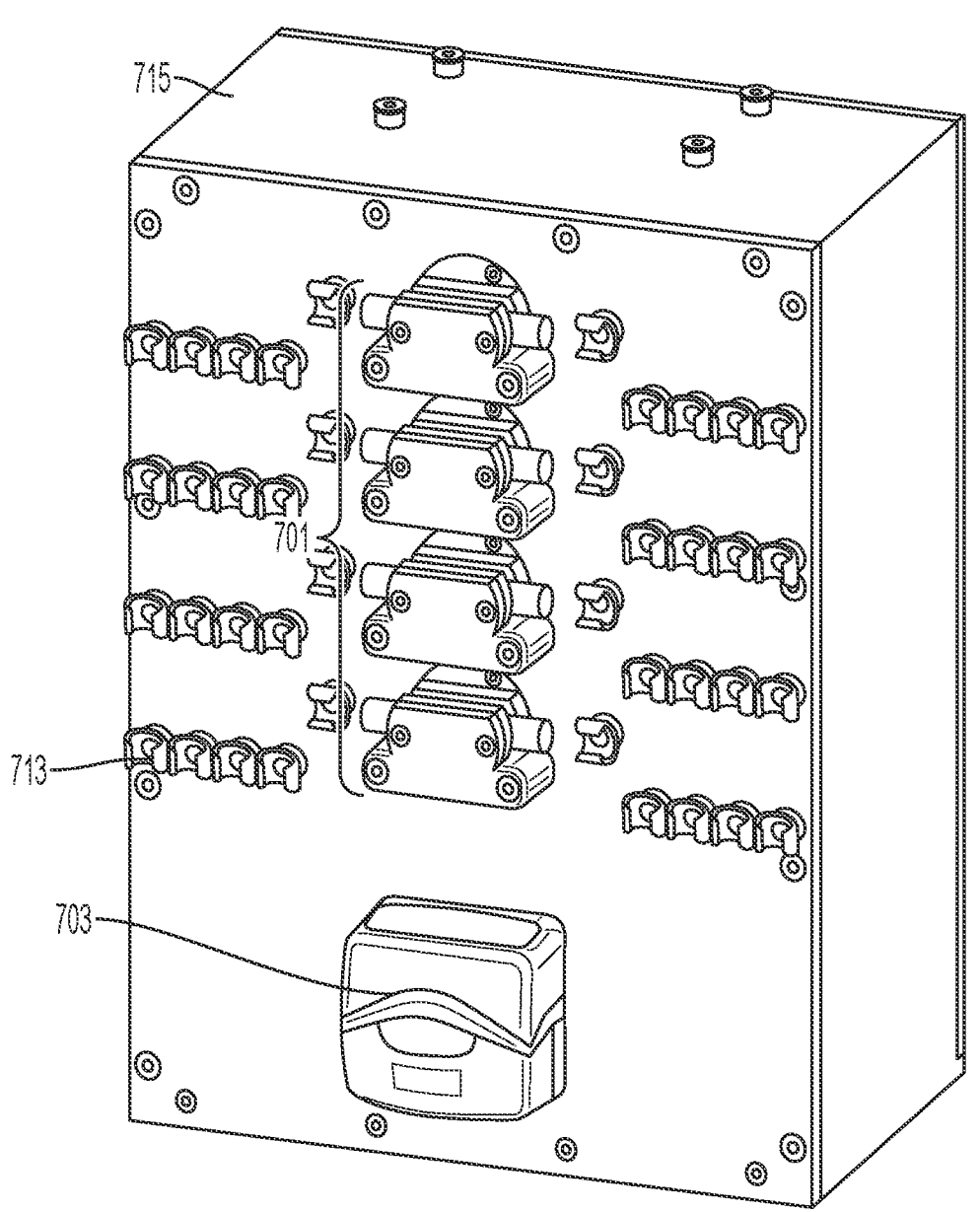

Referring now to FIGS. 2A-2C, an implementation of the hardware of the system of the present teachings is shown. Four culture vessel implementations 707 are shown. Also shown are implementations of elements of fluid handling system 108 (FIG. 1B) including fluid delivery enclosures 715 associated with culture vessel implementations 707 as indicated in FIGS. 1B and 1E. Specifically, fluid delivery enclosures (FDEs) 715 include valves 701, pumps 703, and tube guides 713. Fluid flow lines are shown elsewhere herein. Also shown are cable/sleeve snorkels 705 which are described more fully at least in U.S. patent application Ser. No. 29/758,774, White et al., Cable/Tube Sleeve and Snorkel, filed Nov. 18, 2020, and U.S. patent application Ser. No. 17/522,003, White et al., Cable/Tube Sleeve and Snorkel, filed Nov. 9, 2021, both incorporated by reference. Connector banks 713A are shown. Electronic connections between sensors and the PLC are routed through connector banks 713A. Waste collector 708 is shown, as well as human-machine interface display 711. In the present implementation, the culture station is moveable for positioning along an assembly line. A clean room is not required because there is substantially no exposure of the contents of culture vessel 707 or its associated fluids and inner tubing to the environment. Each bioreactor channel, i.e. culture vessel assembly 707, valves 701, and pump 703, can be configured differently based on the desired outcome. In some configurations, FDEs are mechanically stackable and fit together with an interlocking plate and latch. Each bioreactor channel can be associated with a pre-selected number of FDEs, and can each have a unique configuration. Each FDE can include a number of pumps 703, valves 701, and tube routing guides 713. In some configurations, the system of the present teachings can accommodate multiple pump sizes and fluid valves. The sizes and numbers of valves and pumps can be mixed and matched based on the desired outcome.

Figure 3A:
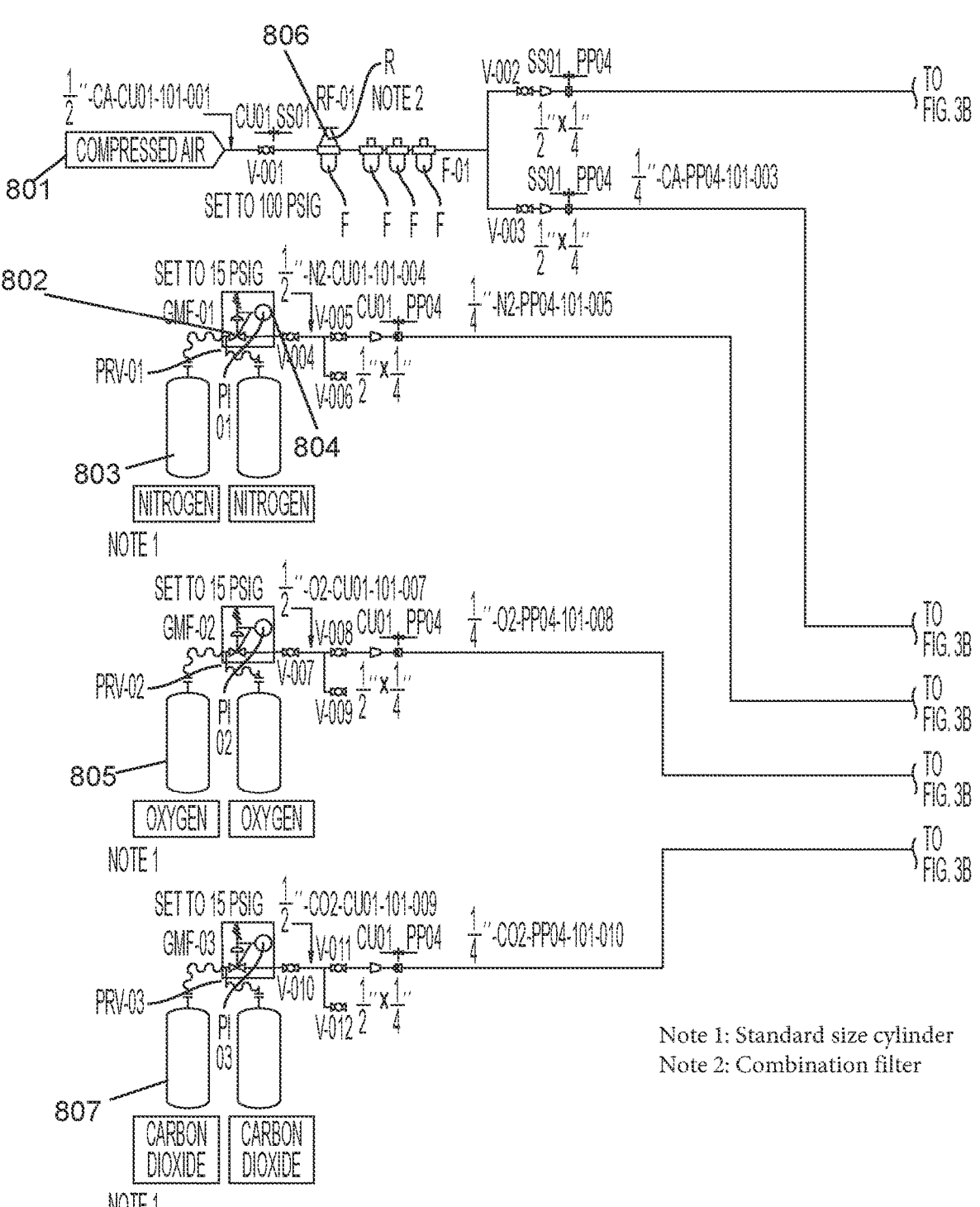
FIGS. 3A-3E are schematic diagrams of an implementation of the present teachings including a downstream recirculation system.
Figure 3B:
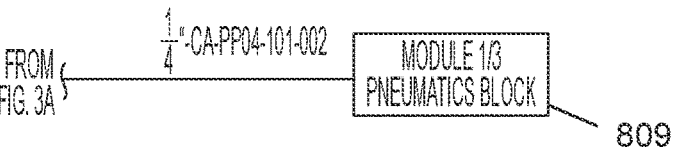
Figure 3B:
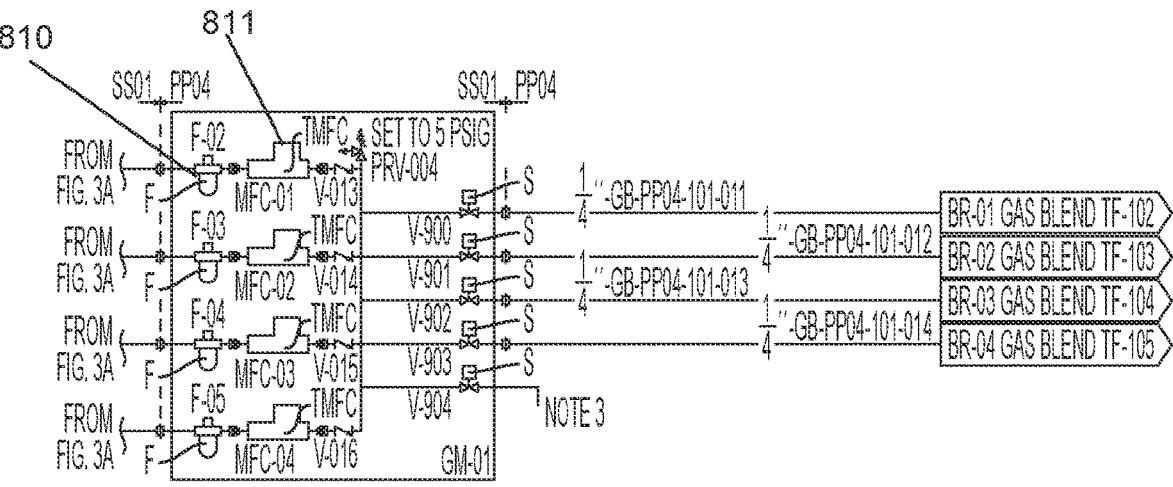
Figure 3C:
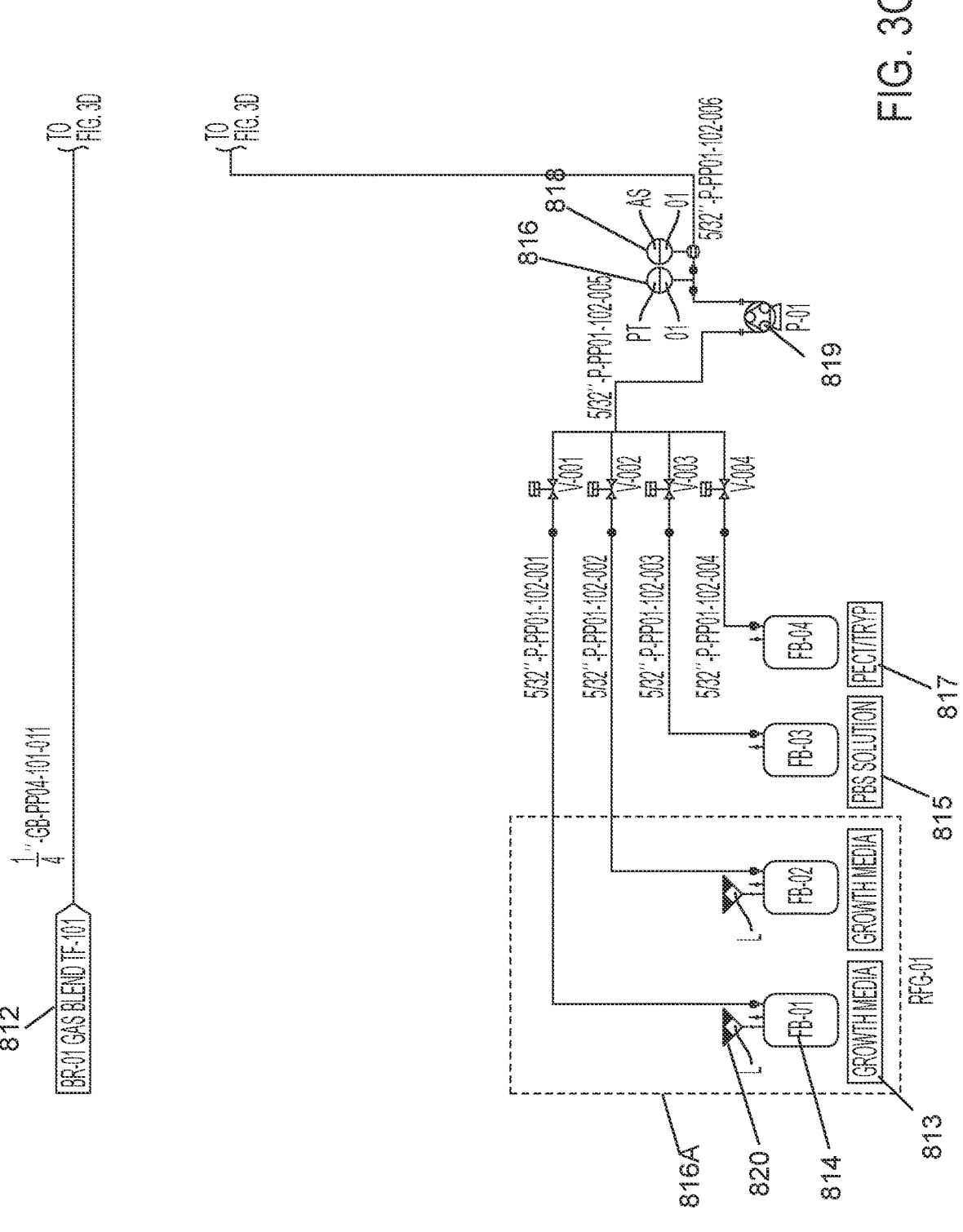
Figure 3D:
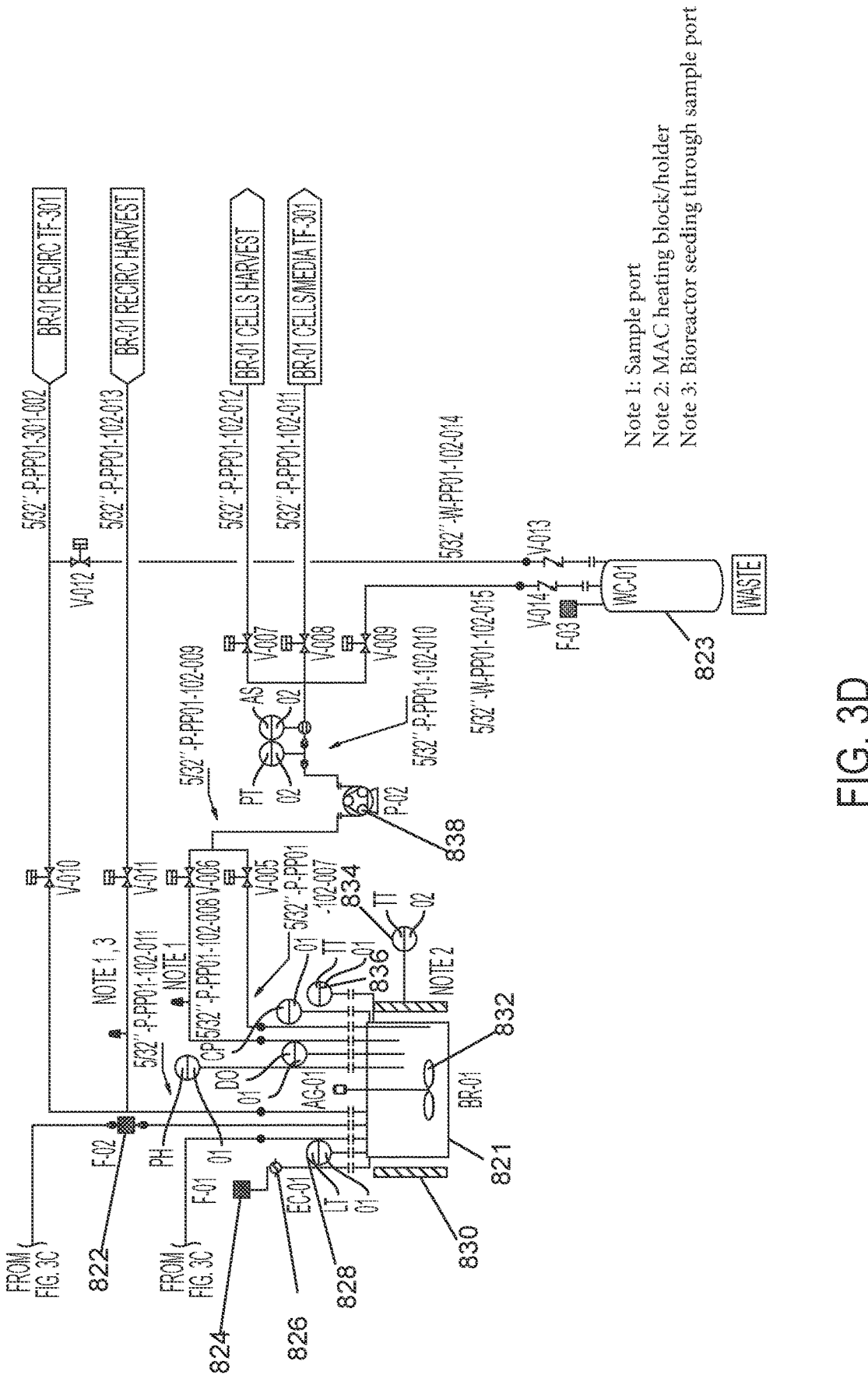

Referring now to FIGS. 3A-3E, a schematic diagram of an exemplary implementation of fluid and gas lines and components of the system of the present teachings used for cell maturation is shown. FIGS. 3A-3B show components of the gas management system described elsewhere herein. In this implementation, compressed air 801 (FIG. 3A) is routed through air filters, such as biological filters, and regulators 806 (FIG. 3A) to pneumatics block 809 (FIG. 3B). Nitrogen 803 (FIG. 3A), oxygen 805 (FIG. 3A), and carbon dioxide 807 (FIG. 3A) are routed through pressure valves 802 (FIG. 3A) and pressure regulators 804 (FIG. 3A) to thermal MFCs 811 (FIG. 3B), through filter 810 (FIG. 3B). MFCs 811 (FIG. 3B) are commanded (by the controller) to supply gas volumes that will produce the correct gas mixture 812 (FIG. 3C) for the specific activity happening in bioreactor 821 (FIG. 3D).

Referring now to FIGS. 3C-3D, shown are components of the fluid management system described elsewhere herein. FIG. 3C shows fluid source provision and pumping components. In some configurations, growth media 813 (FIG. 3C), buffer solution 815 (FIG. 3C), and trypsin 817 (FIG. 3C) are possible fluids that can be selectively pumped by pump 819 (FIG. 3C) into bioreactor 821 (FIG. 3D). In the present example, containers 814 (FIG. 3C) are hung from load sensors 820 (FIG. 3C) that can measure the volume of delivered fluid as the fluid, such as, for example, growth media 813 (FIG. 3C), is being delivered. The amount of fluid desired to be delivered can be controlled by use of the data provided by load sensor 820 (FIG. 3C) to the controller. Exemplarily, the quality of growth media 813 (FIG. 3C) is maintained by refrigerator 816A (FIG. 3C). Note that the delivered volume of both buffer solution 815 (FIG. 3C) and trypsin 817 (FIG. 3C) can be measured, for example, by load sensors 820 (FIG. 3C) as described herein. Fluids provided from the sources are pumped by pump 819 (FIG. 3C), controlled by the controller. Pump 819 (FIG. 3C) can include, for example, a contactless pump providing a gentle pumping action to avoid hemolysis, while having a high-suction lift. Such a pump can pump slurries, is reversible, and can provide accurate dosing. Measurements of the fluid pressure and air in the fluid are taken by, for example, but not limited to, inline pressure transducer 816 (FIG. 3C) and inline bubble sensor 818 (FIG. 3C) and provided to the controller for monitoring and future control of pump 819 (FIG. 3C).

Figure 3E:
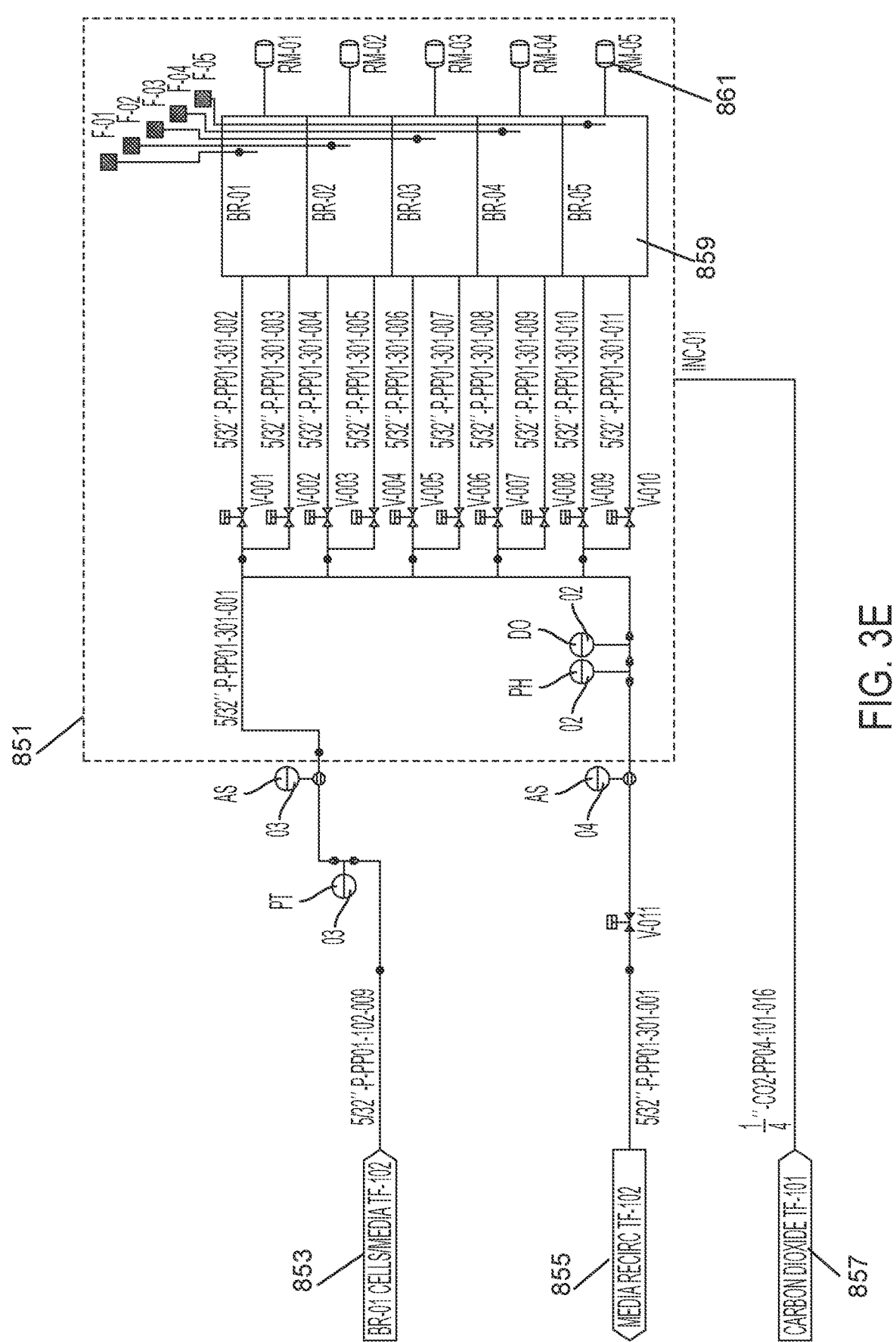

Referring now to FIG. 3D, gas and fluids are provided to bioreactor 821, and pumped from there to provide the product of the cell maturation process to fulfill a need farther down a production line. For example, shown in FIGS. 3D-3E is a configuration that can provide recirculation to enable incubation. The gas blend provided as shown in FIG. 3B is filtered by gas filter 822 (FIG. 3D), removing viruses and microorganisms from the gas blend as it proceeds to bioreactor 821 (FIG. 3D). Filtering can be accomplished by, for example, but not limited to, filters sized for the unwanted particulates, inertial separators, or electrostatic separation technologies, or a combination. Fluids are also provided to bioreactor 821. As they are added, bioreactor 821 is vented to the atmosphere, for example. As the escaping air leaves bioreacter 821, it is cooled by exhaust conditioner 826 so that fluid is condensed. The configuration of the system is such that gravity pulls the condensate back into bioreactor 821 (FIG. 3D), so that only air is vented to the atmosphere. In this way, filter 824 remains dry and allows continuous flow of air, and in addition, the culture vessel remains hydrated. Exemplary cooler 828 (FIG. 3D) can include, but is not limited to including, a peltier device. Filter 824 (FIG. 3D), through which the vented air must pass, is used to prevent contaminates from entering bioreactor 821 from the atmosphere. Thus filter 824 (FIG. 3D) can be configured to remove contaminants expected to be in the environment of bioreactor 821 (FIG. 3D), and also to protect the environment from contamination. For example, in some configurations, contaminants as small as 0.2 microns can be removed. Exemplary filters can be constructed from polypropylene and PTFE, for example, and can allow pressure to equalize within the system with the external atmospheric pressure. Such filters can be bidirectional, hydrophobic, and autoclavable, for example. The level of the fluid in bioreactor 821 (FIG. 3D) can be measured and provided to the controller to monitor the operation of the system, as described elsewhere herein. Characteristics of the contents of bioreactor 821 (FIG. 3D) can be measured, such as, for example, but not limited to, pH and DO, sensors which are shown in FIG. 3D.

Continuing to refer to FIG. 3D, the temperature of the contents of bioreactor 821 (FIG. 3D) can be controlled by a combination of thermal maintenance device 830, bioreactor thermal sensor 834 (FIG. 3D), bioreactor contents thermal sensor 836 (FIG. 3D), and the controller to which these data are routed. Depending upon the desired process, the reaction within the contents of bioreactor 821 (FIG. 3D) may endothermic, exothermic, or static. Thus, the thermal maintenance device 830 (FIG. 3D) must be capable of raising or lowering the temperature of the contents, or maintaining a static thermal situation. Thermal maintenance device 830 (FIG. 3D) can take the form of a heat exchanger in a coil, a heating blanket, or a jacket recirculation system, for example. Bioreactor thermal sensor 834 (FIG. 3D) can, in conjunction with bioreactor contents thermal sensor 836 (FIG. 3D), provide the data needed by the controller to provide thermal control to the contents.

Figure 3F:
FIGS. 3F and 3G are perspective drawings of the impeller cone of the present teachings.
Figure 3G:
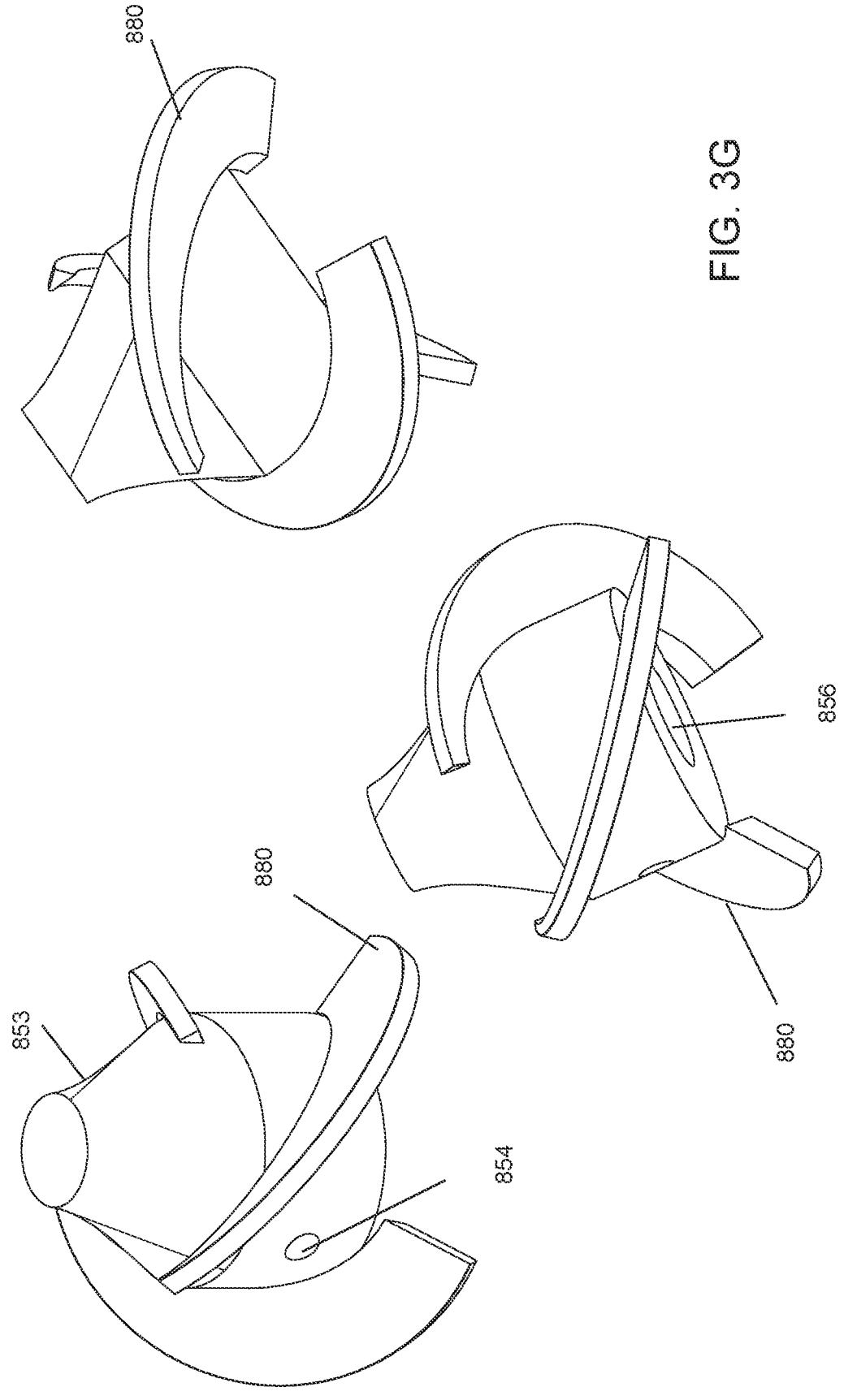

Referring now to FIGS. 3D and 3F, bioreactor 821 (FIG. 3D) can be durable and constructed from stainless steel or glass, for example, or can be single-use, manufactured from polymeric material, possibly pre-sterilized. The material specifications of bioreactor 821 (FIG. 3D) can affect thermal control, and can be taken into account by the controller when seeking a desired temperature of the contents. The contents of bioreactor 821 (FIG. 3D) may, depending upon the process executing within bioreactor 821 (FIG. 3D), require movement which can be provided, for example, by stirring (propelling), suction (impelling), agitation, the use of baffles, or by providing a flow of gas and removing waste products such as carbon dioxide. Movement can be driven from top or bottom-drive devices, mechanically- or magnetically-driven, for example. Agitator 832 (FIG. 3D) is one way to provide such movement. Impellers can include characteristics such as axial and radial fluid flow, and propellers can include various shapes such as pitched-blade or marine. The appropriate type of propeller/impeller can be chosen based upon the application. Impeller cone feature 852 (FIG. 3F) is installed, via shaft cavity 856 (FIG. 3F) on the shaft of an impeller, coincident to the top face of the impeller. Cone feature 852 (FIG. 3F) prevents cells or the like from settling on top of flat faces of the impeller when agitation is complete, and allows the cells or the like to roll down the impeller and settle at the bottom of the culture vessel where they can be collected by the dip tube. Cone feature 852 (FIG. 3F) includes hole 854 (FIG. 3F) to accommodate a set screw configured to hold cone feature 852 (FIG. 3F) in place on the shaft of the impeller. Cone feature 852 (FIG. 3F) includes a tight fit around the shaft of the impeller and no flat areas. Impeller fins 880 (FIG. 3G) are wrapped about cone feature 852 (FIG. 3G) at an angle to encourage cells to slide to the bottom of the culture vessel to order to be captured by tubing during harvest.

Continue to refer to FIG. 3D, in the present configuration, samples can be taken from fluids in the system, in the fluid lines entering and exiting bioreactor 821 (FIG. 3D). Further sampling ports at different locations are contemplated by the system of the present teachings. Pump 838 can enable recirculation in a system as shown in FIGS. 3D-3E, for example a system in which the contents of bioreactor 821 (FIG. 3D) are pumped downstream to enable use of the cells produced by the system, or pumped to waste 823 (FIG. 3D). In the shown configuration, harvested cells and media can be pumped downstream, and media from the downstream process can be recirculated to bioreactor 821 (FIG. 3D). The present configuration includes tubes extending into bioreactor 821 (FIG. 3D) to perform various functions, and the amount they extend can be adjusted depending on the desired function. For example, when agitator 832 is not activated, the cells and microcarriers will settle to the bottom of bioreactor 821. One of the tubes can extend into the mixture, but not to the bottom of bioreactor 821, and can be used to remove cells without removing media. Another tube can extend further into the mixture and can be used to remove cells for use in a downstream process, for example seeding of other bioreactors. Another use for the longer tube can be to completely remove media from the bioreactor 821 prior to adding fresh media or a different type of media.

Referring now to FIG. 3E, the downstream process is shown. In the exemplary configuration, incubator 851 (FIG. 3E) houses bioreactors 859 (FIG. 3E). Carbon dioxide 857 (FIG. 3E) is provided to incubator 851 (FIG. 3E) to establish an environment for bioreactors 859 (FIG. 3E). In incubator 851 (FIG. 3E), bioreactors 859 (FIG. 3E) are rotated by motors 861, as examples of what consumers of the batches created by the system of the present teachings might do. Cells and media 853 (FIG. 3E) that were created by the system of the present teachings are also provided to bioreactors 859 (FIG. 3E). Media and possibly other output 855 (FIG. 3E) are recirculated to bioreactor 821 (FIG. 3D). The characteristics of incoming (to bioreactors 859 (FIG. 3E)) and outgoing fluid can be monitored. For example, the pressure and air bubbles within the incoming fluid can be measured and adjusted to ensure that the cells will arrive at their destination in tact, and pH, DO, and air bubbles in the outgoing media can be measured and adjusted before re-entering bioreactor 821 (FIG. 3D). The system of the present teachings contemplates other types of characteristics that can be measured.

Figure 4:
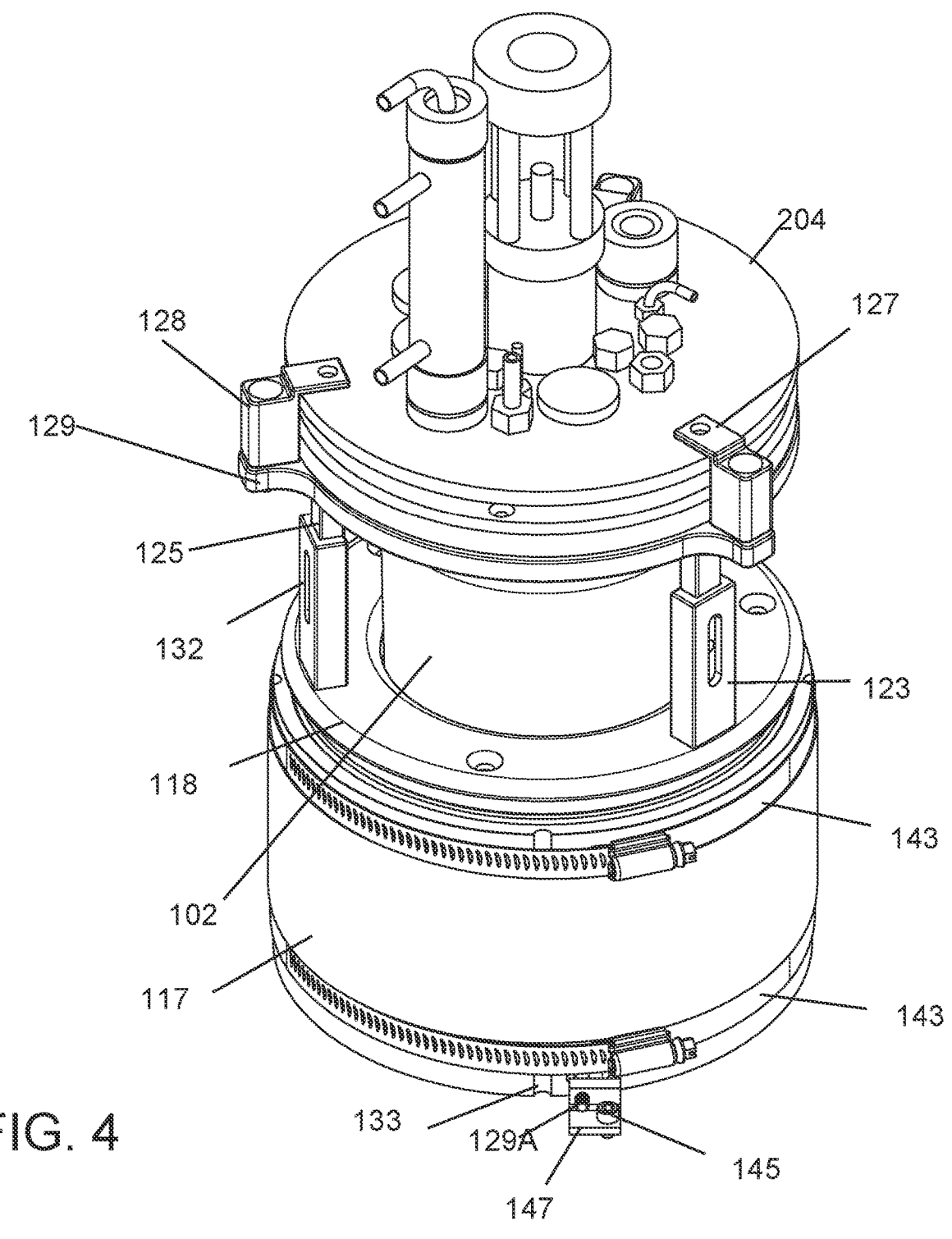
FIG. 4 is a perspective view of a first side of the assembly of the present teachings, including a commercial culture vessel.
Figure 5:
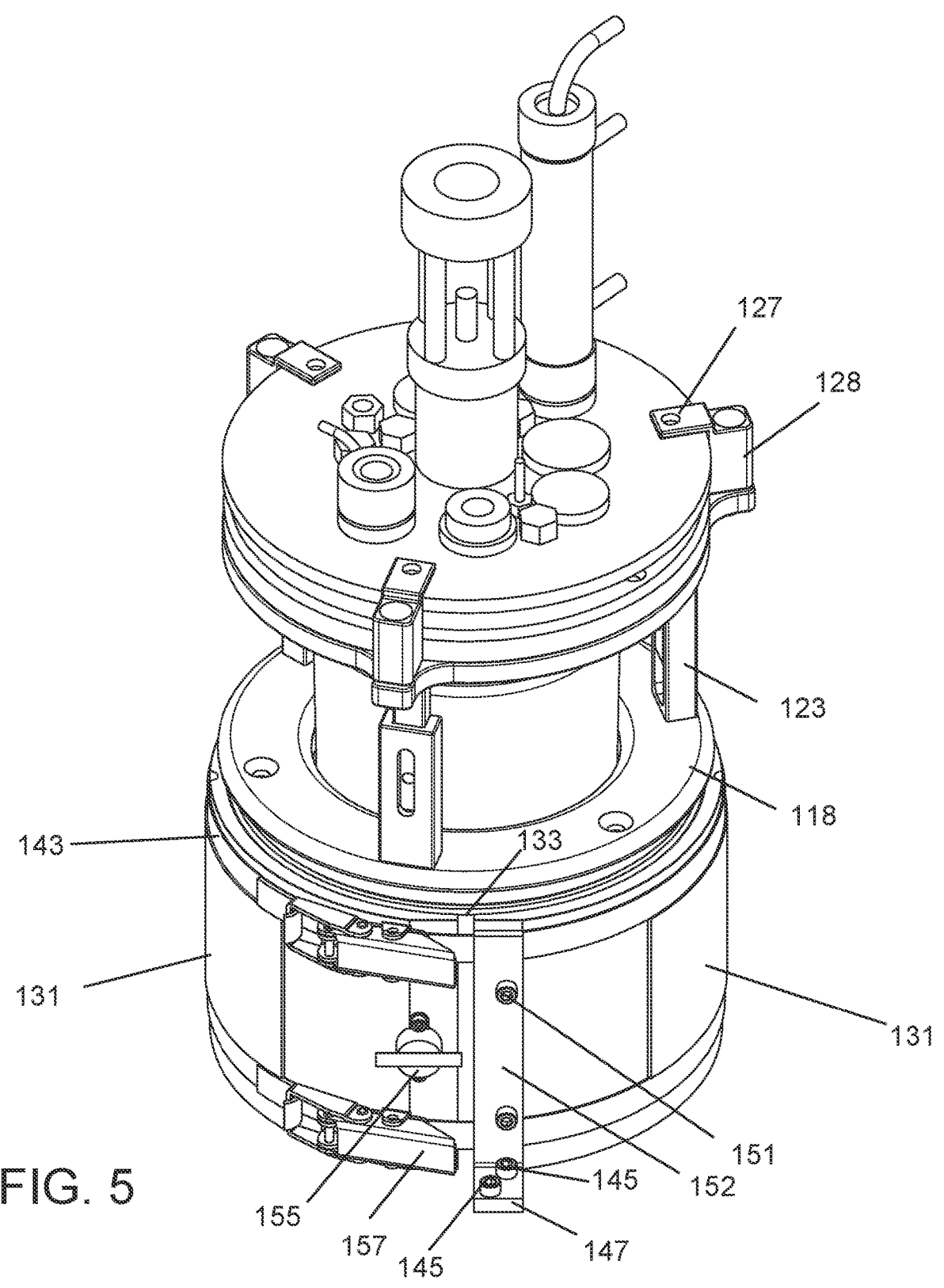
FIG. 5 is a perspective view of a second side of the assembly of the present teachings, including a commercial culture vessel.
Figure 6:
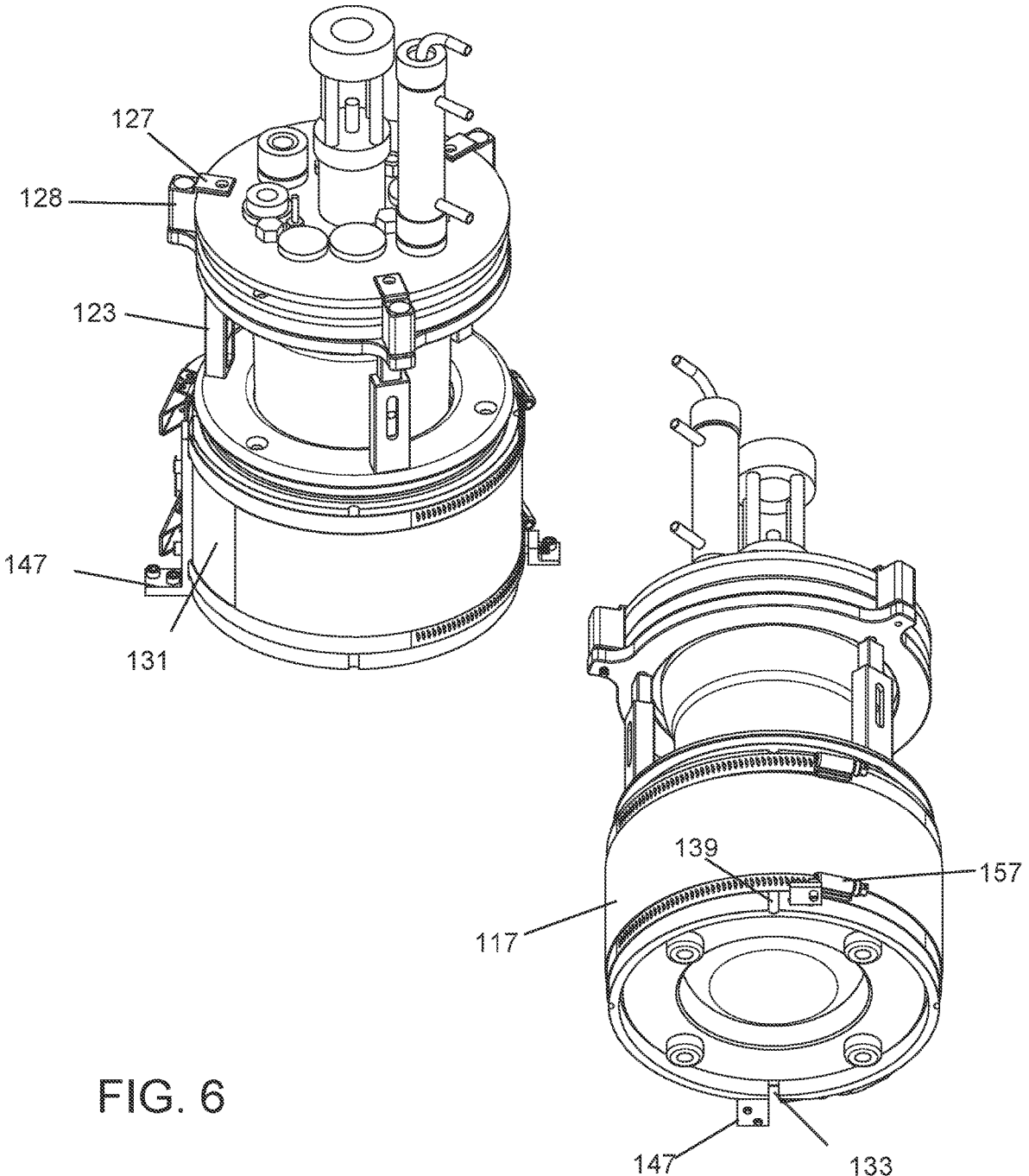
FIG. 6 includes perspective views of the bottom and top of the assembly of the present teachings, including a commercial culture vessel.

Referring now to FIGS. 4-6, a culture vessel system 101 (FIG. 1B) can include features that enable various sizes of culture vessels to be used and various environments to be established around the culture vessels. Culture vessel system 101 (FIG. 1B) can include features that hold the culture vessels in place to, for example, maintain an interface with a thermal management system.

Figure 7:
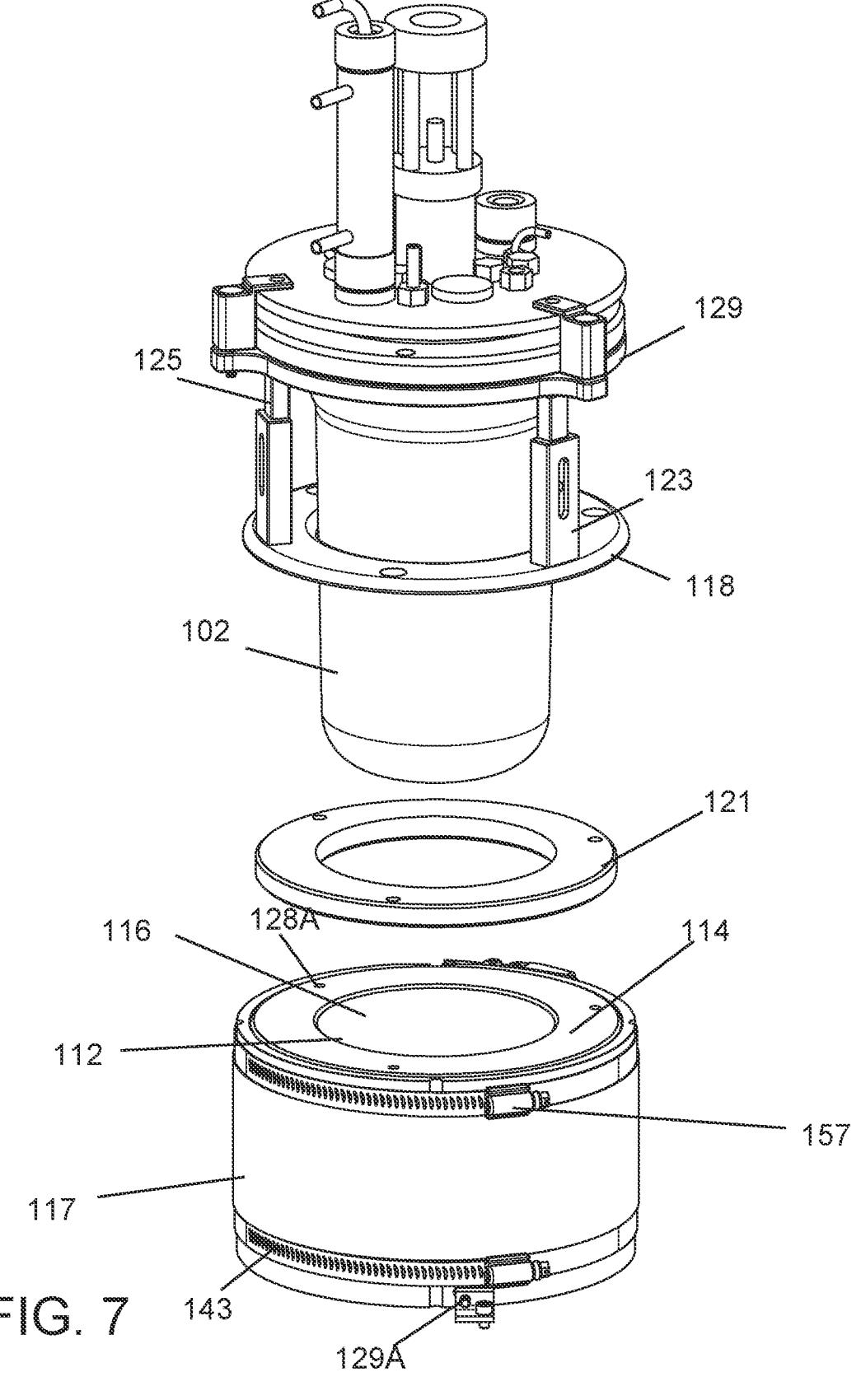
FIG. 7 is an exploded perspective view of a first side of the assembly of the present teachings, including a commercial culture vessel.

Continuing to refer to FIGS. 4-6, various sizes of culture vessels can be accommodated in culture vessel system 101 (FIG. 1B). The exemplary embodiment shown in FIGS. 6 and 7 illustrates culture vessel 102 captured in vessel clamp 120 (shown and described in detail herein with respect to FIG. 13). Culture vessel 102 can include a commercially-available bioreactor or a custom-designed bioreactor. The system of the present teachings can accommodate various sizes of culture vessels, thus culture vessel 102 is one example. Telescoping sleeve 123 and post 125 of vessel clamp 120 (FIG. 13) can enable extending/retracting the height of vessel clamp 120 (FIG. 13) to accommodate the heights of various culture vessels. The height of exemplary culture vessel 102 dictates a slight extension of telescoping post 125, locked in place by a fastener set in cavity 132.

Figure 10A:
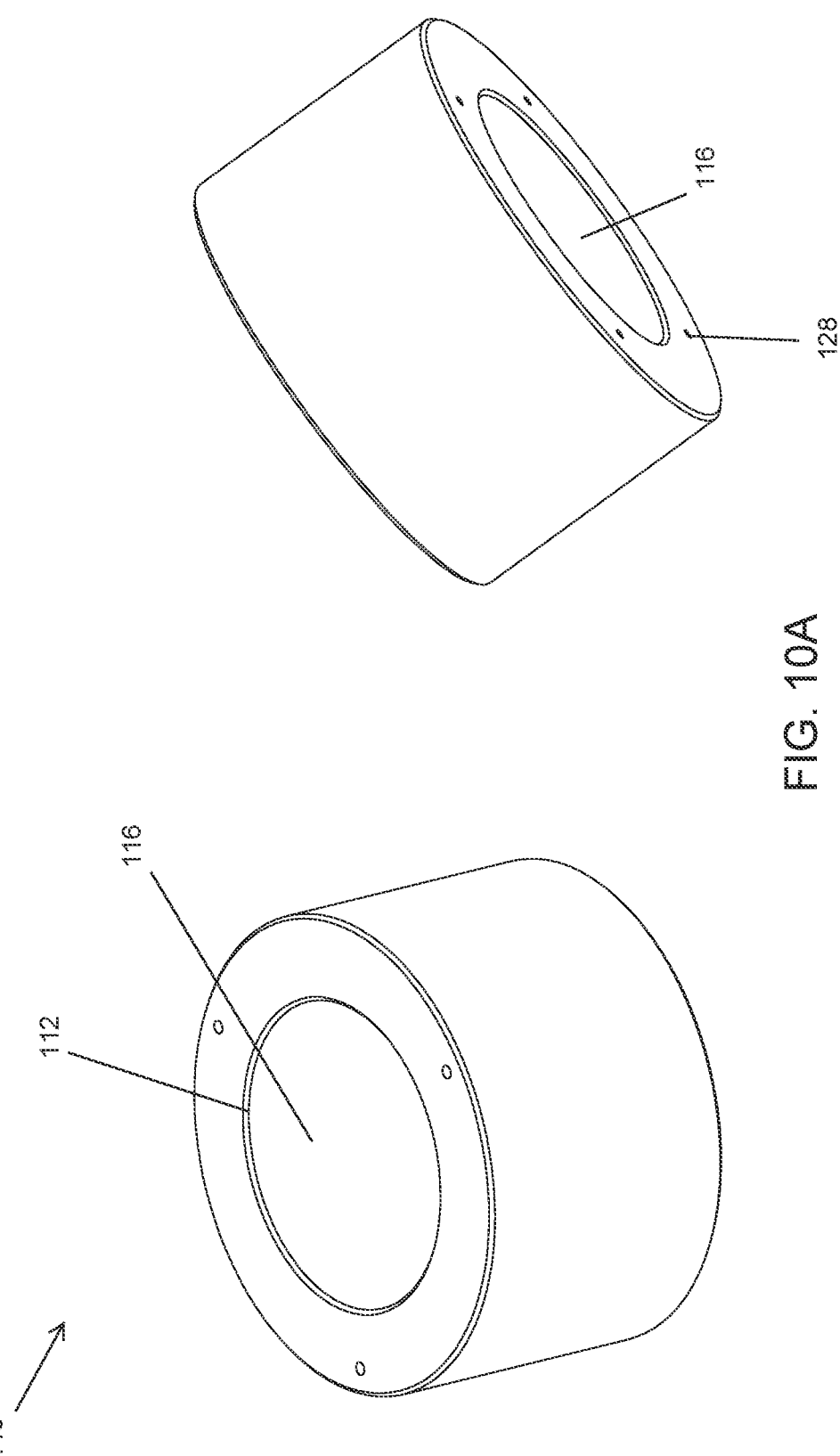
FIG. 10A is a perspective view of a first configuration of the vessel sleeve of the present teachings.
Figure 10B:
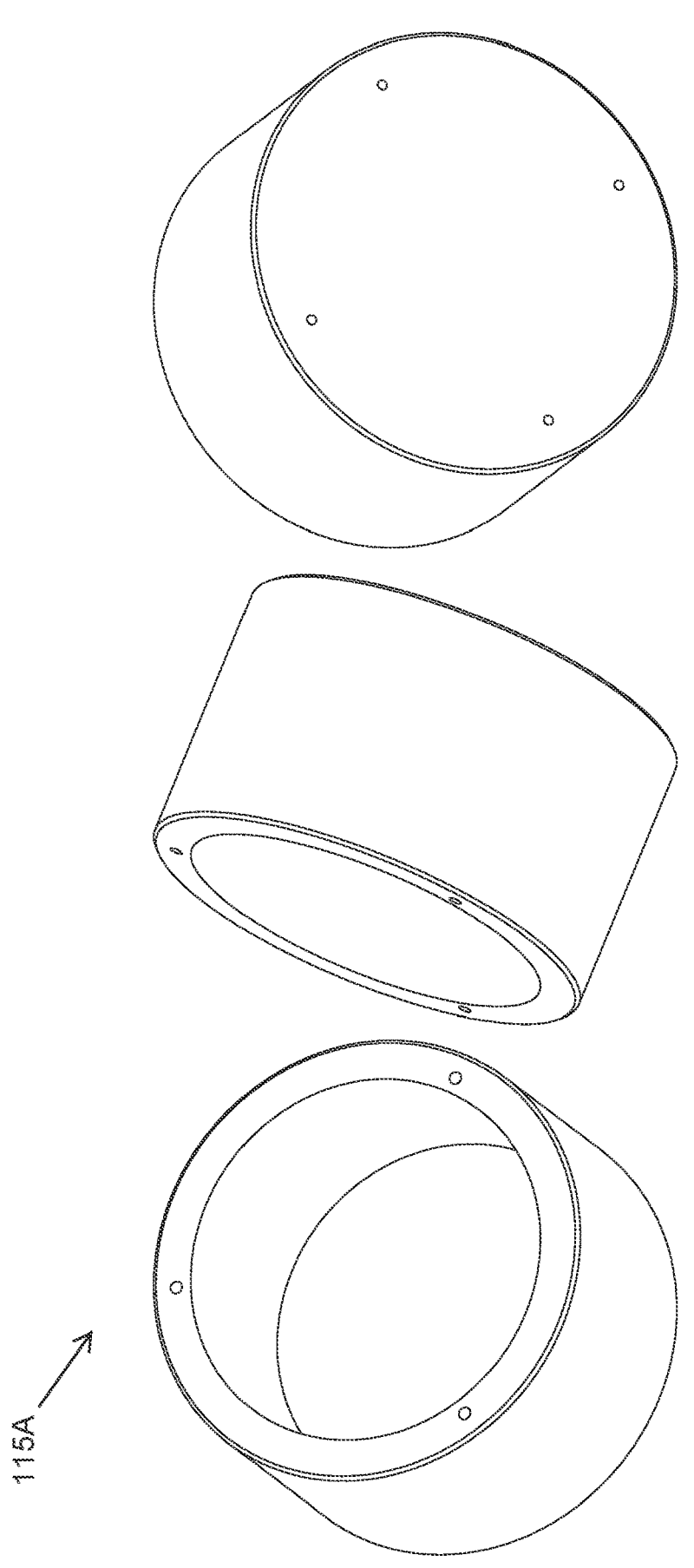
FIG. 10B is a perspective view of a second configuration of the vessel sleeve of the present teachings.
Figure 11:
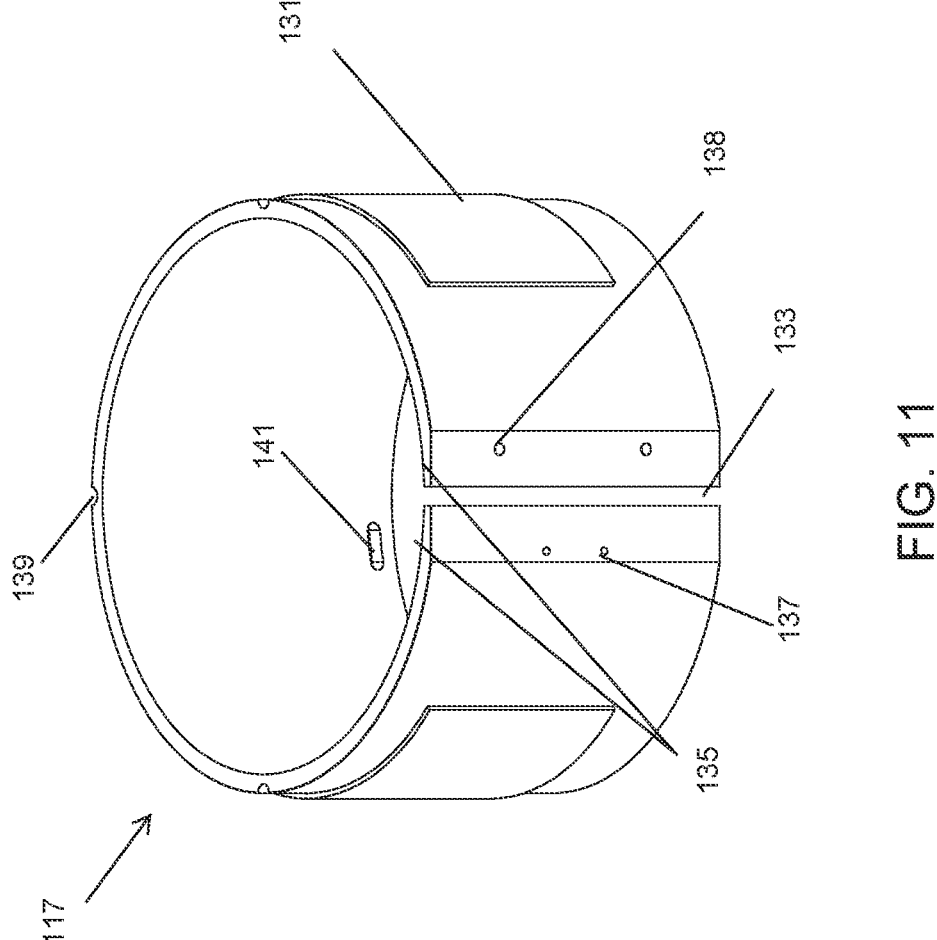
FIG. 11 is a perspective view of a configuration of the thermal sleeve of the present teachings.

Continuing to refer to FIGS. 4-6, vessel clamp 120 (FIG. 13) can stabilize vessel sleeve 115 (FIG. 10) and draw culture vessel 102 into vessel sleeve 115 (FIG. 10A) and therefore thermal sleeve 117 (FIG. 11) to ensure thermal conductivity between culture vessel 102 and thermal sleeve 117 (FIG. 11). The culture vessel clamp can ensure that the position of the culture vessel with respect to the vessel sleeve and the temperature management system is maintained in order to enable uniform temperature control of the contents of the culture vessel.

Continuing to refer to FIGS. 4-6, the temperature management system can be configured to maintain a desired temperature of the contents of the culture vessel. In some configurations, temperature management can be partially or completely integrated with culture vessel 102. In an arrangement, vessel sleeve 115 (FIG. 10A) can enable thermal conductivity between culture vessel 102 and thermal sleeve 117 (FIG. 11). Culture vessel 102 can be secured to vessel clamp 120 (FIG. 13) by fittings that surround cap 204 of culture vessel 102. The fittings can include multiple interconnected parts that can be configured to accommodate the size of cap 204. For example, the fittings can include vessel clamp ring stand 129 that can be mounted upon telescoping post 125, and provide a mounting surface for bracket base 128. Cap 204 can rest upon vessel clamp ring stand 129, and be vertically clamped by at least one headplate bracket 127 that can be operably coupled with bracket base 128. In some configurations, bracket base 128 and headplate bracket 127 can be formed as a single component. In some configurations, bracket base 128 and vessel clamp ring stand 129 can be formed as a single component, or can be separate parts. In some configurations, vessel clamp ring stand 129, bracket base 128, and headplate bracket 127 can be formed as a single component, or can be separate parts. In an arrangement, there are three headplate brackets 127. More or fewer of headplate brackets 127 can be mounted upon a suitably configured vessel clamp ring stand 129, depending at least upon the desired positional security of culture vessel 102. Vessel clamp 120 can be operably coupled with vessel sleeve 115 (FIG. 10A) by cap ring 118.

Continuing to refer to FIGS. 4-6, thermal break 121 can provide thermal insulation between vessel sleeve 115 (FIG. 10A) and the environment. Vessel sleeve 115 (FIG. 10A) can be surrounded by thermal sleeve 117, and thermal sleeve 117 can be securely coupled with vessel sleeve 115 (FIG. 10A) by, for example, but not limited to, straps 143. Thermal sleeve 117 can include cinching notches that can enable thermal sleeve 117 to comply when straps 143 are tightened. The position of thermal sleeve 117 with respect to vessel sleeve 115 (FIG. 10A) can be maintained by use of, for example, an easily inserted fastener 129A (FIG. 4) such as, for example, but not limited to, a dowel pin, a screw, a bolt, or a cotter pin. Fastener 129 is selected to allow float as vessel sleeve 115 (FIG. 10A) expands/contracts in the vertical axis.

Continuing to refer to FIGS. 4-6, thermal sleeve 117 can include thermal control means 131 and thermal sensor 155 (FIG. 5). Thermal control means 131 can include heating pads, heat strips, heat tape, and/or heat sheaths. Thermal sleeve 117 and thermal control means 131 can be secured to a mounting platform (not shown) by bracket foot 147, bracket 152, fasteners 151, and fastener 145, for example. Bracket foot 147 and bracket 152 can be a single component or separate components operably coupled by, for example, fasteners. Thermal sensor 155 (FIG. 5) can be used to disable thermal control means 131. Thermal sensor 155 (FIG. 5) can include, for example, but not limited to, a thermal switch with manual or automatic reset, a thermal fuse, or a positive temperature coefficient thermistor.

Figure 8:
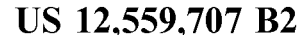
FIG. 8 is an exploded perspective view of a second side of the assembly of the present teachings, including a commercial culture vessel.
Figure 9:
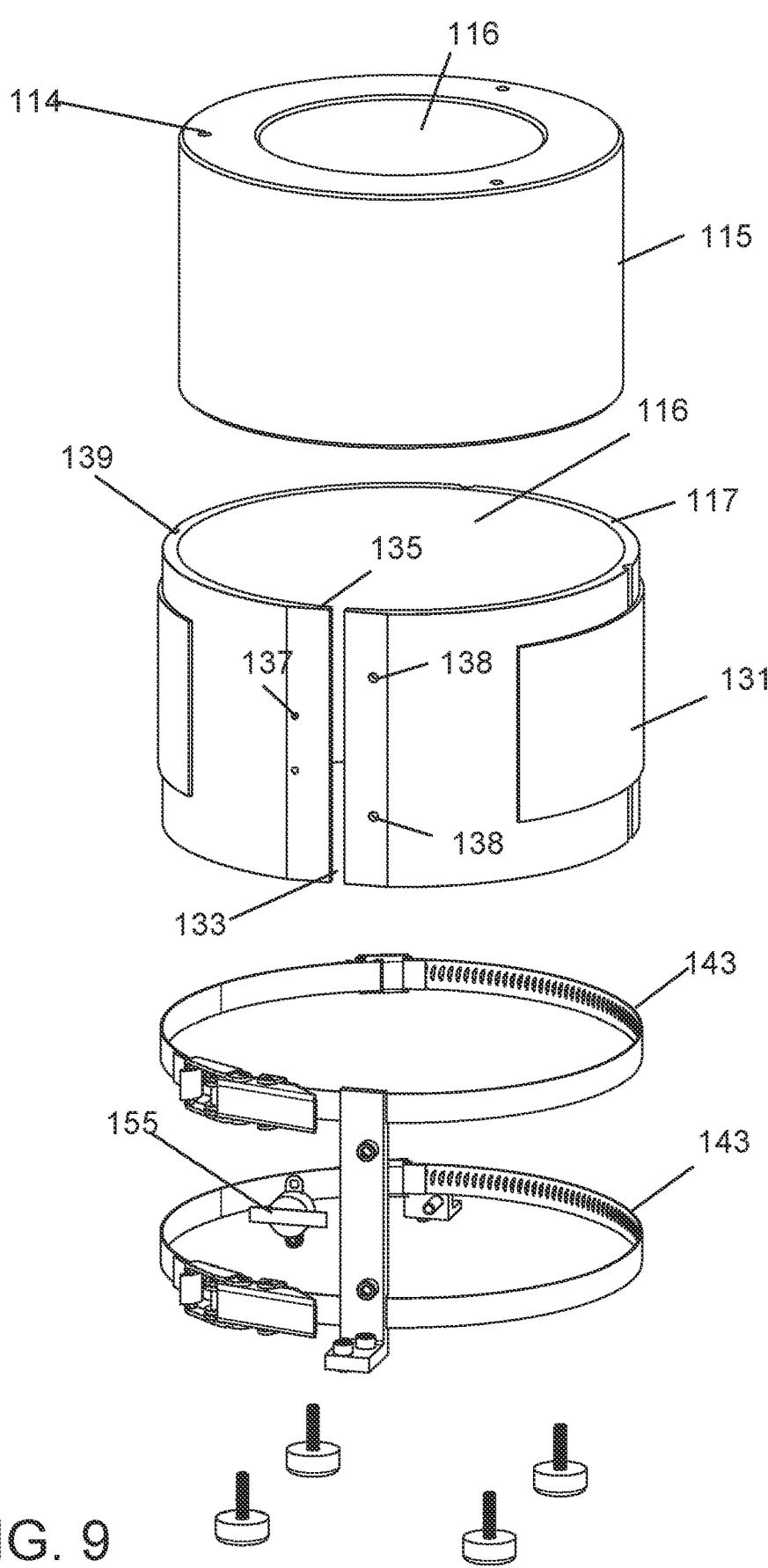
FIG. 9 is an exploded perspective view of a configuration of the vessel sleeve and thermal sleeve of the present teachings.

Referring now to FIGS. 7-9, the components of an exemplary system implementing the features of the present teachings are shown in partially exploded form. Culture vessel 102 is shown operably coupled with vessel clamp 120 (FIG. 13), a first step in assembling culture vessel 102 into an operational configuration. Vessel clamp 120 (FIG. 13) and culture vessel 102 can be lowered into vessel sleeve 117 and tightened into place before temperature management can being. Cap ring 118 can be lowered upon thermal break 121 into inner geometry 116, and fastened to vessel sleeve 115 (FIG. 10A) at fastening cavities 128A located on vessel sleeve face 114. Vessel sleeve 115 (FIG. 10A) and thermal sleeve 117 can be configured to accept culture vessel 102, i.e. strapped together and mounted upon a mounting surface. When culture vessel 102 is moved into inner geometry 116, straps 143 can be tightened, and fastener 129A can be inserted.

Referring now to FIG. 9, a configuration that enables various sized culture vessels to be used in a system implementing the features of the present teachings is shown in exploded form. To minimize custom requirements, thermal sleeve 117 can be a separate component from vessel sleeve 115. However, the functions performed by thermal sleeve 117 and vessel sleeve 115 can be performed by a single component. For example, the single component can include a cavity that can service all sizes of culture vessels by enabling the addition of the amount of filler material needed to maintain the position of the culture vessel within the thermal/vessel component. The filler material can include any thermally-conductive material that can be pressed against the culture vessel through tightening of straps 143, for example. Thermal sleeve 117 can include gap 133 that can enable space need to accommodate thermal expansion of vessel sleeve 115 and tightening of thermal sleeve 117 around vessel sleeve 115. Thermal cutout can be mounted at fastener cavities 137, for example.

Figure 12:
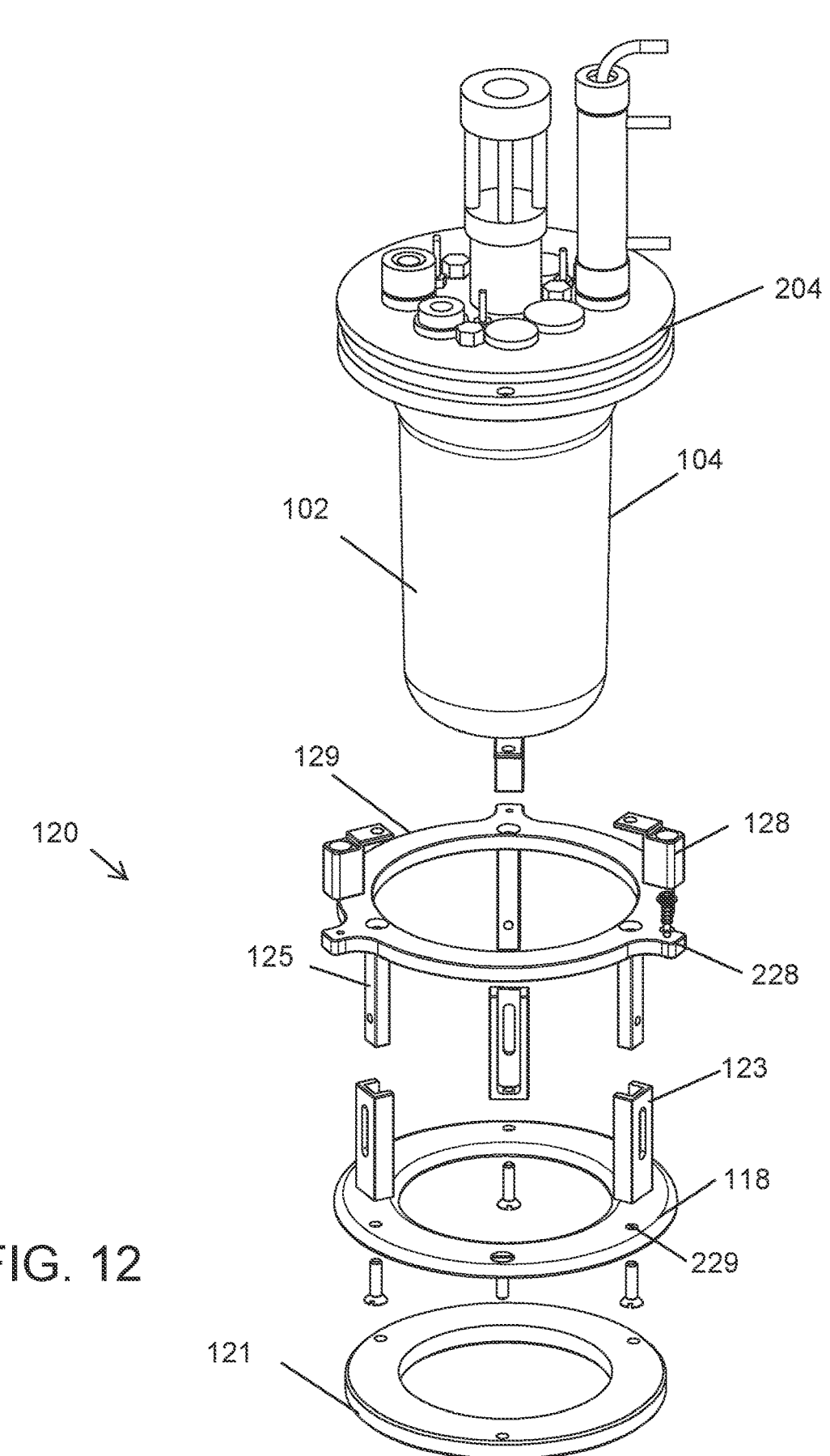
FIG. 12 is a perspective exploded view of the vessel clamp of the present teachings and a commercial culture vessel.
Figure 13:
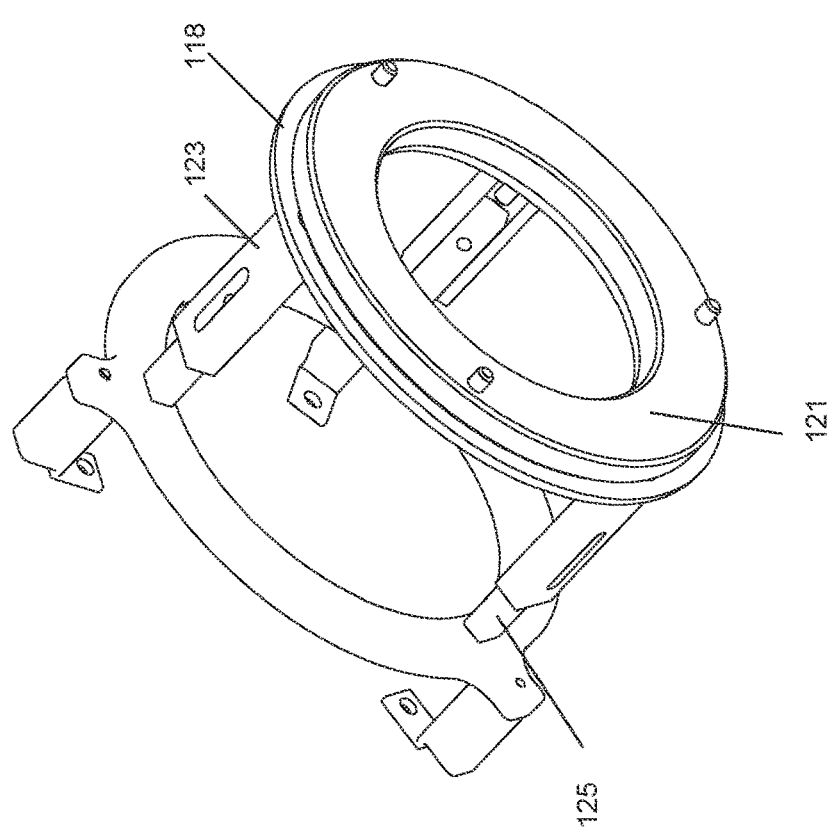
FIG. 13 is a perspective view of the vessel clamp of the present teachings.
Figure 13:
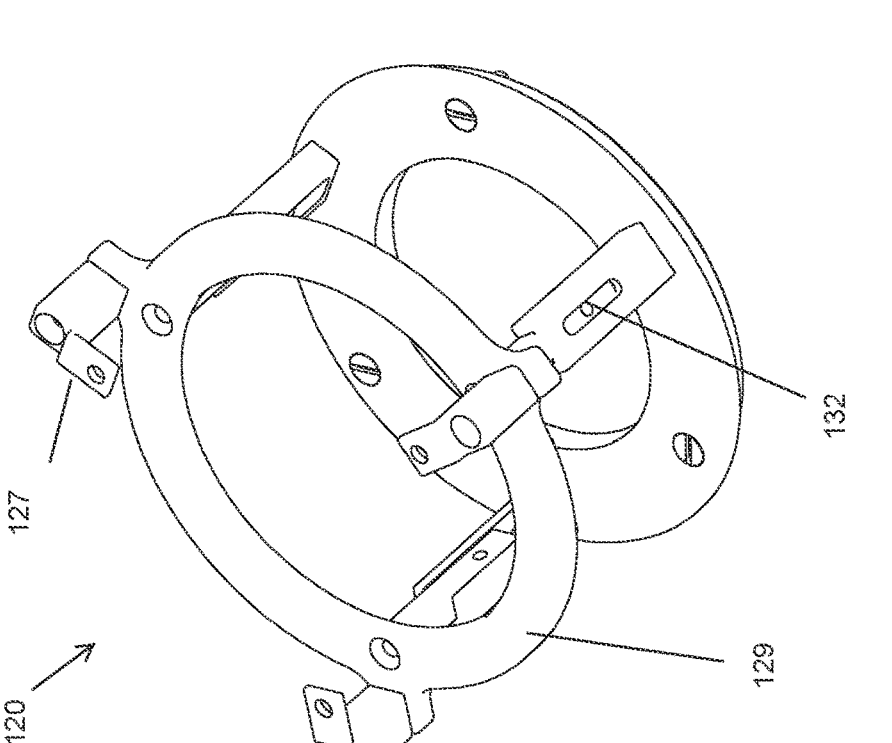

Referring now to FIG. 10A, vessel sleeve 115 can include inner diameter surface 116 that can, in some configurations, be constructed to match the geometry of culture vessel 102 (FIG. 12). For example, if culture vessel 102 (FIG. 4) includes tapered geometry 104 (FIG. 12), inner diameter surface 116 can be tapered to match culture vessel 102 (FIG. 12). Vessel sleeve 115 can vary in thickness depending upon the size of the culture vessel. Temperature maintenance of culture vessel 102 (FIG. 12) can be accomplished by positioning thermal sleeve 117 (FIG. 11) around vessel sleeve 115, and vessel sleeve 115 around culture vessel 102, fixing the entire configuration in place by vessel clamp 120 (FIG. 13). Thermal sleeve 117 (FIG. 11) can accommodate any size culture vessel 102 because its diameter does not vary with the diameter of culture vessel 102. Instead, in some configurations, inner geometry 116 of vessel sleeve 115 varies. Vessel sleeve 115 can include thermal ring cavity 112 that can accept a thermal compressible ring (not shown). The thermal ring can be fastened in any suitable way from thermal ring cavity 112 down the inner surface of cavity 116. Vessel sleeve 115 is designed to be removed easily, thermal sleeve 117 being left in place.

Referring now to FIG. 10B, in some configurations, vessel sleeve 115A can include a generic shape that can be used with a variety of culture vessel sizes and shapes. Generically-shaped vessel sleeve 115A can be combined with a conforming and thermally conductive material (not shown) that can ensure a uniformly flush interface between culture vessel 102 (FIG. 12) and vessel sleeve 115A.

Referring now to FIG. 11, thermal sleeve 117 can be operably coupled with thermal modification means 131 and leads (not shown) to power thermal modification means 131, which can be a commercially-available heater, for example. Thermal modification means 131 conducts heat into thermal sleeve 117, which then conducts heat into vessel sleeve 115 (FIG. 10A). In some configurations, thermal sleeve 117 can include gap 133 that can accommodate expansion and contraction of thermal sleeve 117. In some configurations, gap 133 can be surrounded by tapered edges 135 that result in forming flat mounting surfaces. In some configurations, an angle bracket (not shown), for example, can be attached on one leg of the bracket at connection points 138 to thermal sleeve 117. The other leg of the angle bracket can be used to secure thermal vessel 117 to a mounting base (not shown). In some configurations, thermal cutout sensor 155 (FIG. 9) can be attached to thermal sleeve 117 at attachment points 137. In some configurations, if thermal cutout 155 can be set to insure that thermal sleeve 117 does not exceed, for example, 60° C. In some configurations, the desired temperature of the contents in the culture vessel is 37° C. One goal of the system of the present teachings is to heat the contents of the culture vessel as fast as possible without raising the temperature of the contents above a pre-selected threshold such as 37° C. If the temperature of cutout sensor 155 (FIG. 9) exceeds a pre-selected threshold, it opens the power circuit to cut power to thermal modification means

131. In some configurations, thermal sleeve 117 includes a temperature sensor that enables sensor control system 105 (FIG. 1B) to use incoming sensor data sensing the temperature of temperature modification means 131 to adjust the power to temperature modification means 131. The goal of a high degree of control over the temperature of thermal sleeve 117, and therefore the content of culture vessel 101 (FIG. 1B), is to bring the contents to a pre-selected temperature as fast as possible without damaging the contents. Thermal sleeve 117 can include stress relief cuts 139 that can allow thermal sleeve 117 to expand, contract, and bend to conform when necessary. Thermal sleeve can include cavity 141 that can accept a stabilization device such as, for example, but not limited to, a dowel pin, screw, cotter pin, or bolt. Straps 143 can be tightened using, for example, but not limited to, strap cinches 157.

Referring now to FIG. 12, vessel clamp 120 and culture vessel are shown before they are coupled, and vessel clamp 120 is shown in exploded form. Bracket base(s) 128 can be operably coupled with vessel clamp ring stand 129 at standout(s) 228. Bracket base(s) 128 and standout(s) 228 are sized to surround cap 204, and vessel clamp ring stand 129 is sized to accommodate the diameter of cap 204. Other configurations are possible. For example, standout(s) 228 can include slide cavities that can enable bracket base(s) 128 to be positioned for different sized caps. Even further, vessel clamp ring stand 129 can include horizontally flexible but vertically rigid material that can expand/contract with the diameter of the culture vessel, but that provides a rigid mounting platform for bracket base 128 and telescoping post(s) 125. Telescoping sleeve(s) 123 can mount to cap ring 118 at mounting cavities 229. Alternatively, telescoping sleeve(s) 123 and cap ring 118 can form a single component. Other variations are possible, for example, some telescoping sleeve(s) 123 can be fastened to cap ring 118 while others are manufactured as part of cap ring 118.

Referring now to FIG. 13, vessel clamp 120 can include thermal break 121, telescoping sleeve 123, telescoping post 125 connected to vessel clamp ring stand 129, and headplate bracket 127, possibly spring-mounted to vessel clamp ring stand 129. Telescoping post 125 and telescoping sleeve 125 can operate in a coordinated way to enable vessel clamp 120 to extend/contract, thereby accommodating various heights of culture vessels. In particular, the culture vessels can be drawn towards the temperature control means provided by thermal sleeve 117 (FIG. 11) to enable efficient temperature control of the contents of the culture vessel. The desired vessel height can be secured by inserting a fastener through slide cavity 132 into thermal sleeve 117 (FIG. 11). Setting the desired height can be used to accommodate various height vessels to insure there is enough of the vessel that is in contact with the thermal sleeve, yet still keeping the vessel high enough for visual inspection of the fluid contents when the system is running. A fastener can set the height of the vessel clamp, based on height of the vessel. The vessel clamp can be adjusted to have adequate contact with the vessel ring. It can be desirable to have some of the vessel exposed to see view the contents of the vessel over time. The vessel clamp can be adjusted to hold the vessel above the bottom of the vessel sleeve to accomplish exposing part of the vessel for visual inspection. Between the bottom of the vessel sleeve and the vessel, heat that emanates from the vessel, the vessel sleeve, and the thermal sleeve can be trapped to maintain thermal uniformity around the vessel. In some configurations, the thermal sleeve can maintain a desired temperature of the contents of the vessel if the thermal sleeve makes contact with 1-2 inches or more of the side of the vessel. In some configurations, a thermal break (not shown) can be located at the bottom of the vessel sleeve. Vessel clamp 120 can operably couple with thermal break 121. Thermal break 121 is constructed of material that does not encourage the conductivity of heat between the base surface upon which vessel clamp 120 is mounted and ultimately the contents of the culture vessel. Thermal break 121 is operably coupled with vessel sleeve 115 (FIG. 10A) through cap ring 118. Cap ring 118 covers thermal break 121 to present a clean interface to the culture vessel assembly. To position culture vessel 102 (FIG. 12) securely for operational use, vessel sleeve 115 (FIG. 10A) is placed into thermal sleeve 117 (FIG. 11), which can have been previously been secured to a base chassis structure and coupled to a power supply and data I/O device. In some configurations, to use a different culture vessel, for example, to use a smaller sized vessel, vessel clamp 120 and vessel sleeve 115 (FIG. 10A) are removed, and vessel sleeve 115 (FIG. 10A) can be replaced with an appropriately-sized sleeve, but thermal sleeve 117 (FIG. 11) remains in place, along with its data and power connections. No change to the thermal management system is necessary to change culture vessels.

Referring again to FIG. 1B, pH and DO are important performance factors in the expansion and maturation of cells in a culture. Cell expansion happens in tissue culture vessels where the cells are surrounded by growth media, a substance containing growth factors, serum, and other additives. Cell expansion is the process of producing cells from a single cell. pH level and the amount of DO, as well as other cell characteristics, are maintained by the controlled addition of gases such as oxygen, nitrogen, and carbon dioxide by gas management system 107.

Figure 14:
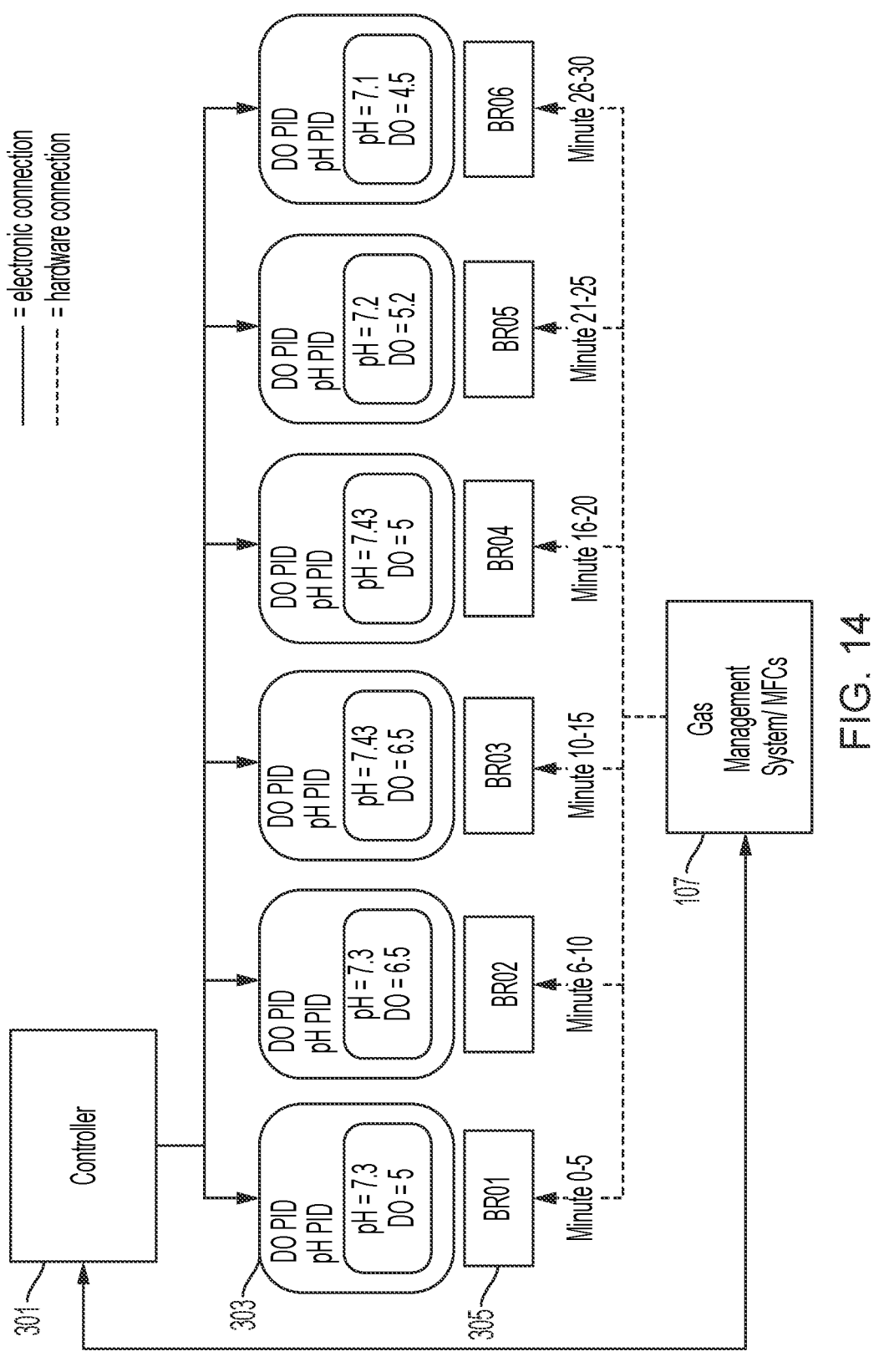
FIG. 14 is a schematic block diagram of an example use of the gas management system of the present teachings.

Referring now to FIG. 14, in some configurations, the gas management system of the present teachings can include a configurable number of active MFCs, that number possibly differing from the configurable number of active bioreactors, i.e., a complement of MFCs for all the gases is not required for each bioreactor. When a constant gas overlay is not needed, each active bioreactor is given a time slot in which it can receive a required gas mixture. The gas can settle into the contents of the bioreactor during the time when no gas is being provided to the bioreactor. The time gap, if any, between subsequent gas provisions to a specific bioreactor is configurable, as are the number of MFCs, the number of active bioreactors, and the amounts and types of gas being provided to a specific bioreactor during the time slot accorded to the bioreactor. These variables are set up in the recipe, for example, and enabled by the PLC. Many possible combinations of gas provision are contemplated by the present teachings.

Continuing to refer to FIG. 14, the gas management system controls gas resources across multiple culture vessels. In some configurations, sensors and mass flow controllers (MFCs) controlling the amounts of, for example, but not limited to, oxygen, nitrogen, and carbon dioxide that are exposed to the contents of the culture vessel are the main features of the gas management system. In some configurations, MFCs receive a mixture of gases depending upon at least in part on data from the sensors associated with the particular culture vessel, when the controller is controlling and monitoring multiple culture vessels. The sensors can be mounted to the culture vessel or elsewhere, depending upon the configuration of the system. In some configurations, sparging can be used to introduce gases to the contents of the culture vessel. In some configurations, gas management is enabled by electronic solenoids driven by a digital output card on the PLC chassis. In some configurations, the MFCs communicate with the PLC 301 via EthernetIP, and sensors communicate with the PLC 301 via RS-485, a serial protocol. In an aspect, a gateway is used to translate the serial protocol to EthernetIP. Other communications methods and protocols are contemplated by the present disclosure.

Continuing to refer to FIG. 14, gas management can be used to adjust the pH of the contents of the culture vessel. For example, some cell lines thrive in the pH range of 7.0-7.4. Additives to the contents of the culture vessel can initially set the pH of the contents to the desired range. For example, the culture medium can include a bicarbonate buffer. As the contents of the culture vessel convert glucose to lactate, carbon dioxide is produced, changing the pH and making the culture medium more acidic. Adding gaseous carbon dioxide can increase the dissolved carbon dioxide and decrease the pH. Adding air or nitrogen can decrease the dissolved carbon dioxide and increase the pH unless lactate accumulates in the culture medium, in which case a basic solution may be added to the contents to increase the pH. In an aspect, the set point of the pH in the culture vessel is achieved by overlaying carbon dioxide to lower the pH and nitrogen to allow the pH to rise. A PID loop drives the desired (variable) gas flow rate to a MFC. In an aspect, one gas, for example, but not limited to, carbon dioxide or nitrogen, is active at a time, depending if the pH is above or below the desired set point.

Continuing to refer to FIG. 14, oxygen gas dissolved in the blood (DO) is consumed by the cells in the culture vessel and requires replenishment by the gas management system. Some types of cell cultures a performed with a DO in the range of 20-50% saturation of oxygen, for example. In some configurations, air or nitrogen and oxygen can be added automatically, under the control of a controller, based at least on the comparison of sensor readings of DO in the contents of the culture vessel with a pre-selected set point. In an aspect, the set point of DO in the culture vessel is achieved by overlaying oxygen to increase or nitrogen to lower the dissolved oxygen percent in the vessel. In an aspect, bi-directional control is achieved using a PID loop with each MFC. In an aspect, addition of nitrogen, air, and/or oxygen is based on the difference between the amount of DO as measured by a sensor submerged in the contents of the culture vessel and a desired set point. When the DO exceeds the set point, nitrogen can be added to the culture vessel through a sparger to strip some of the oxygen out of the contents of the culture vessel. In an aspect, the contents of the culture vessel can simply consume the oxygen until the set point is readied.

Continuing to refer to FIG. 14, gas management system 107 can achieve a compact physical footprint and optimum equipment cost by, in some configurations, using a different number of MFCs than bioreactors. MFCs can measure and control the flow of liquids and gases. Types of MFCs in common use are designed and calibrated to control a specific type of liquid or gas at a particular range of flow rates. The description of the present teachings is not limited to the limitations of currently-available MFCs. For example, MFCs can be envisioned that are not limited to processing a specific type of gas, or a range of flow rates. Self-calibrating MFCs are contemplated by the present description. In an arrangement, MFCs can include a device that can programmably handle multiple gasses and pressure or flow rate inputs resulting in precise and repeatable outputs, such as, for example, but not limited to, the Brooks SLA 5800 series, connected by piping and filters to achieve a desired footprint and cost in a stand-alone enclosure. The number of MFCs needed is a function of the number of gas sources required for the configuration. In an aspect, the MFCs can include one MFC for $O_2$, one for $N_2$, one for $CO_2$, and one for compressed air, but any number of MFCs with any assortment of source gases is possible. The number of culture vessels in the configuration is a function of the number of cell cultures being expanded, or the number of tissues being maintained. In an aspect, the MFCs can deliver gases, possibly mixed, to multiple bioreactors on a scheduled time interval. Using a single set of MFCs for all the bioreactors to blend the gas mix and then doing a sequential, timed, and/or intermittent overlay or sparge to each bioreactor minimizes the number of MFCs required and minimizes gas consumption, exhaust, and waste.

Continuing to refer to FIG. 14, in an arrangement, controller 106 can maintain set points 303 by instructing gas management system 107 to provide gases to culture vessels 305 at various flow rates proportional to a control loop error. The proportion is dependent upon flow rate, and differs between gases. For example, for nitrogen and oxygen, the proportion is higher than carbon dioxide. The control loop error is calculated from a PID loop dedicated for each bioreactor. PID loop 303 can be used to drive the desired (variable) flow rate to an MFC. Controller 301 sends gas management system 107, including MFCs, a set point based on the PID loop error. For example:

$$\text{Gas flow rate} = C * \text{control loop error}$$

where C=f(flow rate, type of gas) and $$\text{Control loop error} = \text{set point} - \text{measured data}$$

A proportional controller is set to work with a specific cell type. PID tuning parameters can be determined empirically by starting with a cell type and working backwards. In an arrangement, proportional control can be used without integral or derivative aspects. In an arrangement, steady state control (low deviation from set point) can be achieved by using any of proportional, integral, or derivative controls, separately or in combination.

Continuing to refer to FIG. 14, the set point of the pH in culture vessel 305 is maintained by overlaying $CO_2$ enabling a reduction in the pH (more acidic) and $N_2$ enabling an increase in the pH. Gasing can maintain a steady pH until the levels of glucose and lactate become the overwhelming pH driving factor. After a period of time, a media exchange will be needed to maintain the pH set point due to glucose consumption and lactate production, as described in Michl et al., "*Evidence-based guidelines for controlling pH in mammalian live-cell culture systems*, COMMUNICATIONS BIOLOGY|2:144| https://doi.org/10.1038/s42003-019-0393-7/www.nature.com/commsbio (2019), incorporated herein by reference in its entirety. When the pH measures <7.2 a media exchange may be necessary. In an arrangement, if continuous gassing fails to change the characteristics of the cell culture, an immediate replacement of the media will be instituted. In an arrangement, glucose and lactate can also be monitored.

Continuing to refer to FIG. 14, the set point of the Dissolved Oxygen (DO) in culture vessel 305 can be achieved by overlaying $O_2$ to increase or $N_2$ to lower DO %. The value of the set point is process specific, depending on the type of cells being expanded, or the tissue being grown. Some cells or tissues thrive in an oxygen-rich environment, while others thrive in an oxygen-depleted environment, as discussed in Place et al, "Limitations of oxygen delivery to cells in culture: An underappreciated problem in basic and translational research", *Free Radical Biology and Medicine*, 113: 311-322 (2017), incorporated herein by reference in its entirety. Additionally, gas transfer laws dictate how much of the oxygen is dissolved into solution, and ultimately reach the cells. In an arrangement, a recipe can be used to adjust the pH and DO set points according to the current values of various measured parameters, the recipe being made available to controller 106, enabling the system to accommodate various pH and DO set points derived from cell type. Similar to control of the pH, bi-directional control will be achieved using two PID loops 303 for each set point. Bi-directional control provides a response to a positive and negative error on a set point, for example, adding oxygen when below a set point, and adding nitrogen when above the set point.

Continuing to refer to FIG. 14, in an aspect, the system can include multiple culture vessels 305 growing cells and tissues at the same time. Since there can be multiple vessels in use at once, a control strategy to deliver a specific gas mixture to each vessel 305 is deployed. When the rate of change of the pH and DO levels is slow enough that constant gas overlay is not needed, gas can be overlain in culture vessel 305 during a time period, and then the gas infusion can be discontinued while diffusion of the gas into the contents to take place. A dormant period of a pre-selected time can be built into the process to account for processes/content that require more than the pre-selected gas delivery time. When the gas(es) are being delivered, PID loops are dictating set points for monitored characteristics such as, but not limited to, pH and DO. In an aspect, each culture vessel includes separate and/or dedicated PID loops. Periodically providing a gas overlay is a successful strategy at least in part because the impacted characteristics have a relatively slow rate of change. The isolation of gas delivery to one culture vessel is achieved by actuating solenoid valves downstream of the MFC to control the direction of mixed gas.

Continuing to refer to FIG. 14, controller 106 can direct gas management system 107 to supply gas, possibly a mixture of available gases, to a specific culture vessel 305 for a specific timeframe. Controller 106 can then direct gas management system 107 to change the mixture, if necessary, to accommodate the contents of a second culture vessel 305, and then direct gas management system 107 to deliver the gas to the second culture vessel 305. This process can be repeated for each culture vessel 305 in the system. Culture vessels 305 can be revisited with further gas infusions, possibly different mixtures, depending upon the specific requirements of the contents of the culture vessels, and/or depending upon parameter measurement results. The isolation of gas delivery to one culture vessel 305 can be achieved by actuating specific solenoid valves based on a timed schedule. The coordination of MFC set point and valve states can be driven by a sequenced routine in the controller. The sequence gives each culture vessel a time period to read pH/DO through pH/DO sensors (FIG. 1C), deliver gas, and move on to the next culture vessel. This time-sharing enables sharing of hardware components, and minimizes gas consumption, exhaust, and waste.

Referring now to FIG. 14, for example, if there are six culture vessels 305, and each requires gas delivery for five minutes, a cycle of visiting the culture vessels 305 and supplying gas to them will require thirty minutes. In a culture vessel 305 in which the gas diffusion rate is the same as the cycle time, controller 106 can direct gas management system 107 to supply more gas to that culture vessel 305. In the exemplary process, the set point to each MFC can change every five minutes depending on the error output of pH and DO PID loops 303 for each culture vessel 305.

Controller 106 calculates the error from the PID loop/probe in each culture vessel 305 to set up for correcting the gas on the next gas window.

Continuing to refer to FIG. 14, condensation of liquid in the gas line exiting the culture vessel can possibly foul gas management equipment. In an aspect, air dryers can be used to strip incoming gas from liquid impurities. In an aspect, a heating system such as, for example, a Peltier heating system can prevent condensation of liquid in the gas line exiting the bioreactor. In an exemplary Peltier heating system, one junction is cooled while the other is heated, and an electric current is maintained in a circuit of material including two dissimilar conductors or semi-conductors. An increase in the temperature occurs at the junction where, for example, copper passes to bismuth, and a decrease in temperature occurs at the junction where, for example, bismuth passes to copper. In an aspect, the Peltier heating system includes a thermo-electric heater and fan. In an aspect, the controller provides commands to the fan and thermo-electric heater through digital outputs associated with the controller.

Figure 15A:
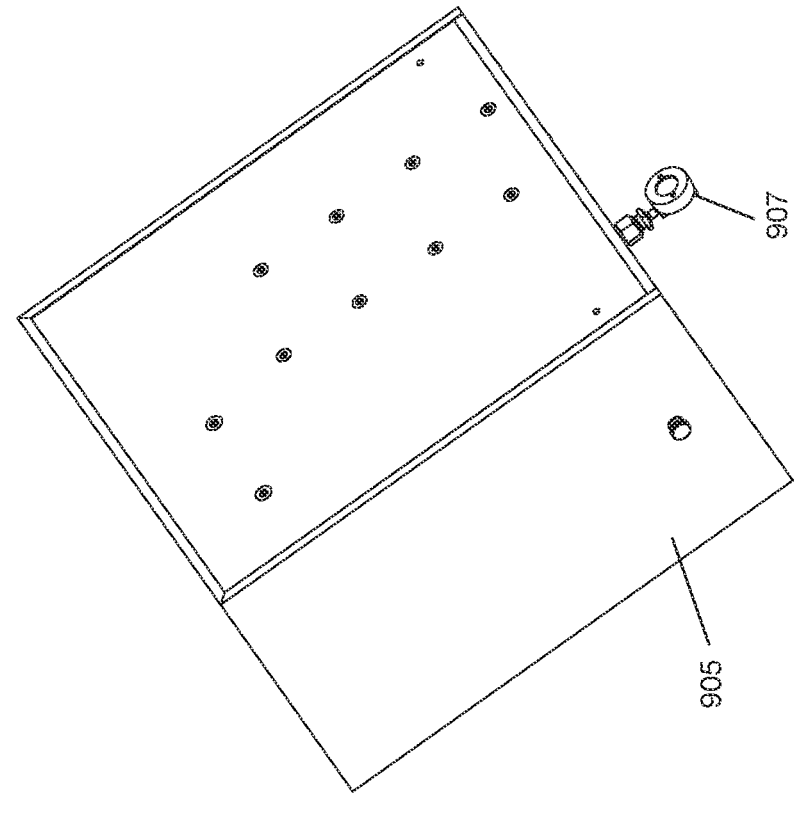
FIGS. 15A-15F are perspective views of components of an implementation of the gas management system of the present teachings.
Figure 15A:
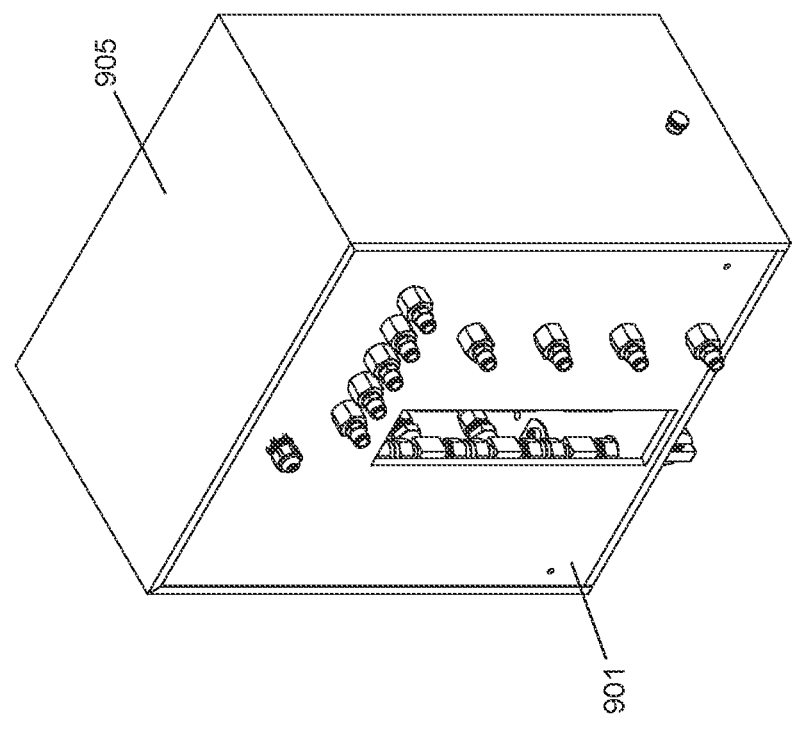
Figure 15B:
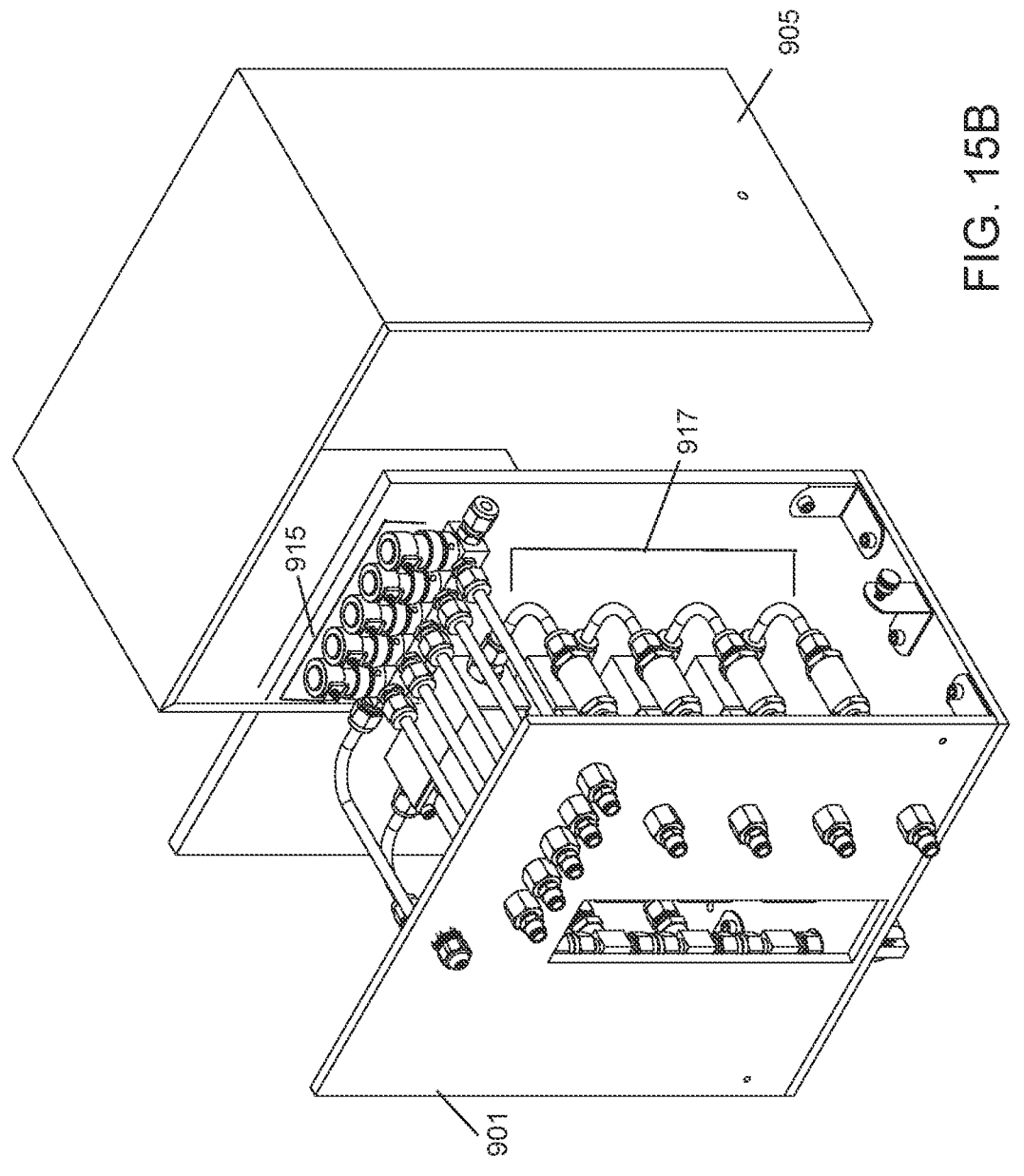
Figure 15C:
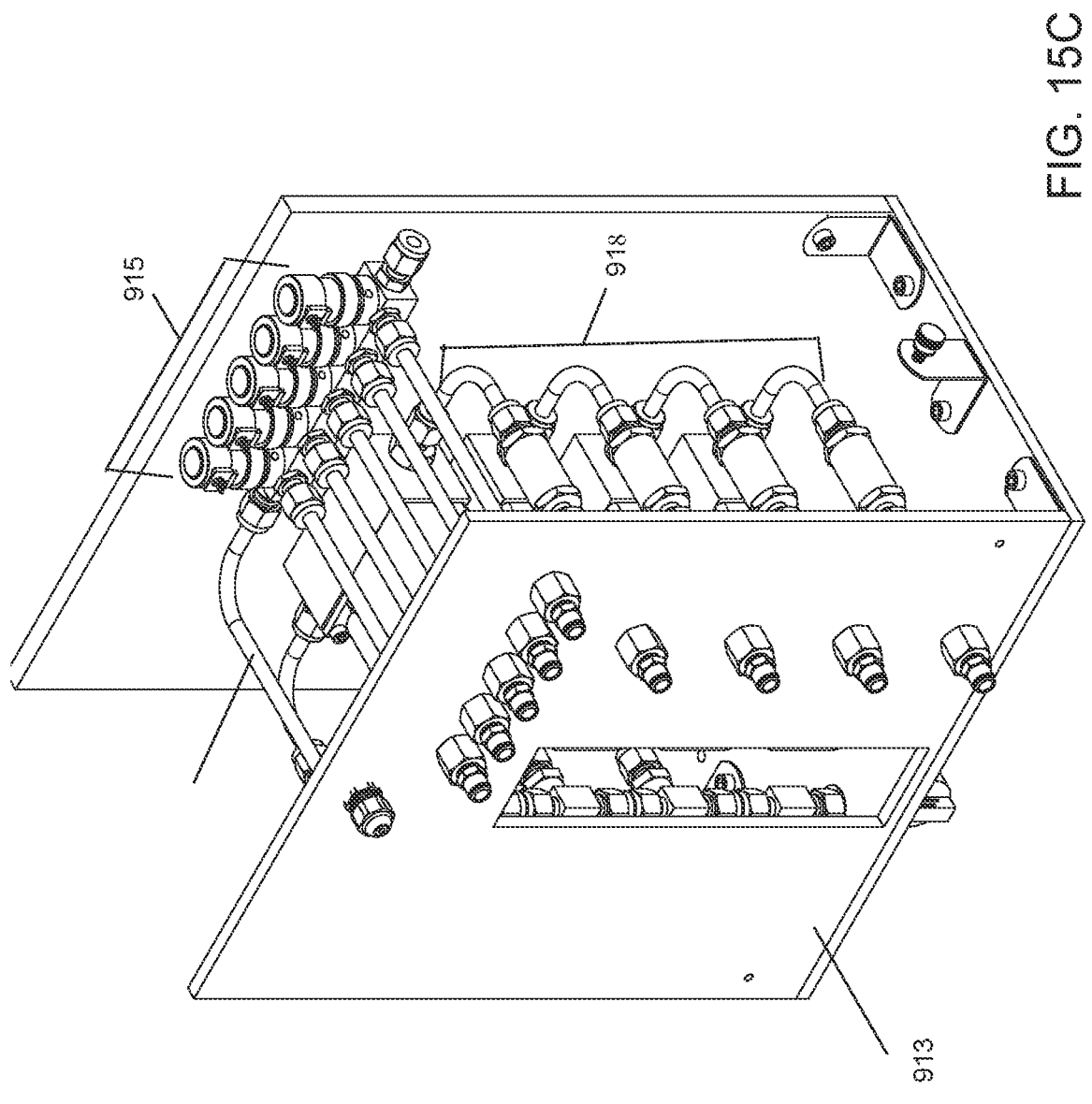
Figure 15D:
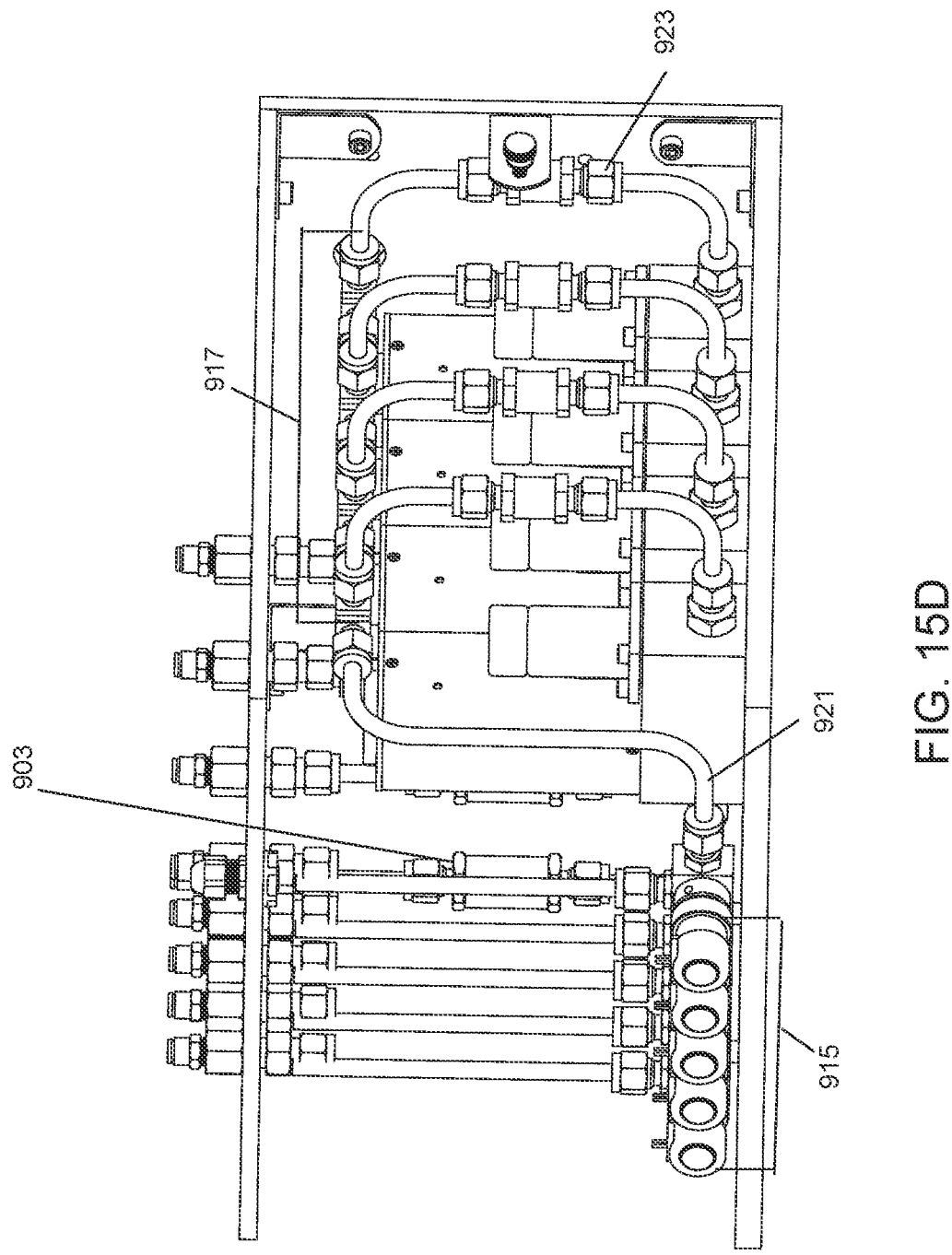
Figure 15E:
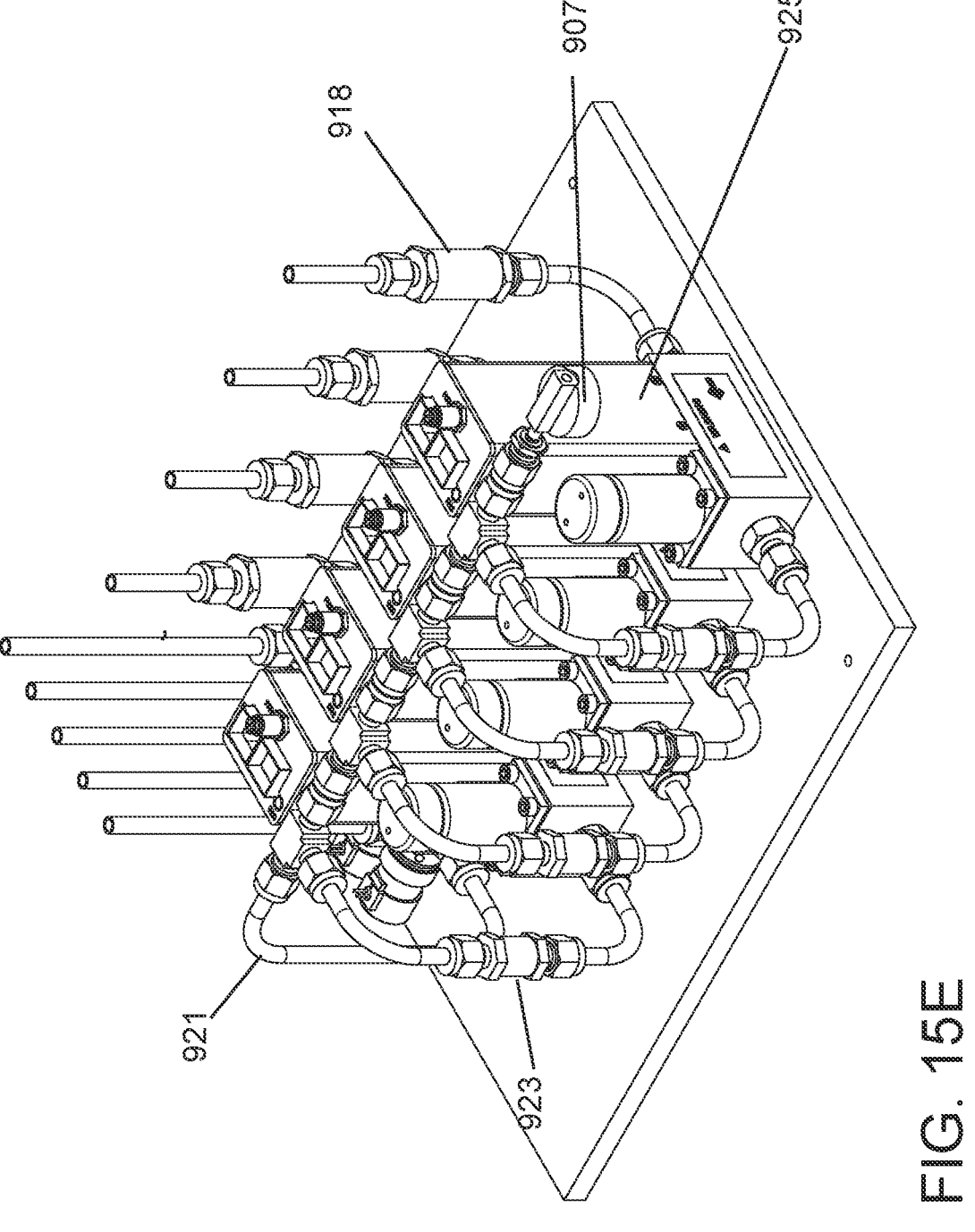
Figure 15F:

Referring now to FIGS. 15A-15F, components of an exemplary gas management system are shown. Specifically, the enclosure that houses the MFCs and gas manifolds is shown in FIG. 15A. Shroud 905 and base 901 form the enclosure that protects the gas management system of the present teachings. Extending from shroud 905 is pressure relief valve 907 which is attached to mixing manifold 917 (FIG. 15D). With shroud 905 (FIG. 15B) partially removed, distribution manifold 915 (FIGS. 15B/C) is shown. Gas entering MFC inlets can be filtered by particulate filters 918 (FIG. 15C). Distribution manifold 915 (FIGS. 15B/C) receives gas according to the type and amount required for a particular process as specified by PLC 106 (FIG. 1B). Each gas train incorporates a connection to MFC 925 (FIG. 15E), particulate filter 918 (FIG. 15E), and a check valve. There are the same number of gas trains as there are source gases in the system. Gas from each gas train (MFC) is blended in mixing manifold 917 (FIG. 15D) and distributed to the desired bioreactor through distribution manifold 915 (FIG. 15D). Distribution manifold 915 (FIG. 15D is the exit from the gas mixer to the bioreactors. Distribution manifold 915 (FIG. 15F) enables distribution of the source gases according to PLC 106 (FIG. 1B) commands. Distribution manifold 915 (FIG. 15F) includes features such as pneumatic manifold fixtures 933/935 (FIG. 15F), exemplary 5-station unit 937 (FIG. 15F), and exemplary 2-way normally closed solenoid valve 931 (FIG. 15F). The system of the present teachings contemplates larger or smaller units accommodating more or fewer gas sources.

Figure 16:
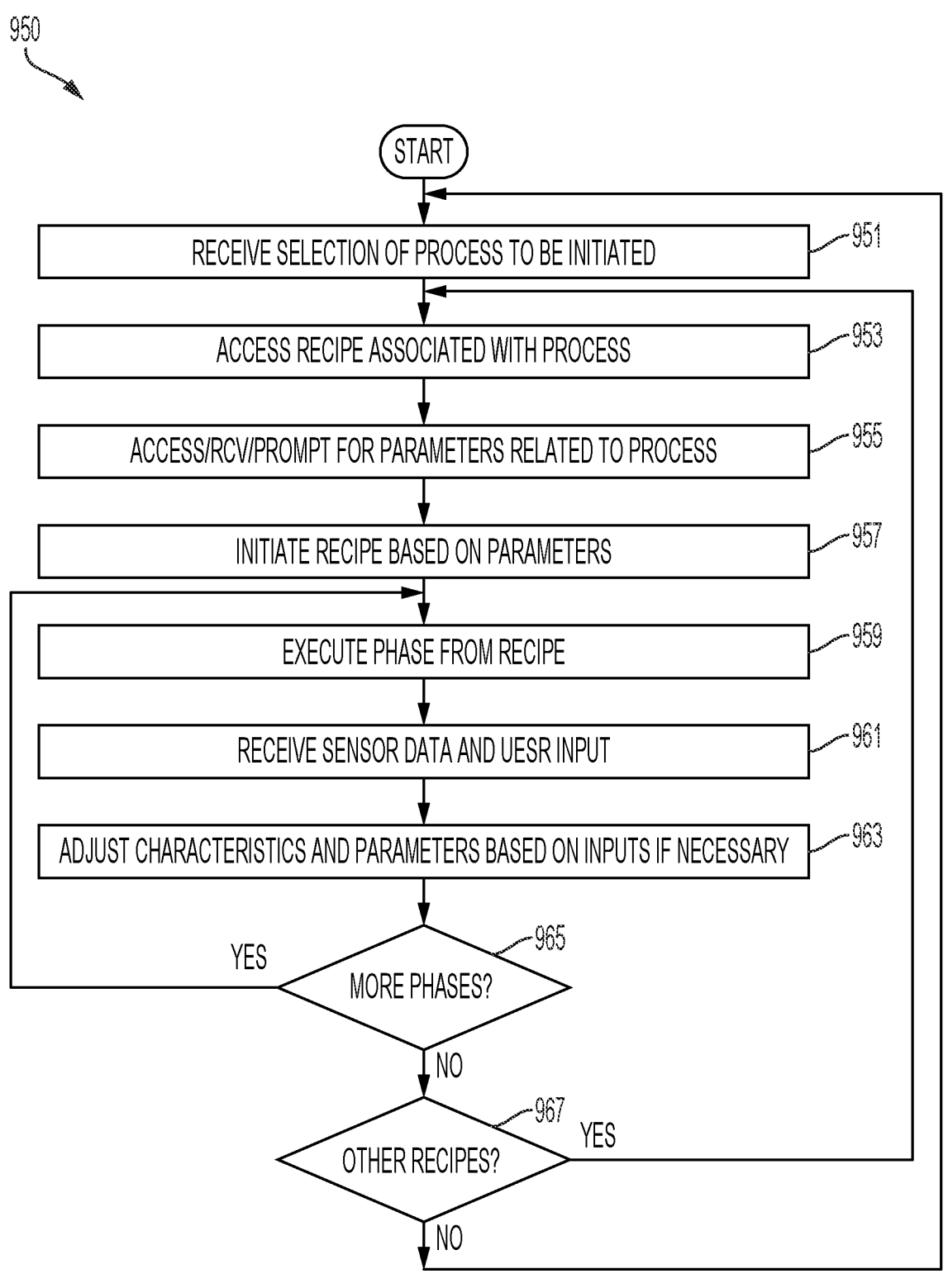
FIG. 16 is a flowchart of an exemplary controller process of the present teachings.

Referring now to FIG. 16, controller (PLC) 106 (FIG. 1) receives data from the sensors associated with the culture vessel, fluid management system, and gas management systems, and uses those data to control system functions to achieve a desired outcome such as, for example, but not limited to, tissue generation, scaffold decellularization, and scaffold recellularization. PLC 106 (FIG. 1B) is integrated wired (or wirelessly) to control the other parts of the system without requiring command translations. PLC 106 (FIG. 1B) can detect faults in incoming sensor data, and, after validation is complete, use the data to enable change in state, for example, for choosing a sequence of output commands to motors, pumps, and valves. In some configurations, the order of the state changes and/or the sequence of commands can be driven by a recipe. The recipe itself can be changed by user input, or by PLC 106 (FIG. 1B) based on conditions in the system. Other ways that the recipe can be changed, or that control can proceed, are contemplated by the present teachings.

Continuing to refer to FIG. 16, PLC 106 (FIG. 1B) of the present teachings follows a general flow for all processes for each culture vessel station (including culture vessel 503 (FIG. 1B), fluid handling system 108 (FIG. 1B), and culture vessel control 111 (FIG. 1B)) that can be executed by the system of the present teachings. PLC 106 (FIG. 1B) can manage simultaneously different processes executing in the culture vessels of the present teachings. Therefore, a version of method 950 can be executing in PLC 106 (FIG. 1B) for each of the culture vessels. Method 950 can include, but is not limited to including, receiving 951 selection of the process that is to be initiated. Exemplary processes include, but are not limited to including, cell maturation, organ decellularization, and organ recellularization. The selection can be made, for example, by a user through, for example, but not limited to, a secure remote communications line, a local hard-wired line, or a secure wireless connection. HMI 630 (FIG. 1C) is one way a user can select a desired process. The display associated with HMI 630 (FIG. 1C) can be provide status information for each culture vessel. The display can be divided into a number of sections, depending upon the number of active culture vessels, for example, or depending upon the total number of culture vessels, active or not. Alternatively, HMI 630 (FIG. 1C) can include multiple monitors, each supporting an active culture vessel. Still further, processes can be related to one another, so process selection can happen automatically, or semi-automatically, with the user approving the selection before process execution proceeds. For example, a decellularization process can automatically or semi-automatically kick off a recellularization process. Method 950 can include accessing 953 a recipe associated with the selected process. When there are multiple possible recipes for a selected process, user input can be required to pick the desired recipe. Alternatively, PLC 106 (FIG. 14) can select and access the most appropriate recipe based on previous or concurrent processes executed by one or more of the bioreactors in the system. User interaction can be provided to verify the selection, depending on characteristics associated with the process and the recipe.

Continuing to refer to FIG. 16, method 950 can include accessing or computing or receiving or prompting for 955 parameters related to the selected process and/or the selected recipe. For example, set points for temperature, pH, and DO can be provided. The user can enter required values, or choose to use default values, or the user can be out of the loop entirely as the system can choose default values or compute values based on prior or concurrent activity in the system. Method 950 can include initiating 957 the selected recipe using the parameters. The recipe initiation sets up a processing loop that moves through the recipe until all phases have been accomplished, then checks for further recipes, and finally returns to the beginning to receive a process selection. In the processing loop, method 950 can include executing 959 a phase from the recipe, for example, executing instructions to open valves, pump media, or activate an agitator. Elements of the ISA-88 phase module are provided, in the system of the present teachings, by programs that, for example, but not limited to, open valves, start pumps, totalizes the flow with a sensors until a pre-selected amount is reached, stops the pumps, and closes the valves. Phase control of the present teachings arbitrates the ownership of equipment based on pre-selected criteria. For example, in some configurations, when running an automated phase all devices are set to be controlled by the PLC, unless there are manual steps within the sequence. Essentially all equipment is owned by the PLC during automated phase and recipes. In some configurations, an operator take ownership of a device of interest under specific circumstances. When the operator has completed use of the device, the phase resumes and the PLC takes ownership of the device. In some configurations, possible modes include operator, external, and maintenance. Other possible modes are contemplated by the present teachings. The modes are associated with users who can lock ownership of the equipment. The owner user must release the lock before the controller can grant ownership to another user. In the system of the present teachings, multiple phases can execute simultaneously. For example, a heating phase can execute simultaneously with an agitate phase and recirculate phase. In some configurations, each culture vessel has dedicated equipment and dedicated software, enabling simultaneous unrelated operations on different culture vessel contents.

Continuing to refer to FIG. 16, data from sensors in the system can indicate when the phase is complete, for example, or PLC 106 (FIG. 1B) can move to the next phase after a pre-selected amount of time has elapsed. The recipe can specify how each phase is to be handled, or can leave it to computations conducted by PLC 106 (FIG. 1B), possibly based upon sensor data collected as the process is proceeding. Method 950 can include receiving 961 data from sensors associated with the culture vessel station in which the process is executing, and adjust 963 characteristics and parameters based on the sensor data, if necessary. Many such examples have been provided herein. Adjusting the thermal profile of the contents of the culture vessel relies on such data sensing in and around the culture vessel station. In particular, the sensor data may indicate that the phase is complete. If 965 there are more phases in the recipe, method 950 can include returning to step 959 and executing from that point. If 965 there are no more phases to execute in the recipe, and if 967 there are other recipes that are associated with the process(es), method 950 can include returning to step 953 and executing from that point. If 967 there are no other recipes, method 950 can include returning to step 951 and executing from that point.

In some configurations, exemplary phases for culturing cells are set out in Table I.

TABLE I

| Phase | Action | Configuration requirements |
|---|---|---|
| Add media x | Using valve x and pump x, add media to bioreactor | Specify the pump speed (mL/min), volume delivered, and tolerance |
| Remove media mid | Remove media to waste from a tube extended midway into the media using pump 2 | Specify the pump speed (mL/min), volume delivered, and tolerance |
| Remove media low | Remove media to waste from the a tube extending farther into the media using pump 2 | Specify the pump speed (mL/min), volume delivered, and tolerance |
| Agitate | Agitate with vortex up or vortex down options | Specify the agitator speed (RPM), and vortex up or down |
| Recirculate | Use specific valves (e.g. V5, V8, V10) to recirculate with pump 2 | Specify the pump speed (mL/min) |
| Low harvest | Harvest media to an external (to the bioreactor) vessel/bag, not waste. For example, remove all the media until the level sensor | Specify the pump speed (mL/min) |

TABLE I-continued

| Phase | Action | Configuration requirements |
|---|---|---|
| | reads less than 50 mL for 15 seconds | |
| Heat | Heat the vessel media to a specific temperature based on media temperature probe and heating sleeve probe | Specify the media temperature set point |
| pH DO | Control the pH and DO set points with the appropriate gas flow ration using the probes and MFCs and PID loops | Specify the pH and DO setpoints |
| Condense | Prevent wetting out the gas filter using a peltier and fan | Specify the PWM, for example, 99% |

In some configurations, exemplary phases for decellularizing scaffolds are set out in Table II.

TABLE II

| Phase | Action | Configuration requirements |
|---|---|---|
| Clear blood | Clear blood from the scaffold | Specify the volume (mL) and pressure (mmHg) |
| Lyse x | Break down the membrane of the cell in passes 1-x | Specify the time (min) and pressure (mmHg) |
| Remove debris | Remove debris from the scaffold | Specify the time (min) and pressure (mmHg) |
| Wash | Wash the scaffold | Specify the volume (mL) and pressure (mmHg) |
| Sterilize | Sterilize the scaffold | Specify the volume (mL) and pressure (mmHg) |

Figure 17A:
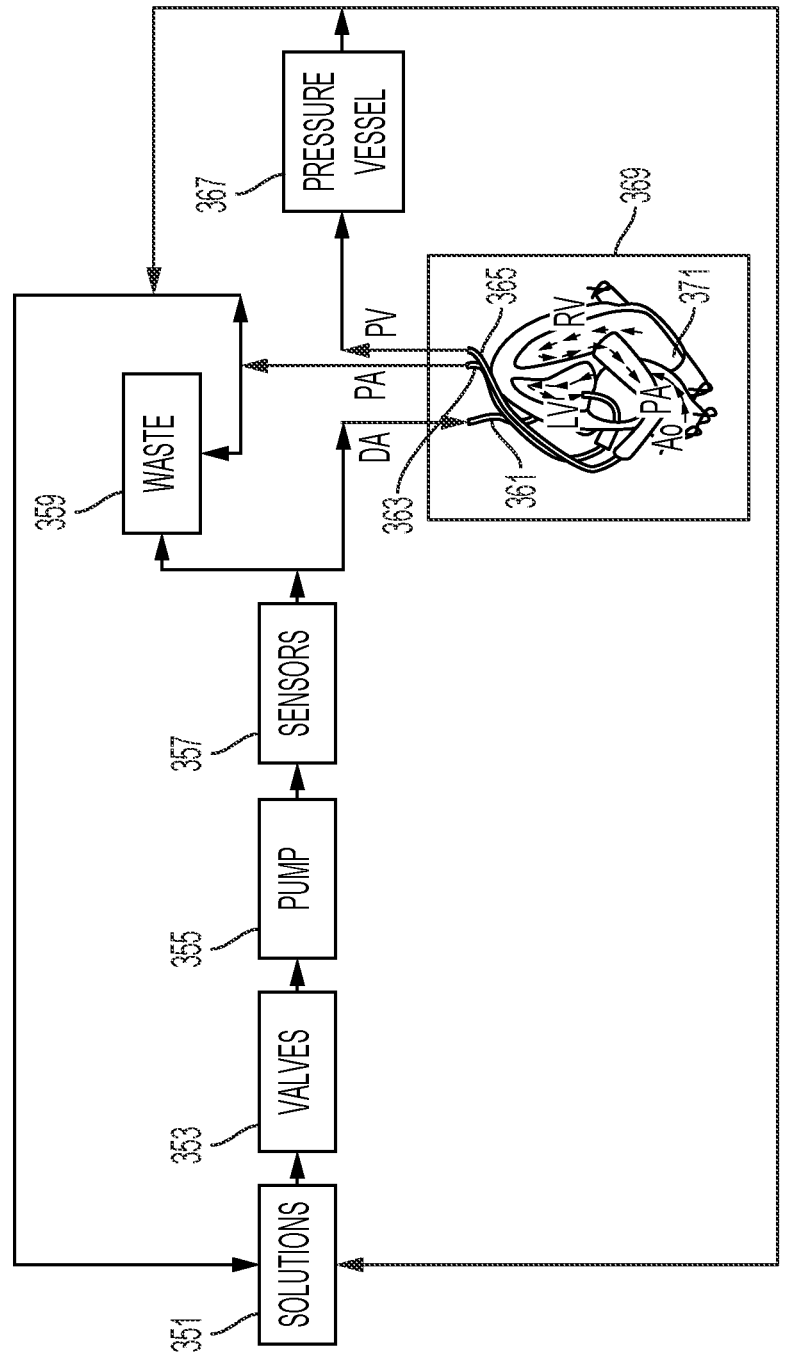
FIG. 17A is a schematic block diagram of an exemplary use of the system of the present teachings for decellularization of a heart.

Referring now to FIGS. 17A-17B, 18A-18C, and 19A-19B, various applications of the system to decellularizing a heart are shown along with various component layouts. Referring to FIG. 17A, a simplified fluid flow diagram of the system of the present teachings is shown with respect to the heart during decellularization. In particular, solutions 351 such as nutrients in the form of media are selected by valves 353 and pumped by pump 355 past sensors 357 selectively to either waste 359 or descending aorta 361. As the fluids are diffused through heart 371, they proceed from pulmonary artery 363 to either waste 359 or are recirculated back through heart 371. Fluids that exit heart 371 through pulmonary vein 365 to pressure vessel 367 and on to either waste 359 or recirculation. A pressure vessel is a leak-proof container that stores liquid or gas at higher or lower than atmospheric pressure. Pressure vessel 367 exerts back pressure on the fluid flowing out of bioreactor 369. In some configurations, the back pressure can result from indirect pressure through hydraulic head height at an elevation above bioreactor 369. The present teachings contemplate other methods for use of pressure vessel 367, and other configurations to produce the back pressure. In some configurations, pressure vessel 367 is vented, and the effluent flows to waste 359. Other configurations are contemplated by the present teachings. In some configurations, pressure vessel 367 can maintain a fixed pressure within the pulmonary vein/left ventricle to encourage a higher percentage of flow to exit the heart thorough the coronary arteries and out of the pulmonary artery. This pressure can maintain the heart in an inflated state. Other configurations, such as a pressure control loop, are contemplated by the present teachings. Various shapes of pressure vessels can be used, depending on the type of gas used to exert the pressure and the amount of pressure required. For example, types of pressure vessels include, but are not limited to including, cylindrical, conical, spherical, horizontal or vertical, which can be capped by various-shaped heads. For example, non-spherical pressure vessels require heads. Types of heads can include, for example, hemispheric-shaped and shallow-shaped (dished) heads (semi-elipsoidal or torispherical).

Figure 17B:
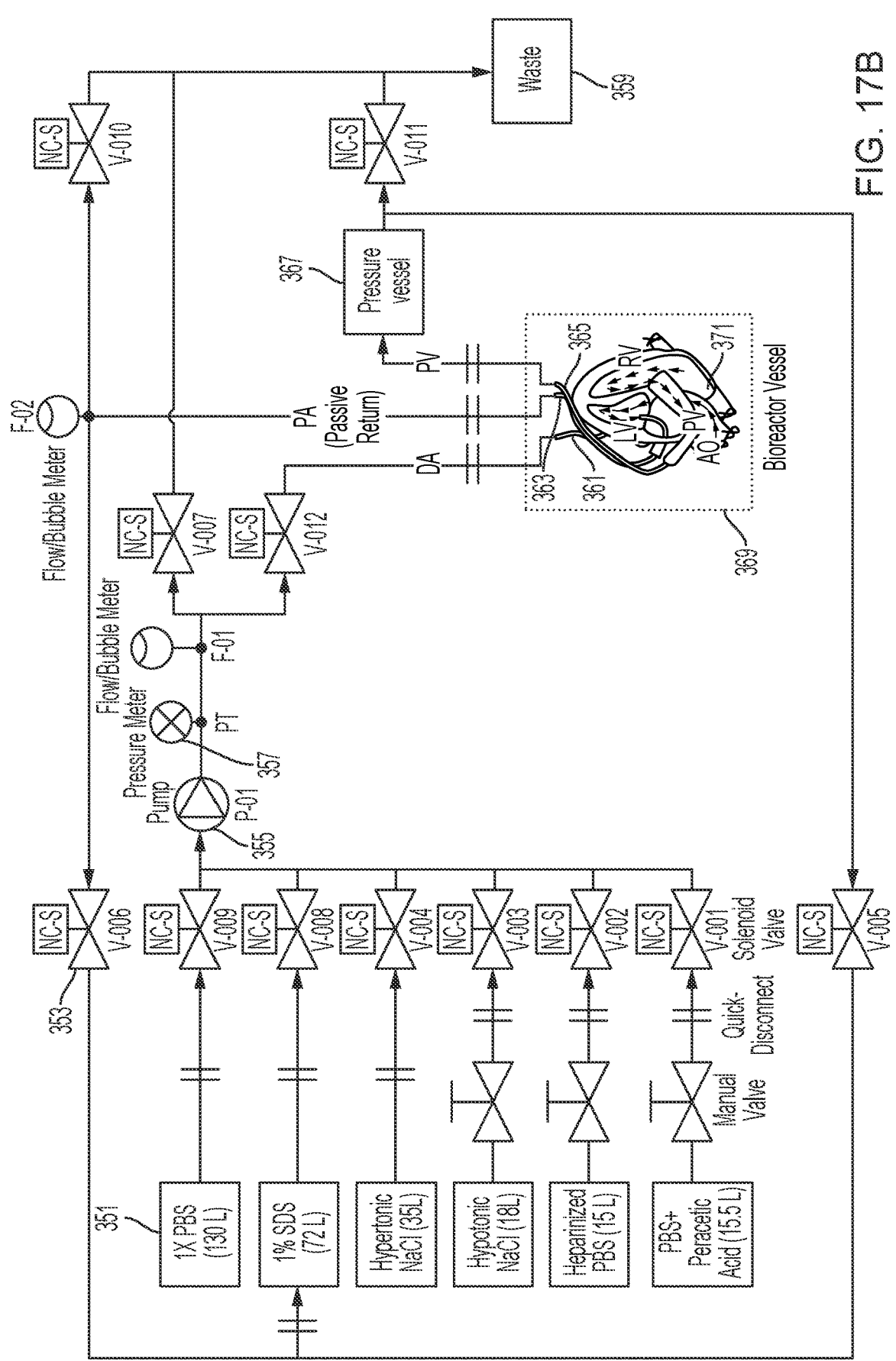
FIG. 17B is a schematic diagram of an exemplary valve configuration for decellularizing the heart using the system of the present teachings.

Referring now to FIG. 17B, for a specific decellularization configuration, solutions 351 can include, but are not limited to including, a buffered solution (PBS), detergent sodium dodecyl sulfate in distilled, deionized (DI) water (SDS), hypertonic NaCl, hypotonic sodium chloride (NaCl), heparinized PBS, and PBS with peracetic acid. Other decellularization solutions can include, but are not limited to including, detergent sodium deoxycholate (SD/SDC), detergent triton X-100, zwitterionic solutions such as 3-[(3-cholamidopropyl) dimethylammonio]-1-propanesulfonate (CHAPS), trypsin/ethylenediaminetetraacetic acid (EDTA), and deoxyribonulease (DNAse). SDS is a detergent that is known to denature proteins. Peracetic acid is used for sterilization of the final scaffold. Denaturing proteins involves breaking of many of the weak linkages or bonds, e.g. hydrogen bonds, within a protein molecule. The bonds are responsible for the ordered structure of the protein, so that denatured proteins have a looser, more random structure, and are likely insoluble. PBS is a phosphate-buffered solution, a water-based salt solution containing disodium hydrogen phosphate, sodium chloride, and possibly potassium chloride and potassium dihydrogen phosphate to help maintain a constant pH. Deionized water can be used to create predictable and repeatable results because it lacks ions from, for example, mineral salts like iron, calcium, and sulfate. Valves 353 in this configuration include a mixture of normally closed solenoid valves and manual valves. In some configurations, manual valves can be associated with certain source fluids such as, for example, but not limited to hypotonic NACl, helarinized PBC, and PBC/peracetic acid. In some configurations, manual valves can be used to assist in preventing leaks during setup and tear down processes, and are not used in the automated process. Manual valves can be used on the containers that hold the solutions that will be used in the process and are a way for these vessels to be filled off line, transported, and installed without risk of leaking or contaminating the solution in the source. The chosen solutions are pumped by pump 355 through pressure sensor 357 and flow/bubble meter to either waste 359 or bioreactor 369, specifically descending aorta 361. Pump 355 can include a peristaltic-variety pump that fulfills the desired pump characteristics described herein elsewhere.

Figure 18A:
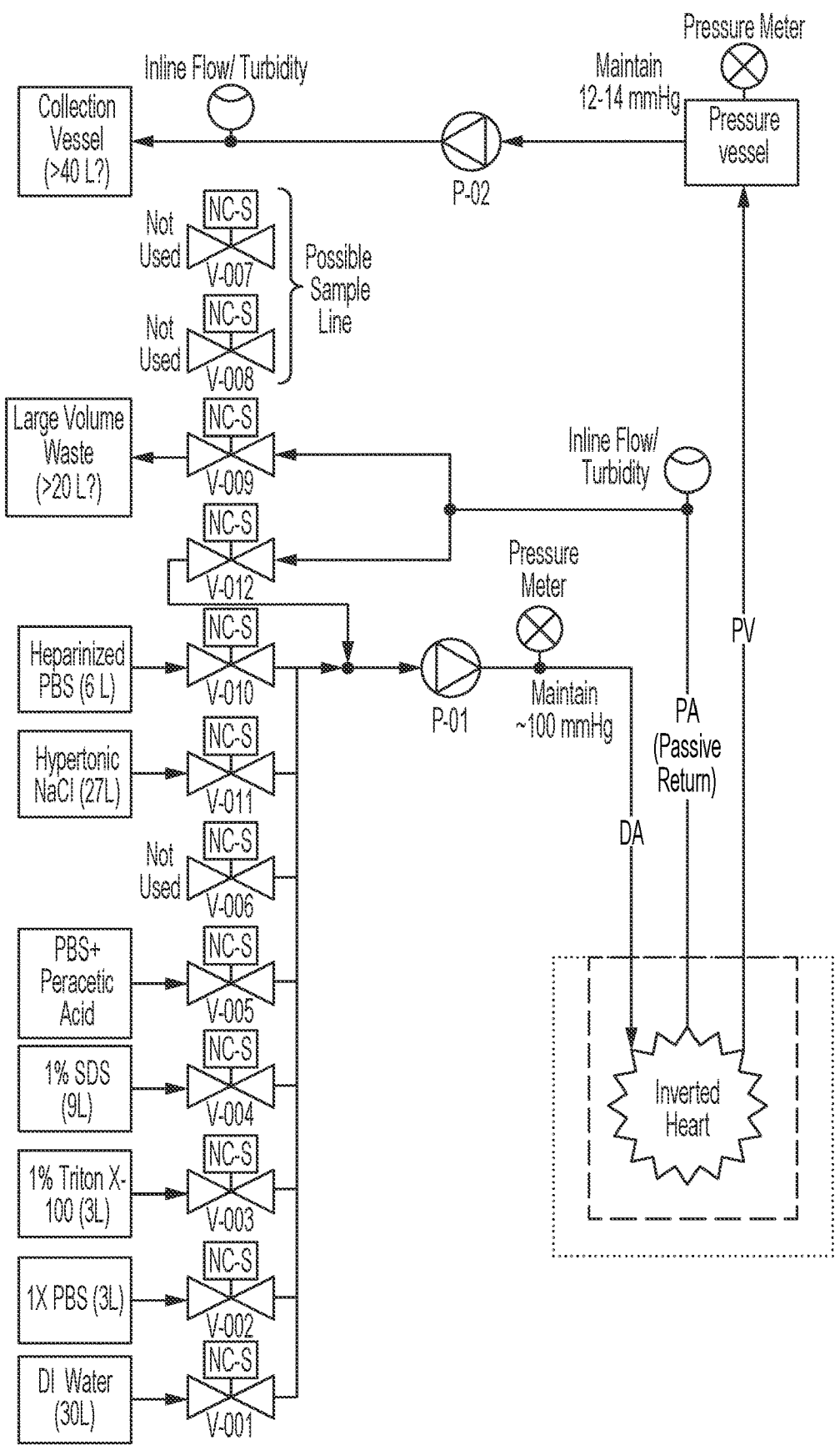

Referring now to FIGS. 18A-18C, an exemplary decellularization recipe and associated valve manipulations are shown. FIG. 18A and Tables III and IV describe methods that a system with two fluid pumps and twelve fluid valves might execute to decellularize an organ, such as a heart, and pump fluids to a collection vessel. Referring to FIG. 18A, in this exemplary use, fluid is pumped from a first pump from sources heparinized PBS, hypertonic NACl, PBS/peracetic acid, SDS, Triton, PBS, and deionized (DI) water past a pressure meter into the descending aorta. The fluid in the heart is routed to a waste or a collection vessel. Referring to FIG. 18B, the phases executed to accomplish a decellularization of a heart according to an exemplary recipe are listed. The first four phases involve clearing the blood from the heart using heparinized PBS pumped alternately by volume and by time/pressure by a first pump while the second pump is controlling the output to a pre-selected pressure. Note that the system of the present teachings allows variation in the values of pump volume, pressure, and time, and therefore the values listed in FIG. 18B are exemplary only. In the fifth phase, the last of the blood is flushed from the heart by DI water. The next phases involve lysing cells in the heart with NaCl, and then flushing the disrupted cells with DI water. Next, cell debris are removed from the heart by repeated applications of SDS and DI water. In this recipe, there are three repetitions of a debris removal sequence involving two applications of SDS following by one application of DI water. The last phases of substance remove the residual SDS using Triton. The final two phases involve washing the remaining scaffold with DI water and PBS. FIG. 18C lists the valves shown in FIG. 18A that are used for each phase listed on FIG. 18B.

Figure 19A:
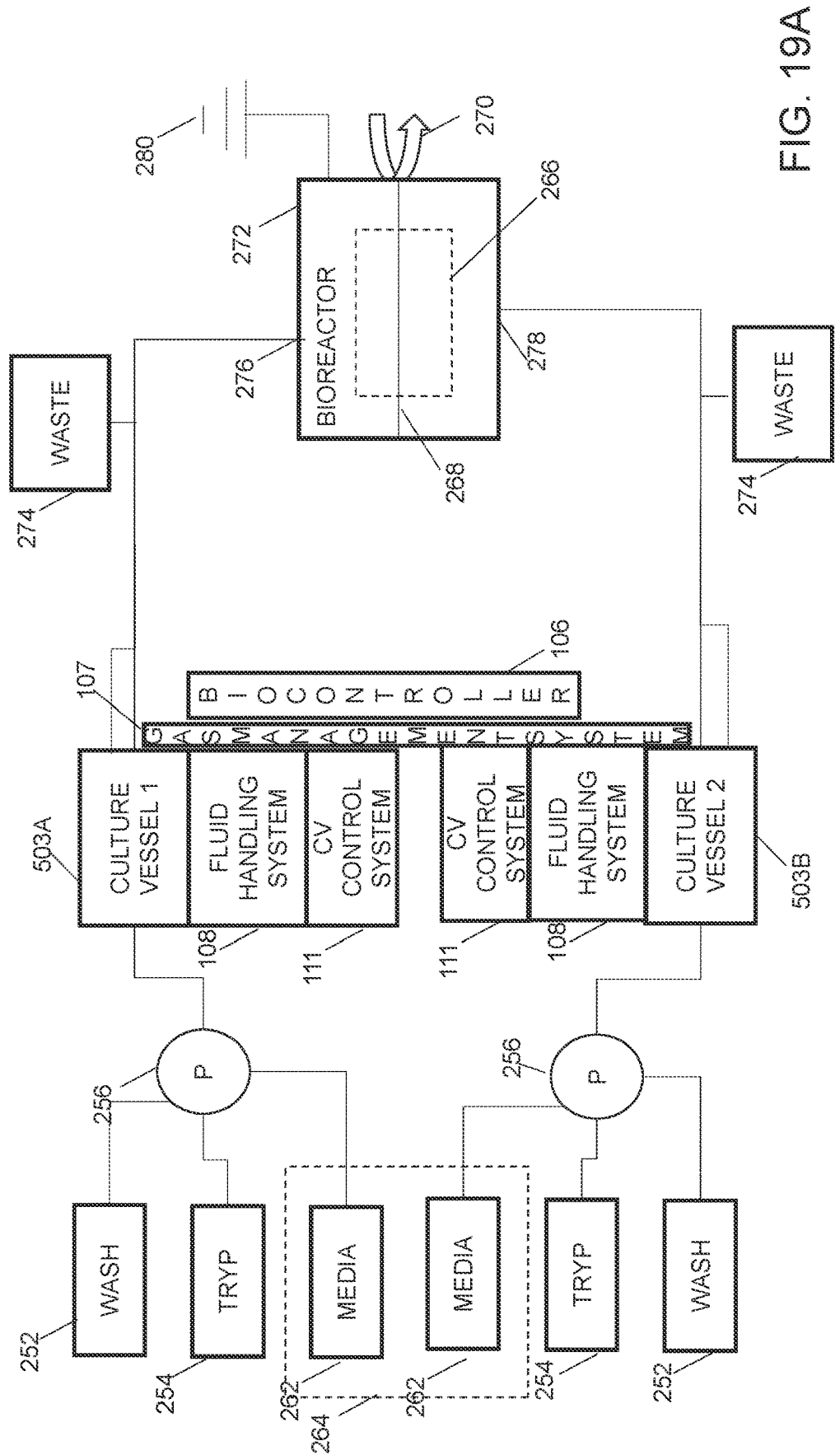
FIGS. 19A-19C are schematic block diagrams of an implementation of the present teachings in which multiple areas of a scaffold are seeded in the same bioreactor.
Figure 19B:
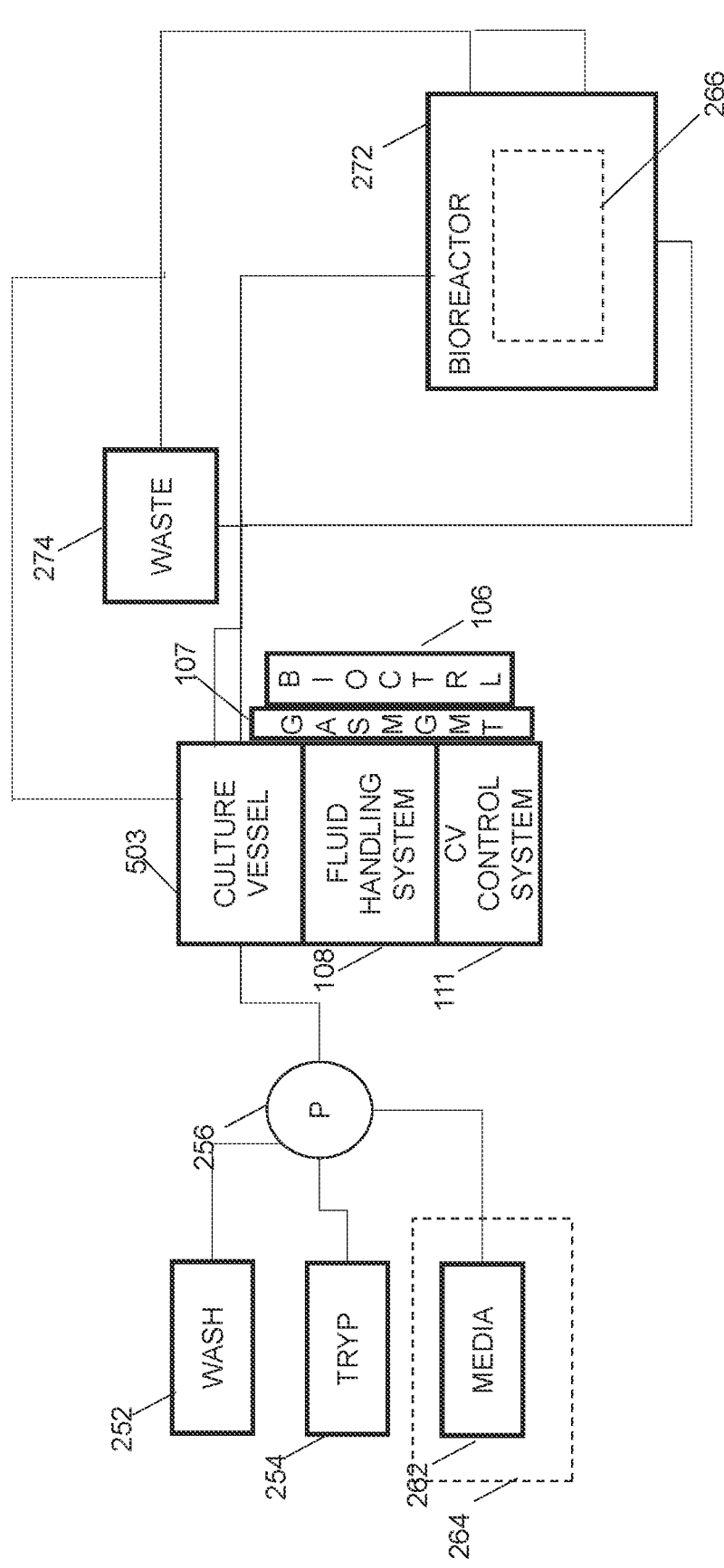
Figure 19C:
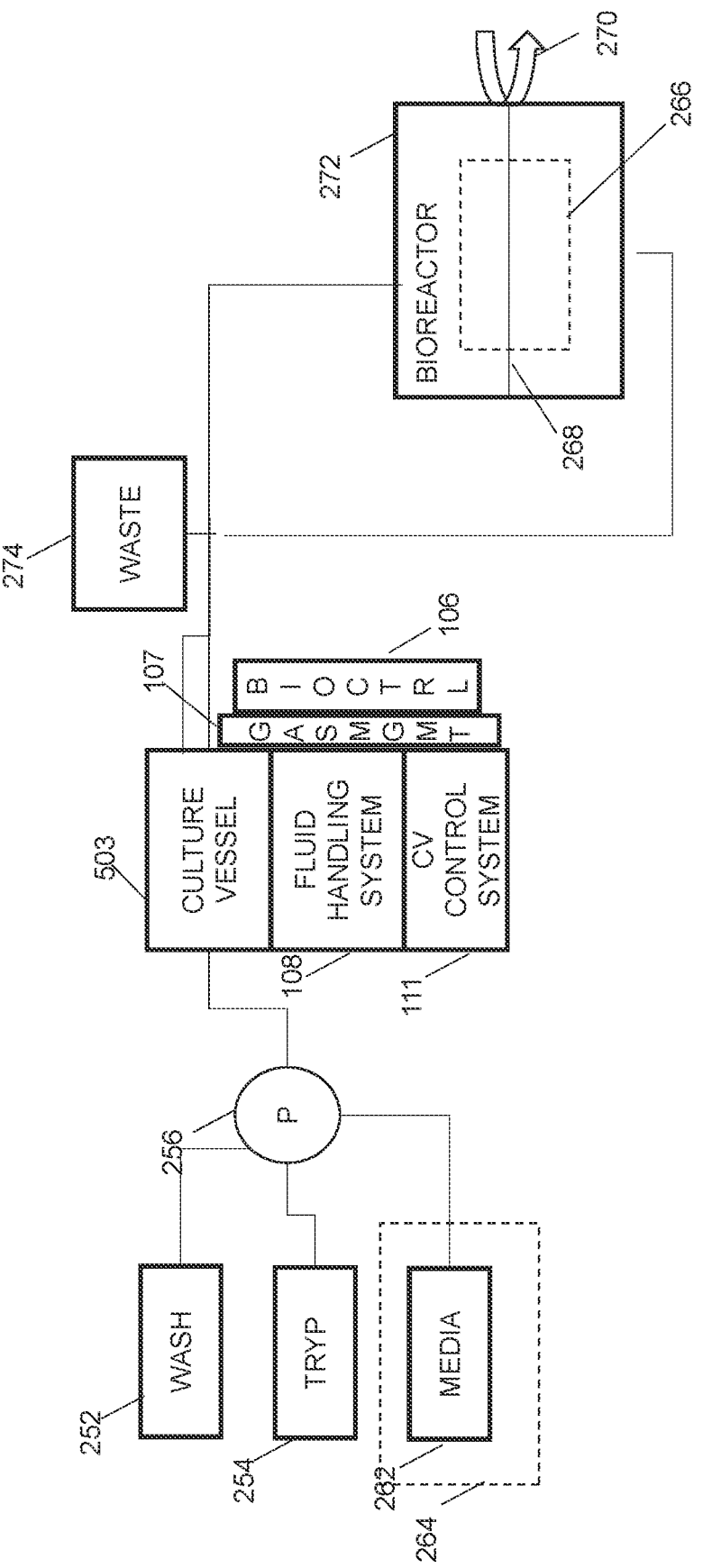

Referring now to FIGS. 19A-19C, yet another feature of the system of the present teachings includes growing one type of cell on one side of a culture vessel scaffold, another type on another side, and combining the two types of cells. Such a configuration can include source fluids, at least one culture vessel station including culture vessel 503A/B, fluid handling system 108, pumps 256, culture vessel control system 111, gas management 107, biocontroller 106, waste 274, bioreactor 272, rotation means 270, and vent 280, all of which have been described herein. In some configurations, scaffold 266 is fixed in the middle of bioreactor 272 with media/cell addition ports 276/278 entering bioreactor 272. Rotation feature 270 can move the area being seeded to a position in which the cells would be encouraged to rest and reproduce. Vent 280 or other outlet path can be configured to prevent pressure buildup. The system as shown in FIG. 19A can be used to expand cells such as suspension cells, aggregates, or cells on microcarriers. When the cell density reaches a target threshold, the cells are allowed to settle, the excess media removed, and wash solution 252, for example, but not limited to, PBS is added/removed. Trypsin 254 is added to digest the microcarriers/extra-cellular attachment proteins, high protein media 262 or inhibitor is added to quench trypsin 254, media 262 is added/removed to adjust its concentration, and then the cells are pumped to one side of scaffold 266. Additional media 262 can be used to clear out any cells in the tubing dead volume. The other side of scaffold 266 is seeded as soon as the first side of scaffold 266 is finished attaching by cells that are, for example, expanding simultaneously in second culture vessel 503B, or at a later time if the first layer developed in first culture vessel 503A needs time to mature. Media exchanges in bioreactor 272 are done, for example, continuously through a flow loop, or tidally using a vent. A second bioreactor (or a third bioreactor) can be configured to perform media exchanges in bioreactor 272. Choice of options is based at least on process timing, media composition, and tissue size/metabolism. Sensors (shown elsewhere) are placed in culture vessels 503A/B, media vessels 262, tissue bioreactor 272, and/or in any of the fluid pathways (for example, tissue bioreactor inlets/outlets 276/278). In some configurations, thermal control over media 262 is maintained in thermal device 264. Rotation means 270 can rotate scaffold 266 around axis of rotation 268. In some configurations, waste products can be routed away from bioreactor 272 and into waste collection 274. In some configurations, double-side seeding can be performed using a single culture vessel station and a single set of source fluids. In such systems, as illustrated in FIGS. 19B and 19C, culture vessel 503 can supply cells to both sides of scaffold 266 at different times. Some of the cells and the waste products produced in bioreactor 272 can return to culture vessel 503 and waste collection 274, respectively. Shown in FIG. 19C is rotation means 270 as described herein. In some configurations, cells that were expanded outside of the culture vessel system depicted in FIGS.

19A-19C can be provided to bioreactor 272 through specially-configured ports. In such configurations, multiple types of cells, both cells expanded in culture vessels 503 (FIG. 19B) and cells expanded elsewhere, can be introduced into bioreactor 272 to seed multiple areas of scaffold 266. Scaffold 266 is depicted as rectangular, but can assume any shape and size, according to the size of bioreactor 272. Further, multiple scaffolds 266 can be combined after the seeding process is complete to form a more complicated tissue.

A system for repeatably performing at least one type of tissue-related process as part of a manufacturing line, the system comprising: at least one culture vessel station including a variably-sized culture vessel, a fluid handling system, and a culture vessel control system, the at least one culture vessel station configured to accommodate performing the at least one type of tissue related process; a gas management system configured to provide at least one type of gas to the at least one culture vessel station; and a controller configured to control the gas management system and the at least one culture vessel station to perform the at least one type of tissue-related process, the controller configured to communicate using a standard industrial communications protocol with components on the manufacturing line. The system as described herein wherein the at least one variably-size culture vessel comprises disposable components. The system as described herein wherein the at least one variably-size culture vessel comprises durable components. The system as described herein wherein the at least one variably-size culture vessel comprises: a vessel sleeve surrounding at least a part of the at least one variably-sized culture vessel, the vessel sleeve configured to transfer thermal energy to the at least one variably-sized culture vessel; a thermal sleeve operably coupled with the vessel sleeve, the thermal sleeve controlling an amount of thermal energy entering the vessel sleeve; and a vessel clamp stabilizing the at least one variably-sized culture vessel within the thermal sleeve. The system as described herein wherein the fluid handling system is configured to move fluid through the at least one variably-sized culture vessel. The system as described herein further comprising: a sensor control system controlling of the amount of thermal energy entering the vessel sleeve. The system as described herein wherein the gas management system is configured to control a type and an amount of gas entering the at least one variably-sized culture vessel. The system as described herein wherein the vessel clamp comprises: a telescoping device, the telescoping device accommodating a height of the at least one variably-sized culture vessel. The system as described herein further comprising: a thermal break between the vessel sleeve and an environment surrounding the vessel sleeve. The system as described herein further comprising: an electric cutoff sensing when the thermal sleeve reaches at least one pre-selected threshold temperature, the electric cutoff configured to disable the addition of further thermal energy to the vessel sleeve. The system as described herein further comprising: at least one band clamp securing the thermal sleeve to the vessel sleeve. The system as described herein wherein the thermal sleeve comprises: at least one expansion/contraction gap. The system as described herein further comprising: a stabilizing pin configured to positionally secure the thermal sleeve to the vessel sleeve. The system as described herein further comprising: at least one temperature control element. The system as described herein further comprising: a thermally-conductive material filling a space between an inner diameter of the vessel sleeve and an outer diameter of the at least one variably-sized culture vessel. The system as described herein further comprising: a plurality of the vessel sleeves accommodating a plurality of sizes of the at least one variably-sized culture vessel. The system as described herein further comprising: a sensor system configured to monitor a variably-sized volume of cells in the at least one variably-sized culture vessel. The system as described herein wherein the fluid handling system comprises: a variable number of at least one valve and at least one pump configured to move the fluid into and out of the at least one variably-sized culture vessel station, the at least one controller controlling the at least one valve and the at least one pump. The system as described herein wherein the at least one controller comprises: instructions configured to control multiple of the at least one culture vessel stations performing independent tasks simultaneously. The system as described herein wherein a first of the at least one culture vessel stations performs a first type of the at least one type of tissue-related process in parallel with a second of the at least one culture vessel stations performing a second type of the at least one type of tissue-related process. The system as described herein wherein the first type of the at least one type of tissue-related process comprises a same type as the second type of the at least one type of the tissue-related process. The system as described herein wherein the first type of the at least one type of tissue-related process comprises a different type as the second type of the at least one type of the tissue-related process. The system as described herein wherein the first type of the at least one type of tissue-related process comprises decellularization. The system as described herein wherein the first type of the at least one type of tissue-related process comprises recellularization. The system as described herein wherein the first type of the at least one type of tissue-related process comprises cell maturation of recellularized tissue. The system as described herein wherein the first type of the at least one type of tissue-related process comprises perfusion of endothelial cells. The system as described herein wherein the at least one controller comprises: determining a fluid flow path based at least on a recipe. The system as described herein wherein the at least one controller comprises: determining a fluid flow path dynamically. The system as described herein wherein the at least one controller comprises: determining a fluid flow path based at least on user input. The system as described herein wherein the at least one controller comprises: determining a fluid flow path based at least on a combination of a recipe, dynamically-determined parameters, and user-provided parameters. The system as described herein wherein the at least one tissue-related process comprises: creating a batch. The system as described herein wherein the batch is produced in compliance with at least one industry standard process. The system as described herein wherein the at least one industry standard process comprises: ANSI/ISA-88.01-1995. The system as described herein wherein the standard industrial communications protocol comprises: Ethernet/Industrial Protocol. The system as described herein wherein the gas management system comprises: at least one mass flow controller configured to receive a source of gas, the amount of the gas controlled by the at least one controller; a mixing manifold configured to blend a plurality of types of the gas from a plurality of the at least one mass flow controller, the amounts and types of the plurality of types of the gas controlled by the at least one controller; and a distribution manifold receiving the blended plurality of gasses and distributing the blended plurality of gases to the at least one culture station according to commands from the at least one controller. The system as described herein wherein a number of the at least one mass flow controller is independent from the number of at least one culture vessel station. The system as described herein wherein a plurality of the at least one mass flow controller is configured to provide the amounts and types of the plurality of types of the gas to a plurality of the at least one culture vessel station according to a periodic delivery function. The system as described herein wherein the periodic delivery function is based at least on values collected by sensors associated with the at least one culture vessel station. The system as described herein further comprising: a cone feature attached to shaft of an agitation device in the culture vessel, the cone feature substantially preventing cells from settling on the agitation device. A method for seeding a plurality of types of cells on a plurality of areas of a scaffold, the method comprising: operably coupling the scaffold with a rotation means in a bioreactor, the bioreactor configured to accept a plurality of types of cells through a plurality of ports in the bioreactor; when cell density of a first cell type of the plurality of types of cells in a first culture vessel reaches a pre-selected threshold, or after a pre-selected waiting period, (a) removing excess media from the culture vessel; (b) washing first cells of the first cell type in the culture vessel; (c) digesting the microcarriers/extra-cellular attachment proteins in the culture vessel using a digesting solution; (d) quenching the digesting solution; and (e) adjusting the concentration of the media; pumping the first cells from the culture vessel to a first area of the plurality of areas of the scaffold in the bioreactor; and when a first pre-selected time has passed, processing a second cell type of the plurality of cell types according to steps (a)-(e); and pumping the second cells from the culture vessel to a second area of the plurality of areas of the scaffold in the bioreactor, the second cell type created in a second culture vessel. The method as described herein further comprising: rotating the scaffold after the first area is seeded, the rotating positioning the scaffold to accept the second type of the plurality of cells onto the second area.

Various alternatives and modifications can be devised by those skilled in the art without departing from the disclosure. Accordingly, the present disclosure is intended to embrace all such alternatives, modifications and variances. Additionally, while several example configurations of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular configurations. In addition, those skilled in the art will envision other modifications within the scope and spirit of the claims appended hereto. Other elements, steps, methods and techniques that are insubstantially different from those described above and/or in the appended claims are also intended to be within the scope of the disclosure.

The drawings are presented only to demonstrate certain examples of the disclosure. In addition, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the example configurations of the disclosure described herein are capable of operation in other sequences and/or arrangements than are described or illustrated herein.

The invention claimed is:

1. A system for repeatably performing at least one type of tissue-related process as part of a manufacturing line, the system comprising:
   at least one variably-sized culture vessel including a vessel sleeve surrounding at least a section of the at least one variably-sized culture vessel, the vessel sleeve configured to transfer thermal energy to the at least one variably-sized culture vessel, a thermal sleeve operably coupled with the vessel sleeve, the thermal sleeve controlling an amount of thermal energy entering the vessel sleeve; and a vessel clamp stabilizing the at least one variably-sized culture vessel within the thermal sleeve;
   a fluid handling system including at least one pump, at least one valve and at least one sensor, the fluid handling system moving fluid through said at least one variably-sized culture vessel;
   a culture vessel controller, controlling said fluid handling system by monitoring said at least one sensor and adjusting said at least one valve to maintain setpoints within said at least one variably-sized culture vessel perform the at least one type of tissue-related process;
   a gas management system providing at least one type of gas to the at least one variably-sized culture vessel; and
   at least one controller monitoring the status of culture vessel controller and scheduling the at least one type of tissue-related process as between components on the manufacturing line using a standard industrial communications protocol.

2. The system as in claim 1 wherein the at least one variable-sized culture vessel comprises disposable components.

3. The system as in claim 1 wherein the at least one variably-sized culture vessel comprises durable components.

4. The system as in claim 1 wherein the fluid handling system is configured to move fluid through the at least one variably-sized culture vessel.

5. The system as in claim 4 wherein the fluid handling system comprises:
   a variable number of at least one valve and at least one pump configured to move the fluid into and out of the at least one variably-sized culture vessel, the at least one controller controlling the at least one valve and the at least one pump.

6. The system as in claim 1 further comprising:
   a temperature sensor in communication with the at least one controller to control of the amount of thermal energy entering the vessel sleeve.

7. The system as in claim 1 wherein the gas management system controls a type and an amount of gas entering the at least one variably-sized culture vessel.

8. The system as in claim 1 wherein the vessel clamp comprises:
   a telescoping device, the telescoping device accommodating a height of the at least one variably-sized culture vessel.

9. The system as in claim 1 further comprising:
   a thermal break between the vessel sleeve and an environment surrounding the vessel sleeve.

10. The system as in claim 1 further comprising:
    an electric cutoff sensing when the thermal sleeve reaches at least one pre-selected threshold temperature, the electric cutoff configured to disable an addition of further thermal energy to the vessel sleeve.

11. The system as in claim 1 further comprising:
    at least one band clamp securing the thermal sleeve to the vessel sleeve.

12. The system as in claim 1 wherein the thermal sleeve comprises: at least one expansion/contraction gap.

13. The system as in claim 1 further comprising:
    a stabilizing pin configured to positionally secure the thermal sleeve to the vessel sleeve.

14. The system as in claim 1 further comprising: at least one temperature control element.

15. The system as in claim 1 further comprising:
    a thermally-conductive material filling a space between an inner diameter of the vessel sleeve and an outer diameter of the at least one variably-sized culture vessel.

16. The system as in claim 1 further comprising:
    a plurality of the vessel sleeve accommodating a plurality of sizes of the at least one variably-sized culture vessel.

17. The system as in claim 1 further comprising:
    a sensor system configured to monitor a variably-sized volume of cells in the at least one variably-sized culture vessel.

18. The system as in claim 1 wherein the at least one controller comprises:
    instructions configured to control multiple of the at least one variably-sized culture vessel performing independent tasks simultaneously.

19. The system as in claim 18 wherein a first of the at least one variably-sized culture vessel performs a first choice of the at least one type of tissue-related process in parallel with a second of the at least one variably-sized culture vessel performing a second choice of the at least one type of tissue-related process.

20. The system as in claim 19 wherein the first type of the at least one choice of at least one type of tissue-related process comprises a same selection as the second choice of the at least one type of the tissue-related process.

21. The system as in claim 20 wherein the first type of the at least one type of issue-related process comprises decellularization.

22. The system as in claim 20 wherein the first type of the at least one type of tissue-related process comprises recellularization.

23. The system as in claim 20 wherein the first type of the at least one type of tissue-related process comprises cell maturation of recellularized tissue.

24. The system as in claim 20 wherein the first type of the at least one type of tissue-related process comprises perfusion of endothelial cells.

25. The system as in claim 19 wherein the first choice of the at least one type of tissue-related process comprises a different selection as the second choice of the at least one type of the tissue-related process.

26. The system as in claim 1 wherein the at least one controller comprises: determining a fluid flow path based at least on a recipe.

27. The system as in claim 1 wherein the at least one controller comprises: determining a fluid flow path dynamically.

28. The system as in claim 1 wherein the at least one controller comprises: determining a fluid flow path based at least on user input.

29. The system as in claim 1 wherein the at least one controller comprises:
   determining a fluid flow path based at least on a combination of a recipe, dynamically-determined parameters, and user-provided parameters.

30. The system as in claim 1 wherein the at least one type of tissue-related process comprises: a batch process.

31. The system as in claim 30 wherein the batch is produced in compliance with at least one industry standard process.

32. The system as in claim 31 wherein the standard industrial communications protocol comprises:
   Ethernet/Industrial Protocol.

33. The system as in claim 31 wherein the at least one industry standard process comprises: ANSI/ISA-88.01-1995.

34. The system as in claim 1 wherein the gas management system comprises:

at least one mass flow controller configured to receive a source of gas, the amount of the gas controlled by the at least one controller; a mixing manifold configured to blend a plurality of types of the gas from a plurality of the at least one mass flow controller, the amounts and types of the plurality of types of the gas controlled by the at least one controller; and a distribution manifold receiving the blended plurality of gasses and distributing the blended plurality of gases to the at least one variably-sized culture vessel according to commands from the at least one controller.

35. The system as in claim 34 wherein a controller number of the at least one mass flow controller is independent from a vessel number of at least one variably-sized culture vessel.

36. The system as in claim 35 wherein a plurality of the at least one mass flow controller is configured to provide the amounts and types of the plurality of types of the gas to a plurality of the at least one variably-sized culture vessel according to a periodic delivery function.

37. The system as in claim 36 wherein the periodic delivery function is based at least on values collected by sensors associated with the at least one variably-sized culture vessel.

38. The system as in claim 1 further comprising:

a cone feature attached to shaft of an agitation device in the at least one culture vessel, the cone feature substantially preventing cells from settling on the agitation device.

* * * * *